United States Patent
Yasuda et al.

(10) Patent No.: US 11,279,680 B2
(45) Date of Patent: Mar. 22, 2022

(54) DICYANO N-HETEROCYCLIC COMPOUND, LIGHT-EMITTING MATERIAL, AND LIGHT-EMITTING ELEMENT IN WHICH SAME IS USED

(71) Applicants: KYUSHU UNIVERSITY, NATIONAL UNIVERSITY CORPORATION, Fukuoka (JP); Nippon Soda Co., Ltd., Tokyo (JP)

(72) Inventors: Takuma Yasuda, Fukuoka (JP); Ryuhei Furue, Fukuoka (JP); Hiroyuki Ishihara, Kurashiki (JP); Yukio Fukushima, Kurashiki (JP)

(73) Assignees: Kyushu University, National University Corporation, Fukuoka (JP); Nippon Soda Co., Ltd., Tokyo (JP)

(*) Notice: Subject to any disclaimer, the term of this patent is extended or adjusted under 35 U.S.C. 154(b) by 362 days.

(21) Appl. No.: 16/471,980

(22) PCT Filed: Jan. 9, 2018

(86) PCT No.: PCT/JP2018/000164
§ 371 (c)(1),
(2) Date: Jun. 20, 2019

(87) PCT Pub. No.: WO2018/131557
PCT Pub. Date: Jul. 19, 2018

(65) Prior Publication Data
US 2019/0330162 A1  Oct. 31, 2019

(30) Foreign Application Priority Data
Jan. 13, 2017 (JP) .................. JP2017-004715

(51) Int. Cl.
*C07D 241/36* (2006.01)
*C07D 401/10* (2006.01)
(Continued)

(52) U.S. Cl.
CPC ......... *C07D 241/36* (2013.01); *C07D 401/14* (2013.01); *C07D 403/10* (2013.01);
(Continued)

(58) Field of Classification Search
CPC .. C07D 241/36; C07D 401/10; C07D 403/10; C07D 413/10
See application file for complete search history.

(56) References Cited

U.S. PATENT DOCUMENTS

| | | |
|---|---|---|
| 2015/0239880 A1 | 8/2015 | Adachi et al. |
| 2016/0064676 A1 | 3/2016 | Adachi et al. |
| 2018/0273513 A1 | 9/2018 | Yasuda et al. |

FOREIGN PATENT DOCUMENTS

| | | |
|---|---|---|
| CN | 101514262 A | 8/2009 |
| CN | 104830320 A * | 8/2015 |

(Continued)

OTHER PUBLICATIONS

Wen et al., Synthetic Metals, 1998, 97, 105-112.*
(Continued)

*Primary Examiner* — Vu A Nguyen
(74) *Attorney, Agent, or Firm* — Foley & Lardner LLP

(57) ABSTRACT

Provided are: a dicyano N-heterocyclic compound represented by formula (I) (in the formula, $R^3$ represents an electron-donating group, and n represents the number of repetitions of the content in brackets and is 0 or 1), the compound having exceptional heat resistance and light emission characteristics; a light-emitting material; and a light-emitting element in which the same is used.
(Continued)

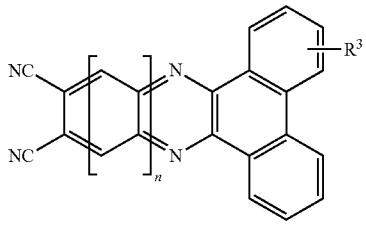

(I)

4 Claims, 13 Drawing Sheets

(51) Int. Cl.
C07D 403/10 (2006.01)
C07D 413/10 (2006.01)
C09K 11/06 (2006.01)
H01L 51/00 (2006.01)
H01L 51/50 (2006.01)
C07D 401/14 (2006.01)

(52) U.S. Cl.
CPC ........ C07D 413/10 (2013.01); H01L 51/0059 (2013.01); H01L 51/0072 (2013.01); H01L 51/0073 (2013.01); H01L 51/5012 (2013.01)

(56) References Cited

FOREIGN PATENT DOCUMENTS

| CN | 105121428 A | 12/2015 | |
| JP | 6434791 A * | 2/1989 | ............. G11B 7/248 |
| JP | S6434791 A | 2/1989 | |
| JP | H0532640 A | 2/1993 | |
| JP | H11-138974 A | 5/1999 | |
| JP | 2001-002661 A | 1/2001 | |
| JP | 2001-261658 A | 9/2001 | |
| JP | 2005-260094 A | 9/2005 | |
| JP | 2007-204443 A | 8/2007 | |
| JP | 2015-153864 A | 8/2015 | |
| JP | 2015-172166 A | 10/2015 | |
| KR | 10-2015-0050570 A | 5/2015 | |
| WO | WO-2017/082246 A1 | 5/2017 | |

OTHER PUBLICATIONS

McDaniel and Brown, J. Org. Chem. 1958, 23, 3, 420-427.*
Wang et al., Angew. Chem. Int. Ed. 2015, 54, 13068-13072.*
Wang et al., ACS Appl. Mater. Interfaces 2017, 9, 9892-9901.*
Decision to Grant dated Feb. 17, 2021 in KR 10-2019-7018714, with English translation.
Cai et al., ""Rate-limited effect" of reverse intersystem crossing process: the key fortuning thermally activated delayed fluorescence lifetime and efficiency roll-off of organic light emitting diodes," The Royal Society of Chemistry 2016, Chem. Sci. Mar. 2016, pp. 4264-4275.
International Search Report dated Feb. 20, 2018, in PCT/JP2018/000164, with English translation.
Sato et al., "Synthesis of 3,6-Dibromopyrazine-2,5-dicarbonitrile," Journal of Heterocyclic Chemistry, May 2012, vol. 49, pp. 675-677.
Wen et al., "Substituted tetra-2,3-pyrazinoporphyrazinino copper(II) complexes: synthesis and nonlinear optical refractive and absorptive properties," Synthetic Metals, 1998, vol. 97, pp. 105-112.
Office Action dated Jun. 3, 2021 in CN 201880006049.4, with English translation of search report.
Wang, Shipan, "Dicyano-Substituted Aromatic Conjugated Groups as Electron Acceptors for the Construction of Thermally Activated Delayed Fluorescence Material Systems," Chinese Doctoral Dissertation Full-text Database, CDFD (electronic journal), Engineering Science and Technology, series 1, Nov. 30, 2017, 151 pages, with English abstract.

* cited by examiner

DICYANO N-HETEROCYCLIC COMPOUND, LIGHT-EMITTING MATERIAL, AND LIGHT-EMITTING ELEMENT IN WHICH SAME IS USED

TECHNICAL FIELD

The present invention relates to a dicyano N-heterocyclic compound, a light-emitting material, and a light-emitting element in which the same is used. More specifically, the present invention relates to a dicyano N-heterocyclic compound which has both excellent heat resistance and light emission characteristics, a light-emitting material, and a light-emitting element using the same.

CROSS-REFERENCE TO RELATED APPLICATIONS

The present invention is the U.S. National Stage of PCT/JP2018/000164, filed Jan. 9, 2018, which claims priority on the basis of Japanese Patent Application No. 2017-004715 filed in Japan on Jan. 13, 2017, the contents of which are incorporated herein by reference.

BACKGROUND OF THE INVENTION

Some compounds having a pyrazine dicarbonitrile skeleton or a quinoxaline dicarbonitrile skeleton are useful as electron transporting materials, charge generation materials, optical recording materials, photoelectric conversion materials, or light-emitting materials.

For example, Patent Document 1 discloses an organic solid fluorescent substance containing N,N,N',N'-tetrakis(2-methylbenzyl)-2,5-diamino-3,6-pyrazine carbonitrile crystals, represented by formula (1), the maximum reflectance in the visible light region of the solid, determined by reflectometry using a rear spectroscopic method, being 100% or more.

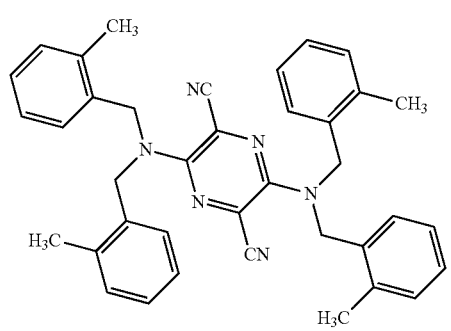

(1)

Patent Document 2 discloses a film in which a compound having a quinoxaline skeleton of formula (3) or a 2,3-dicyanopyrazine skeleton of formula (4) is added to 1,4,5,8,9,11-hexaazatriphenylenehexacarbonitrile of formula (2).

The film may be used in an organic electronic device such as an organic electroluminescent element or an organic thin-film solar cell.

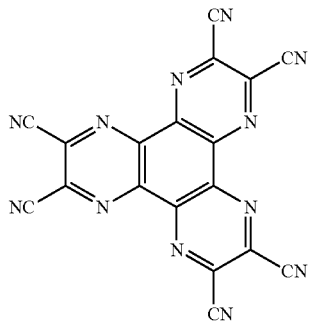

(2)

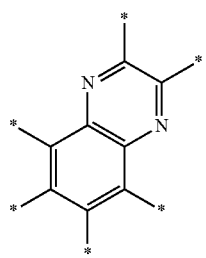

(3)

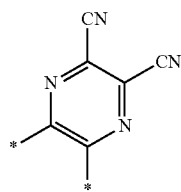

(4)

Patent Document 3 discloses an organic electroluminescent element having a layer containing a dicyanopyrazine-based compound of formula (5) between an opposing anode and cathode.

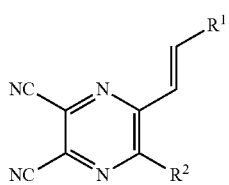

(5)

In formula (5), $R^1$ and $R^2$ each independently represents a heterocyclic group which may have a substituent or a hydrocarbon ring group which may have a substituent.

Patent Document 4 discloses compounds of formula (6) or the like. The compounds may be used as electron transporting materials, charge generation materials, optical recording materials, or photoelectric conversion materials.

(6)

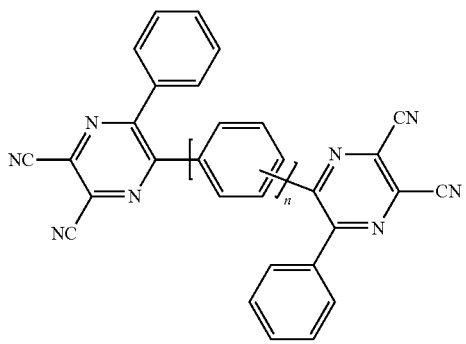

Patent Documents 5 and 6 disclose compounds of formula (7), formula (8), or the like. The compounds may be used as functional materials such as electroluminescence or wavelength-conversion materials.

(7)

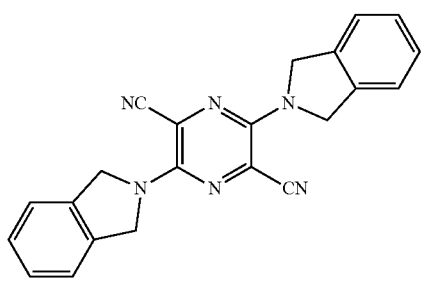

(8)

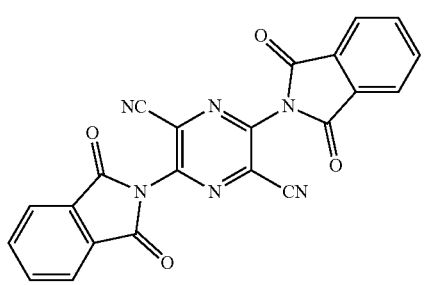

Patent Document 7 discloses a light-emitting material composed of a compound in which a cyanopyridine as an electron-attracting site and a heteroaryl group as an electron-donating site are bonded.

Patent Document 8 discloses compounds of formula (9) or formula (10).

(9)

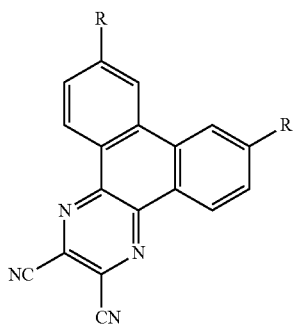

(10)

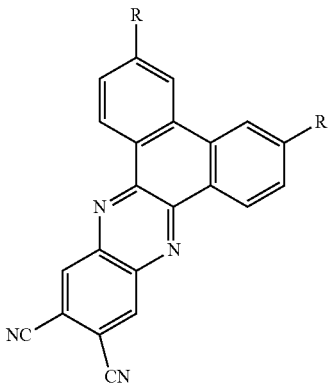

Non-Patent Document 1 discloses a multiple-stage synthesis method of 3,6-dibromopyrazine-2,5-dicarbonitrile.

Non-Patent Document 2 discloses a compound of formula (11) or (12).

(11)

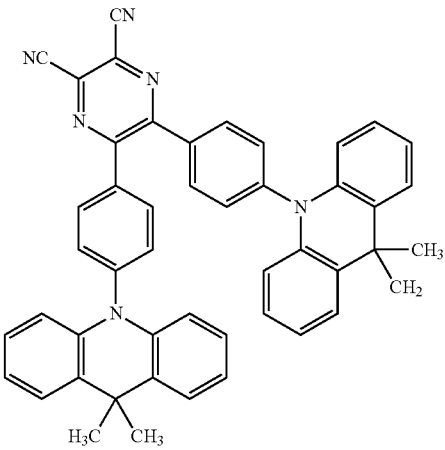

(12)

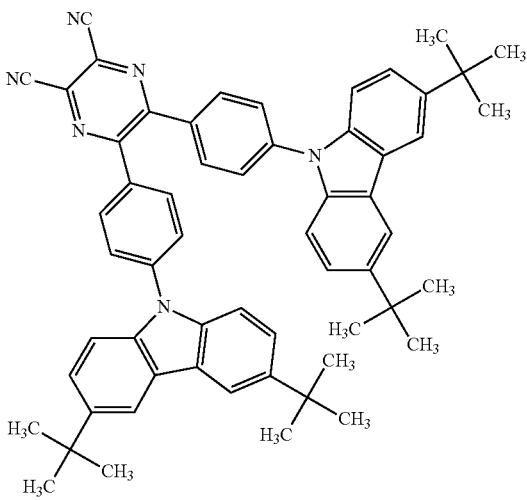

DOCUMENTS OF RELATED ART

Patent Documents

Patent Document 1: Japanese Unexamined Patent Application Publication No. 2007-204443
Patent Document 2: Japanese Unexamined Patent Application Publication No. 2015-153864
Patent Document 3: Japanese Unexamined Patent Application Publication No. 2001-261658
Patent Document 4: Japanese Unexamined Patent Application Publication No. 2001-2661
Patent Document 5: Japanese Unexamined Patent Application Publication No. Hei 5-32640
Patent Document 6: Japanese Unexamined Patent Application Publication No. Hei 11-138974
Patent Document 7: Japanese Unexamined Patent Application Publication No. 2015-172166
Patent Document 8: CN 104830320 A

Non-Patent Documents

Non-Patent Document 1: N. Sato et al. "Synthesis of 3,6-Dibromopyrazine-2,5-dicarbonitrile" Journal of Heterocyclic Chemistry, Vol. 49, May 2012, 675-677
Non-Patent Document 2: Xinyi Cai et al., "Rate-limited effect" of reverse intersystem crossing process: the key for tuning thermally activated delayed fluorescence lifetime and efficiency roll-off of organic light emitting diodes, The Royal Society of Chemistry 2016 Chem. Sci. Mar. 15, 2016, 4264-4275

SUMMARY OF THE INVENTION

Problems to be Solved by the Invention

However, it became clear that a disubstituted compound disclosed in Patent Document 8 or Non-Patent Document 2 has a large molecular weight and is easily decomposed by heat.

The aims of the present invention are to provide a dicyano N-heterocyclic compound which has excellent heat resistance and light emission characteristics, a light-emitting material, and a light-emitting element using the same.

Means to Solve the Problems

As a result of intensive studies to solve the above problems, the present invention including the following aspects has been completed.

That is, the present invention relates to the following aspects.

[1] A compound of formula (I).

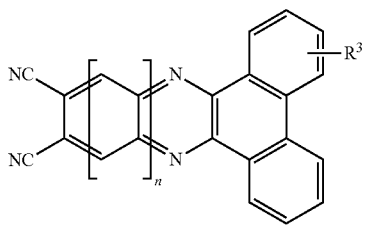

(I)

In formula (I), $R^3$ represents an electron-donating group, and n represents the number of repetitions of the content in brackets and is 0 or 1.

[2] The compound according to [1], wherein the electron-donating group is a phenyl group having a substituent, and the substituent is a hetero ring in which at least two substituted or unsubstituted aromatic rings are condensed, or a substituted or unsubstituted diarylamino group.

[3] The compound according to [1] or [2], wherein $R^3$ is at least one selected from the group consisting of groups of formula (d1) to formula (d4).

(d1)

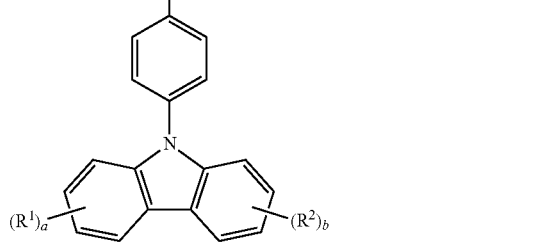

(d2)

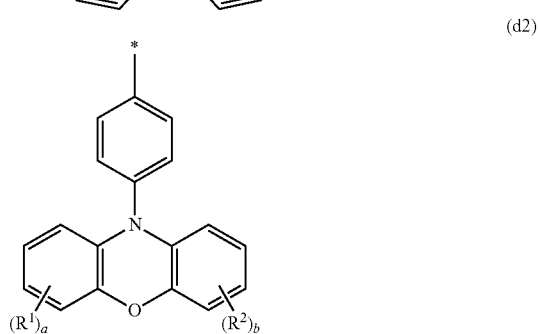

(d3)

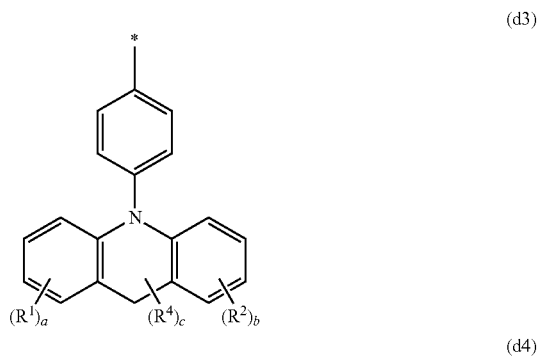

(d4)

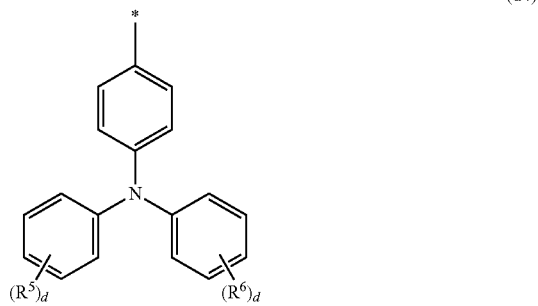

In the formulae (d1) to (d4), $R^1$, $R^2$, $R^4$, $R^5$ and $R^6$ each independently represents a substituent; a and b each independently represents the number of $R^1$ or $R^2$ in brackets and is any one of integers of 0 to 4; c represents the number of $R^4$ in brackets and is any one of integers of 0 to 2; d each independently represents the number of $R^5$ or $R^6$ in brackets and is any one of integers of 0 to 5; when each of $R^1$, $R^2$, $R^4$, $R^5$ or $R^6$ is plurally substituted, the substituents may be identical to or different from each other, two adjacent substituents may bond together to form a ring with carbon atoms bonded with the substituents, and * represents a bonding position.

[4] A light-emitting material containing at least one of the compounds of [1] to [3] mentioned above.

[5] A light-emitting element containing the light-emitting material of [4].

Effects of the Invention

A dicyano N-heterocyclic compound according to the present invention is useful as a light-emitting material. The light-emitting material according to the present invention may emit delayed fluorescence. A light-emitting element containing the light-emitting material according to the present invention can realize excellent luminous efficiency.

EMBODIMENTS FOR CARRYING OUT THE INVENTION

Figure 1:
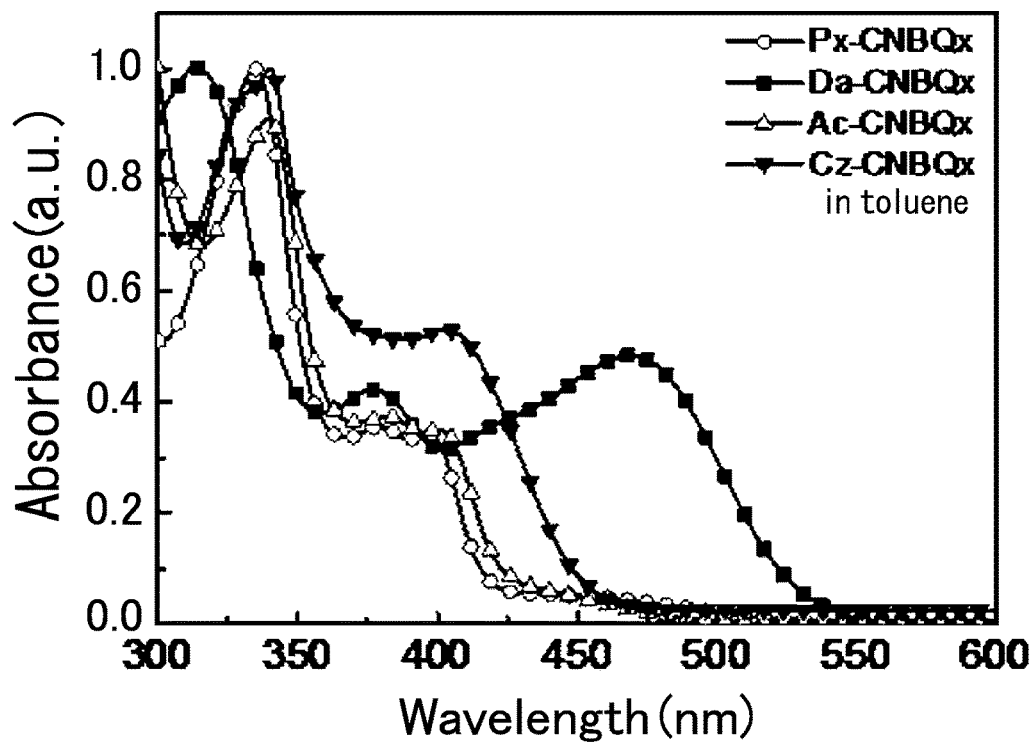
FIG. 1 is a drawing that indicates absorption spectra of a Px-CNBQx toluene solution, a Da-CNBQx toluene solution, an Ac-CNBQx toluene solution, and a Cz-CNBQx toluene solution, prepared in Example 5.

A dicyano N-heterocyclic compound according to the present invention is a compound of formula (I).

(I)

In formula (I), $R^3$ represents an electron-donating group, and n represents the number of repetitions of the content in brackets and is 0 or 1.

The electron-donating group of $R^3$ in formula (I) is an atom or an atomic group having a characteristic of donating an electron to a pyrazine ring. The electron-donating group is preferably one in which the Hanmmett $\sigma_p$ value is less than 0. The Hammett $\sigma_p$ value is obtained by quantifying influence of a substituent on the reaction rate or equilibrium of a para-substituted benzene derivative. The Hammett $\sigma_p$ value is specifically a value defined by formula (h1) or (h2).

$$\log(k/k_0) = \rho \cdot \sigma_p \quad \text{(h1)}$$

$$\log(K/K_0) = \rho \cdot \sigma_p \quad \text{(h2)}$$

k is a reaction rate constant of an unsubstituted benzene derivative, $k_0$ is a reaction rate constant of a substituted benzene derivative, K is an equilibrium constant of an unsubstituted benzene derivative, $K_0$ is an equilibrium constant of a substituted benzene derivative, and $\rho$ is a reaction constant determined depending on the reaction kind and conditions of the reaction. The detailed description of the Hammett $\sigma_p$ value and each values of substituents may be referred to "Lange's Handbook of Chemistry, the 13$^{th}$ edition" edited by J. A. Dean, 1985, pages 3-132 to 3-137, McGrow-Hill.

Examples of the electron-donating group of $R^3$ include ones having a hetero atom and a Hammett $\sigma_p$ value of less than 0. Examples of the hetero atom include a nitrogen atom, an oxygen atom, a sulfur atom, a silicon atom, and a phosphorus atom. The electron-donating group is preferably a group having a bonding to a hetero atom, or a group in which at least one hetero atom bonds to a $sp^2$ carbon atom to form a structure in which a π conjugation including the $sp^2$ carbon atom spreads to a pyrazine ring.

Examples of the group having a bonding to a hetero atom include substituted or unsubstituted diarylamino groups, substituted or unsubstituted dialkylamino groups, substituted or unsubstituted alkylarylamino groups, substituted or unsubstituted cyclic amino groups, substituted or unsubstituted aryloxy groups, substituted or unsubstituted alkyloxy groups, substituted or unsubstituted arylthio groups, substituted or unsubstituted alkylthio groups, substituted or unsubstituted triarylsily groups, substituted or unsubstituted alkyldiarylsilyl groups, substituted or unsubstituted dialkylarylsilyl groups, substituted or unsubstituted trialkylsilyl groups, substituted or unsubstituted cyclic silyl groups, substituted or unsubstituted diarylphosphino groups, substituted or unsubstituted dialkylphosphino groups, and substituted or unsubstituted cyclic phosphino groups.

Examples of the group in which at least one hetero atom bonds to a $sp^2$ carbon atom to form a structure in which a π conjugation including the $sp^2$ carbon atom spreads to a pyrazine ring include: aryl groups substituted with a group having a bonding to a heteroatom; heteroaryl groups substituted with a group having a bonding to a hetero atom; aryl groups substituted with a group having a structure in which a hetero atom is bonded to a $sp^2$ carbon atom to have a structure in which the π conjugation including the $sp^2$ carbon atom spreads to a pyrazine ring through the aryl group; heteroaryl groups substituted with a group having a structure in which a hetero atom is bonded to a $sp^2$ carbon atom to have a structure in which the π conjugation including the sp2 carbon spreads to a pyrazine ring through the heteroaryl group; alkenyl groups substituted with a group having a structure in which a hetero atom is bonded to a $sp^2$ carbon atom to have a structure in which the π conjugation including the sp2 carbon atom spreads to a pyrazine ring through the alkenyl group; and alkynyl groups substituted with a group having a structure in which a hetero atom is bonded to the $sp^2$ carbon atom to have a structure in which the π conjugation including the $sp^2$ carbon atom spreads to a pyrazine ring through the alkynyl group.

Preferable examples of the electron-donating group of $R^3$ include: groups having a bonding to a hetero atom; aryl groups substituted with a group having a bonding to a hetero atom; heteroaryl groups having a bonding to a hetero atom; aryl groups substituted with a group having a structure in which a hetero atom is bonded to a $sp^2$ carbon atom to have a structure in which the π conjugation including the $sp^2$ carbon atom spreads to a pyrazine ring through the aryl group; and heteroaryl groups substituted with a group having a structure in which a hetero atom is bonded to a $sp^2$ carbon atom to have a structure in which the π conjugation including the $sp^2$ carbon atom spreads to a pyrazine ring through the heteroaryl group, and more preferable examples thereof include: groups having a bonding to a hetero atom; aryl groups substituted with a group having a bonding to a hetero atom; and aryl groups substituted with a group having a structure in which a hetero atom is bonded to a $sp^2$ carbon atom to have a structure in which the π conjugation including the $sp^2$ carbon atom spreads to a pyrazine ring through the aryl group.

An aryl group as a constituent element of the electron-donating group may be monocyclic or polycyclic. Remaining rings may be any of saturated rings, unsaturated rings, and aromatic rings, provided that at least one ring of a polycyclic aryl group is an aromatic ring. The number of carbon atoms constituting an unsubstituted aryl group is preferably 6 to 40, more preferably 6 to 20, and even more preferably 6 to 14.

Examples of the unsubstituted aryl group include a phenyl group, a 1-naphthyl group, a 2-naphthyl group, an azulenyl group, an indanyl group, and a tetranyl group.

Examples of the substituted aryl group include a 4-fluorophenyl group, a 4-chlorophenyl group, a 2,4-dichlorophenyl group, a 3,4-dichlorophenyl group, a 3,5-dichlorophenyl group, a 2,6-difluorophenyl group, a 4-trifluoromethylphenyl group, a 4-methoxyphenyl group, a 3,4-dimethoxyphenyl group, a 3,4-methylenedioxyphenyl group, a 4-trifluoromethoxyphenyl group, a 4-methoxy-1-naphthyl group, a diphenylaminophenyl group, a carbazolyl phenyl group, an acridinyl phenyl group, and a phenoxazinyl phenyl group.

Among these, as the substituted aryl group, polycyclic heteroaryl groups in which at least two aromatic rings are condensed as a substituent, such as a diphenylaminophenyl group, a carbazolyl phenyl group, an acridinyl phenyl group, or a phenoxazinyl phenyl group (preferably, nitrogen-containing condensed tricyclic heteroaryl groups such as a carbazolyl group, an acridinyl group, or a phenoxazinyl group) or aryl groups having a diarylamino group are preferable, and a diphenylaminophenyl group, a carbazolyl phenyl group, an acridinyl phenyl group, or a phenoxazinyl phenyl group is more preferable.

The heteroaryl group which constitutes an electron-donating group may be monocyclic or polycyclic. Remaining groups of a polycyclic heteroaryl group may be any of saturated rings, unsaturated rings and aromatic rings, provided that at least one ring thereof is a heteroaromatic ring. The number of atoms constituting the unsubstituted heteroaryl group is preferably 5 to 40, more preferably 5 to 20, and even more preferably 5 to 14.

Examples of the unsubstituted heteroaryl group include: 5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazoly group, an oxadiazoly group, a thiadiazoly group, and a tetrazolyl group; 6-membered heteroaryl groups such as a pyridyl group, a pyrazinyl group, a pyrimidinyl group, a pyridazinyl group, and a triazinyl group; and 7- to 40-membered heteroaryl groups such as polycyclic heteroaryl groups in which at least two aromatic rings are condensed, such as an indolyl group, a benzofuryl group, a benzothienyl group, a benzoimidazolyl group, a benzoxazolyl group, a benzothiazolyl group, a quinolyl group, an isoquinolyl group, a quinoxalinyl group, a carbazolyl group, an acridinyl group, and a phenoxazinyl group.

The alkenyl group which constitutes an electron-donating group has at least one double bond between carbons in a molecule thereof. Examples of the alkenyl group include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl, a 3-hexenyl, a 4-hexenyl group, and a 5-hexenyl group.

The alkynyl group which constitutes an electron-donating group has at least one triple bond between carbons in a molecule thereof. Examples of the alkynyl group include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

The electron-donating group in $R^3$ is particularly preferably at least one selected from the group consisting of groups of formula (d1) to formula (d4).

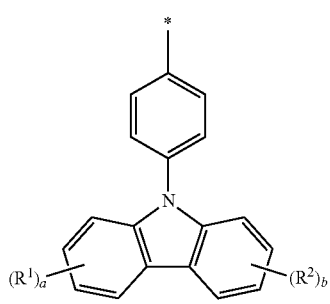

(d1)

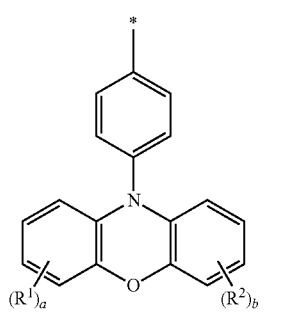

(d2)

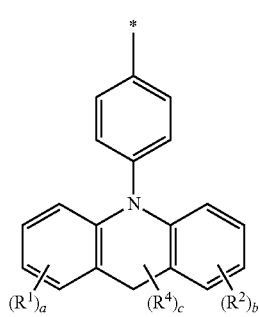

(d3)

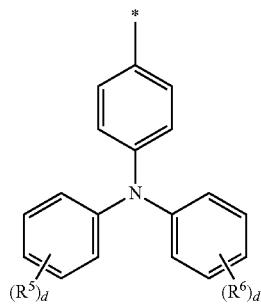

(d4)

In the formulae (d1) to (d4), $R^1$, $R^2$, $R^4$, $R^5$ and $R^6$ each independently represents a substituent, a and b each independently represents the number of $R^1$ or $R^2$ in brackets and is any one of integers of 0 to 4 (preferably 0), c represents the number of $R^4$ in brackets and is any one of integers of 0 to 2 (preferably 2), d represents the number of R or $R^6$ in brackets and is any one of integers of 0 to 5 (preferably 1), and when each of $R^1$, $R^2$, $R^4$, $R^5$ or $R^6$ is plurally substituted, the substituents may be identical to or different from each other, two adjacent substituents may bond together to form a ring with carbon atoms bonded with the substituents, and * represents a bonding position.

The phrase "when each of $R^1$, $R^2$, $R^4$, $R^5$ or $R^6$ is plurally substituted" refers to the cases where a or b represents any one of integers of 2 to 4, c represents 2, and/or d represents any one of integers of 2 to 5. For example, when a represents 2, two $R^1$ may be the same substituents, or different substituents from each other.

Next, the phrase "two adjacent substituents" refers to the combination of $R^1$ and $R^2$, that of $R^2$ and $R^4$, or that of $R^5$ and $R^6$. For example, $R^1$, $R^2$, a carbon atom bonding with $R^1$, and a carbon atom bonding with $R^2$ may form a ring together. Alternatively, when a represents 2, two $R^1$ and carbon atoms bonding with the two $R^1$ may form a ring together.

In the present invention, the term "unsubstituted" refers to a group consisting of a mother nucleus. In the case where only the name of a group serving as a mother nucleus is provided, this refers to "unsubstituted" unless specifically indicated otherwise.

On the other hand, the term "substituted" refers to any hydrogen atom of a group serving as a mother nucleus being substituted with a group having a structure that is the same as or different from the mother nucleus. Thus, a "substituent" is another group bound to a group serving as the mother nucleus. There may be one substituent or two or more substituents. Two or more substituents may be the same or different from each other.

There are no particular limitations on "substituents" provided that they are chemically available and achieve the effects of the present invention.

Typical examples of groups that can be "substituents" include the following groups:

halogeno groups such as a fluoro group, a chloro group, a bromo group, and an iodo group;

C1-20 alkyl groups (preferably C1-6 alkyl groups) such as a methyl group, an ethyl group, a n-propyl group, an i-propyl group, a n-butyl group, a s-butyl group, an i-butyl group, a t-butyl group, a n-pentyl group, and a n-hexyl group;

C2-10 alkenyl groups (preferably C2-6 alkenyl groups) such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group;

C2-10 alkynyl groups (preferably C2-6 alkynyl groups) such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group;

C3-8 cycloalkyl groups such as a cyclopropyl group, a cyclobutyl group, a cyclopentyl group, a cyclohexyl group, a cycloheptyl group, and a cubanyl group;

C3-8 cycloalkenyl groups such as a 2-cyclopropenyl group, a 2-cyclopentenyl group, a 3-cyclohexenyl group, and a 4-cyclooctenyl group;

C6-40 aryl groups (preferably C6-10 aryl groups) such as a phenyl group and a naphthyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group;

6-membered heteroaryl groups such as a pyridyl group, a pyrazinyl group, a pyrimidinyl group, a pyridazinyl group, and a triazinyl group;

condensed heteroaryl groups such as an indolyl group, a benzofuryl group, a benzothienyl group, a benzoimidazolyl group, a benzoxazolyl group, a benzothiazolyl group, a quinolyl group, an isoquinolyl group, and a quinoxalinyl group;

cyclic ether groups such as an oxiranyl group, a tetrahydrofuryl group, a dioxolanyl group, and a dioxlanyl group;

cyclicamino groups such as an aziridinyl group, a pyrrolidinyl group, a piperidyl group, a piperazinyl group, and a morpholinyl group;

a hydroxyl group; an oxo group;

C1-20 alkoxy groups (preferably C1-6 alkoxy groups) such as a methoxy group, an ethoxy group, a n-propoxy group, an i-propoxy group, a n-butoxy group, a s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group, and a propargyloxy group;

C6-10 aryloxy groups such as a phenoxy group, and a naphthoxy group;

5- to 6-membered heteroaryloxy groups such as a thiazolyloxy group, and a pyridyloxy group;

a carboxyl group;

a formyl group; C1-6 alkylcarbonyl groups such as an acetyl group, and a propionyl group;

a formyloxy group; C1-6 alkylcarbonyloxy groups such as an acetyloxy group, and a propionyloxy group;

C1-6 alkoxycarbonyl groups such as a methoxycarbonyl group, an ethoxycarbonyl group, a n-propoxycarbonyl group, an i-propoxycarbonyl group, a n-butoxycarbonyl group, and a t-butoxycarbonyl group;

C1-6 haloalkyl groups such as a chloromethyl group, a chloroethyl group, a trifluoromethyl group, a 1,2-dichloro-N-propyl group, a 1-fluoro-n-butyl group, and a perfluoro-n-pentyl group;

C2-6 haloalkenyl groups such as a 2-chloro-1-propenyl group, and a 2-fluoro-1-butenyl group;

C2-6 haloalkynyl groups such as a 4,4-dichloro-1-butynyl group, a 4-fluoro-1-pentynyl group, and a 5-bromo-2-pentynyl group;

C3-6 halocycloalkyl groups such as a 3,3-difluorocyclobutyl group;

C1-6 haloalkoxy groups such as a 2-chloro-n-propoxy group, a 2, 3-dichlorobutoxy group, a trifluoromethoxy group, and a 2, 2, 2-trifluoroethoxy group;

C2-6 haloalkenyloxy groups such as a 2-chloropropenyloxy group, and a 3-bromobutenyloxy group;

C1-6 haloalkylcarbonyl groups such as a chloroacetyl group, a trifluoroacetyl group, and a trichloroacetyl group;

a cyano group; a nitro group; an amino group;

C1-20 alkylamino groups (preferably C1-6 alkylamino groups) such as a methylamino group, a dimethylamino group, and a diethylamino group;

C6-40 arylamino groups (preferably C6-10 arylamino groups) such as an anilino group, and a naphthylamino group;

a formylamino group; C1-6 alkylcarbonylamino groups such as an acetylamino group, a propanoylamino group, a butyrylamino group, and an i-propylcarbonylamino group;

C1-6 alkoxycarbonylamino groups such as a methoxycarbonylamnino group, an ethoxycarbonylamino group, a n-propoxycarbonylamino group, and an i-propoxycarbonylamino group;

C1-6 alkylsulfoximino groups such as a S, S-dimethylsulfoximino group;

an aminocarbonyl group;

C1-6 alkylaminocarbonyl groups such as a methylaminocarbonyl group, a dimethylaminocarbonyl group, an ethylanminocarbonyl group, and an i-propylamlinocarbonyl group;

imino C1-6 alkyl groups such as an iminomethyl group, a (1-imino) ethyl group, and a (1-imino)-n-propyl group;

hydroxyimino C1-6 alkyl groups such as a hydroxyiminomethyl group, a (1-hydroxyimino)ethyl group, and a (1-hydroxyimino)propyl group;

C1-6 alkoxyimino C1-6 alkyl group such as a methoxyiminomethyl group, and a (1-methoxyimino) ethyl group;

a mercapto group;

C1-20 alkylthio groups (preferably C1-6 alkylthio groups) such as a methylthio group, an ethylthio group, a n-propylthio group, an i-propylthio group, a n-butylthio group, an i-butylthio group, a s-butylthio group, and a t-butylthio group;

C1-6 haloalkylthio groups such as a trifluoromethylthio group, and a 2, 2, 2-trifluoroethylthio group;

C2-6 alkenylthio groups such as a vinylthio group, and an allylthio group;

C2-6 alkynylthio groups such as an ethynylthio group, and a propargylthio group;

C1-6 alkylsulfinyl groups such as a methylsulfinyl group, an ethylsulfinyl group, and a t-butylsulfinyl group;

C1-6 haloalkylsulfinyl groups such as a trifluoromethylsulfinyl group, and a 2, 2, 2-trifluoroethylsulfinyl group;

C2-6 alkenylsulfinyl groups such as an allylsulfinyl group;

C2-6 alkynylsulfinyl groups such as a propargylsulfinyl group;

C1-6 alkylsulfonyl groups such as a methylsulfonyl group, an ethylsulfonyl group, and a t-butylsulfonyl group;

C1-6 haloalkylsulfonyl groups such as a trifluoromethylsulfonyl group, and a 2, 2, 2-trifluoroethylsulfonyl group;

C2-6 alkenylsulfonyl groups such as an allylsulfonyl group;

C2-6 alkynylsulfonyl groups such as a propargylsulfonyl group;

C2-20 alkylamide groups such as an acetamide group, a N-methylamide group, a N-ethylamide group, a N-(n-propyl)amide group, a N-(n-butyl)amide group, a N-isobutyl amide group, a N-(sec-butylamide) group, a N-(t-butyl) amide group, a N, N-dimethylamide group, a N, N-diethylamide group, a N, N-di(n-propyl)amide group, a N, N-di(n-butyl)amide group, a N, N-diisobutylamide group, a N-methylacetamide group, a N-ethylacetamide group, a N-(n-propyl)acetamide group, a N-(n-butyl)acetamido group, a N-isobutylacetanmide group, a N-(sec-butyl)acetamide group, a N-(t-butyl)acetamido group, N, N-dimethylacetamide group, N, N-diethylacetamide group, N, N-di(n-propyl) acetamide group, a N, N-di(n-butyl)acetamido group, N, N-diisobutylacetamide group;

C6-20 arylanide groups such as a phenylamide group, a naphthylamide group, a phenyl acetamide group, and a naphthyl acetamide group;

tri-C1-10 alkylsilyl groups (preferably tri-C1-6 alkylsilyl groups) such as a trimethylsilyl group, a triethylsilyl group, and a t-butyldimethylsilyl group; and tri-C6-10 arylsilyl groups such as a triphenylsilyl group.

In addition, any hydrogen atoms in these "substituents" may also be substituted with other "substituents" having different structures.

The term "C1-6", for example, indicates that the number of carbon atoms of the group serving as the mother nucleus is 1 to 6. The number of carbon atoms does not include the number of carbon atoms present in substituents. For example, an ethoxybutyl group is classified as a C2 alkoxy C4 alkyl group because a butyl group serves as a mother nucleus and a substituent thereof is an ethoxy group.

As the substituent $R^1$, $R^2$, $R^4$, $R^5$ and $R^6$, a hydroxy group, a halogeno group, a C1-20 alkyl group, a C1-20 alkoxy group, a C1-20 alkylthio group, a C1-20 alkyl-substituted amino group, a C6-40 aryl-substituted amino group, a C6-40 aryl group, a 5- to 40-membered heteroaryl group, a C2-10 alkenyl group, a C2-10 alkynyl group, a C2-20 alkylamide group, a C6-20 arylamide group, or a tri C1-10 alkylsilyl group is preferable, a C1-20 alkyl group, a C1-20 alkoxy group, a C1-20 alkylthio group, a C1-20 alkyl-substituted amino group, a C6-40 aryl-substituted amino group, a C6-40 aryl group, or a 5- to 40-membered heteroaryl group is more preferable, and a C1-6 alkyl group is even more preferable.

Examples of the ring formed by binding two adjacent substituents include a benzene ring, a naphthalene ring, a pyridine ring, a pyridazine ring, a pyrimidine ring, a pyrazine ring, a pyrrole ring, an imidazole ring, a pyrazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring, and a cycloheptene ring.

Specific examples of dicyano N-heterocyclic compounds according to the present invention include the compounds below. However, these are merely illustrative, and the present invention is not limited to these exemplified compounds (I-1) to (I-8).

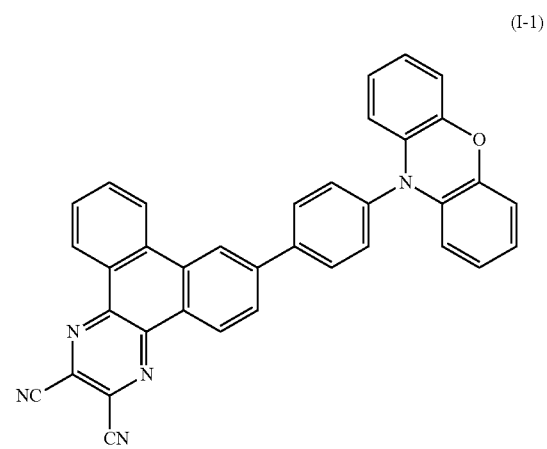

(I-1)

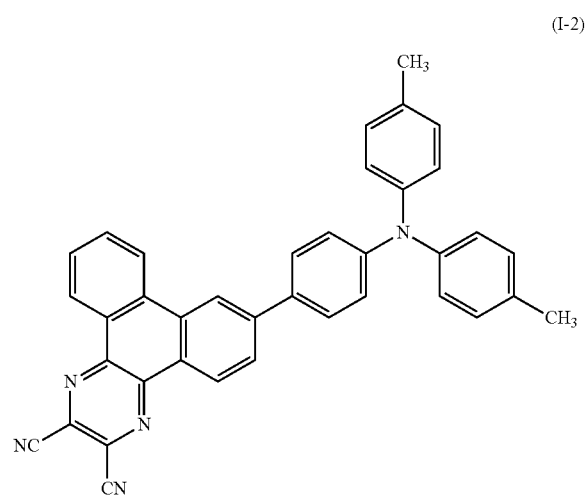

(I-2)

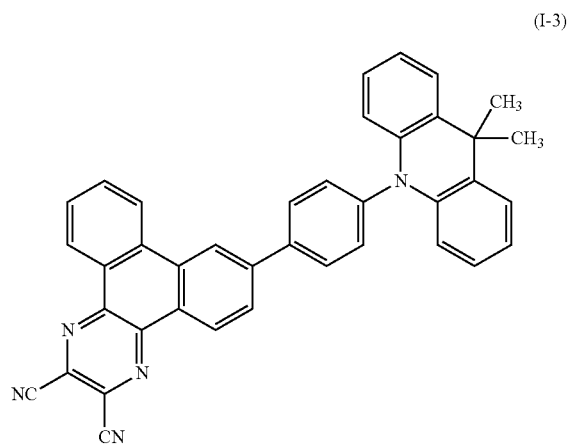

(I-3)

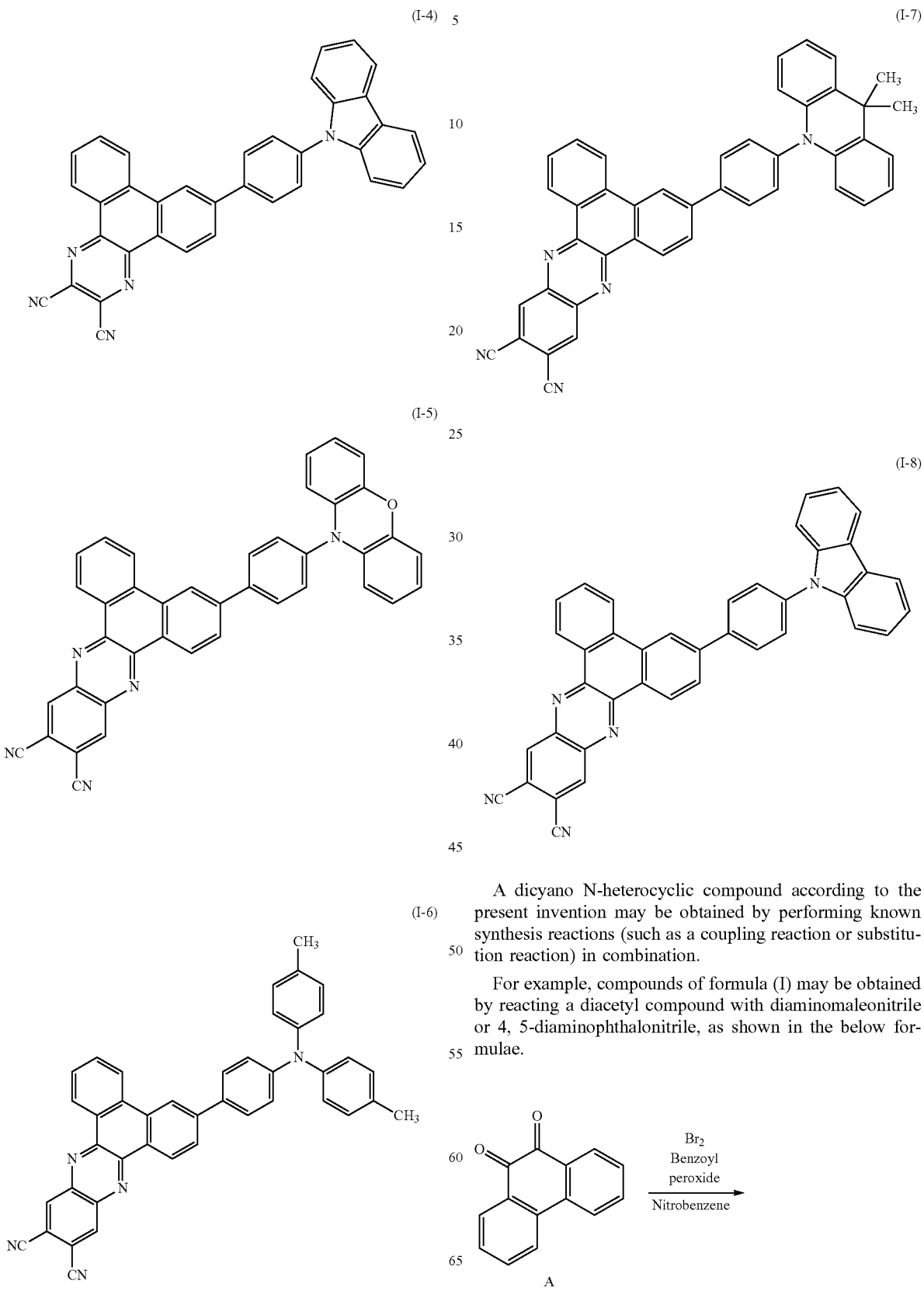

A dicyano N-heterocyclic compound according to the present invention may be obtained by performing known synthesis reactions (such as a coupling reaction or substitution reaction) in combination.

For example, compounds of formula (I) may be obtained by reacting a diacetyl compound with diaminomaleonitrile or 4, 5-diaminophthalonitrile, as shown in the below formulae.

19
-continued
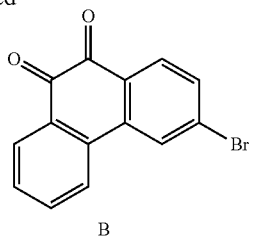
B
A compound A is reacted with nitrobenzene, benzoyl peroxide, and bromine to obtain a compound B.
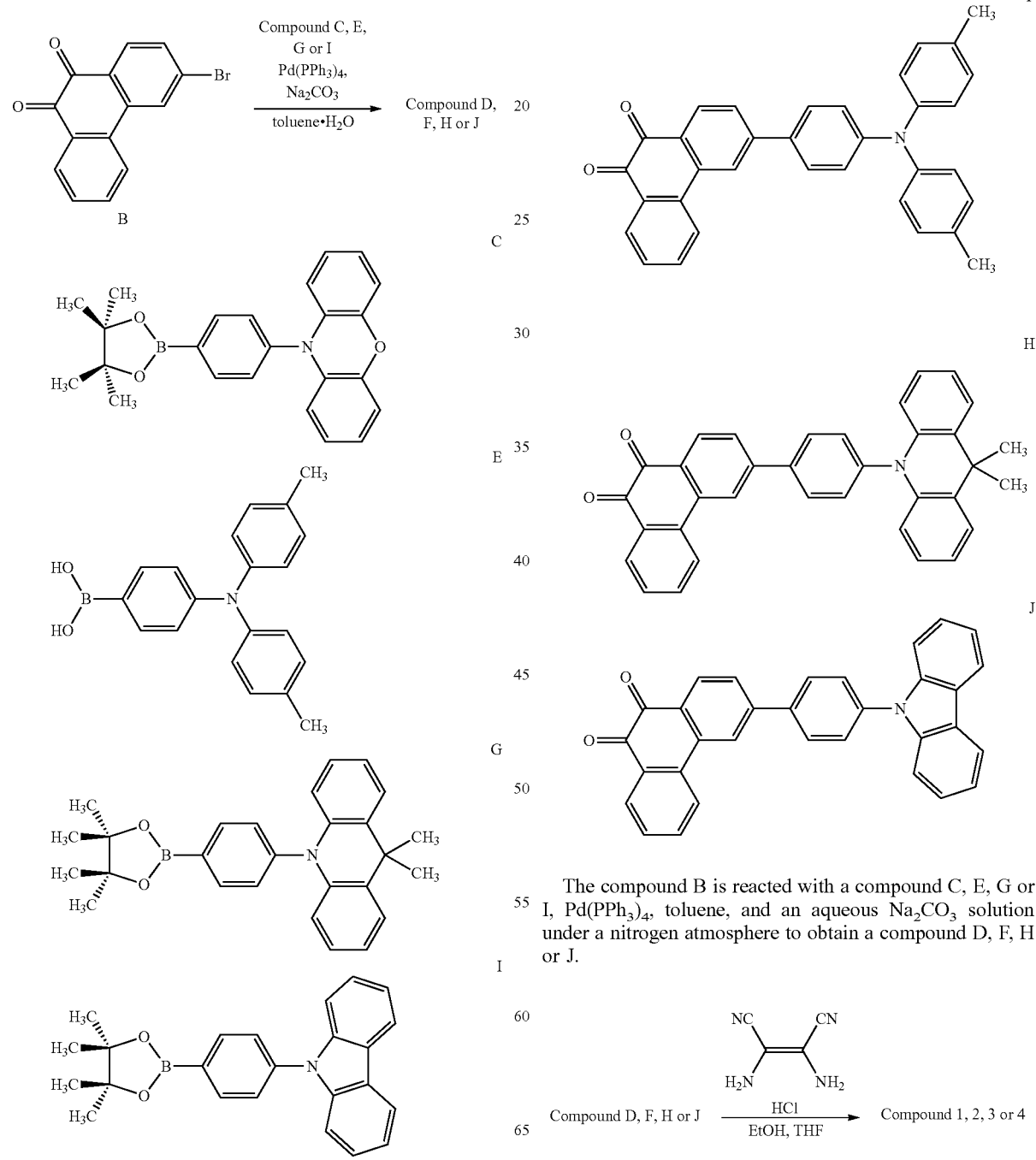
20
-continued
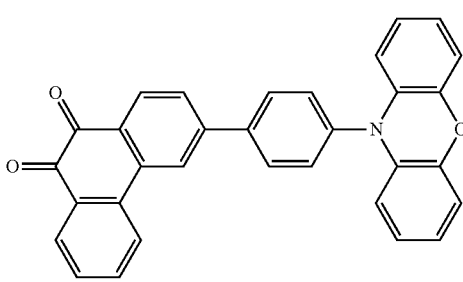
The compound B is reacted with a compound C, E, G or I, Pd(PPh$_3$)$_4$, toluene, and an aqueous Na$_2$CO$_3$ solution under a nitrogen atmosphere to obtain a compound D, F, H or J.

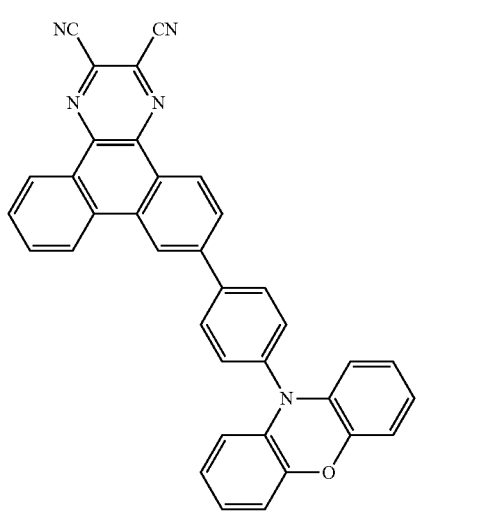
1
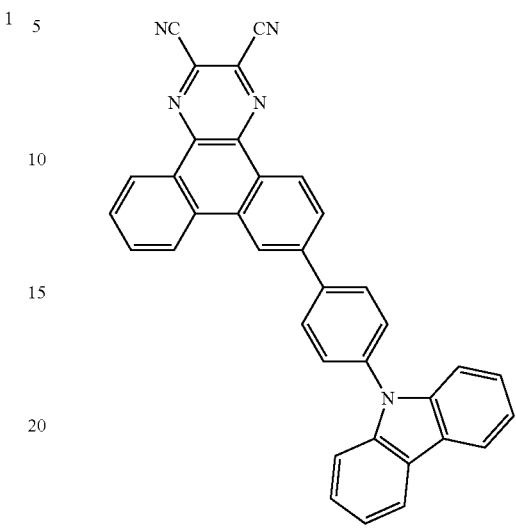
4
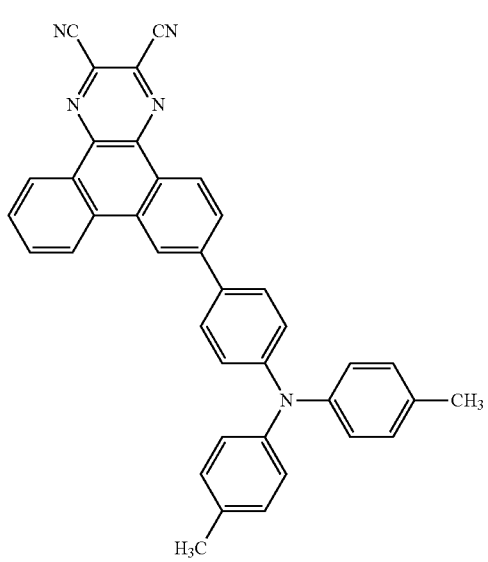
2
The compound D, F, H, or J is reacted with diaminomaleonitrile, ethanol, THF (tetrahydrofuran), and hydrochloric acid to obtain a compound 1, 2, 3, or 4.
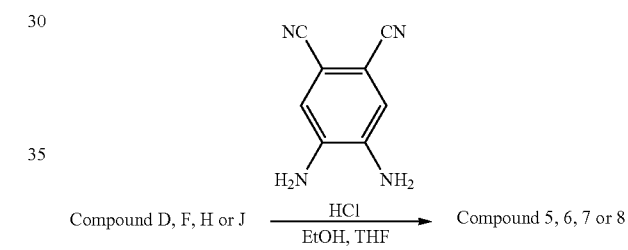
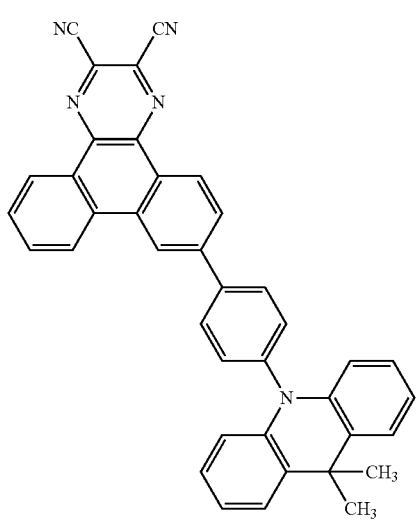
3
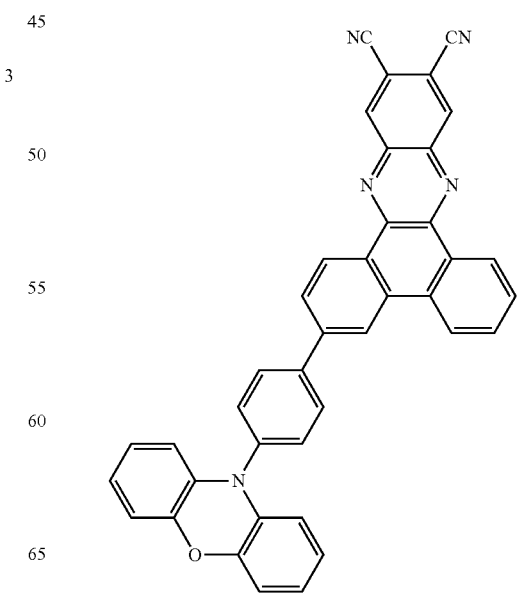
5

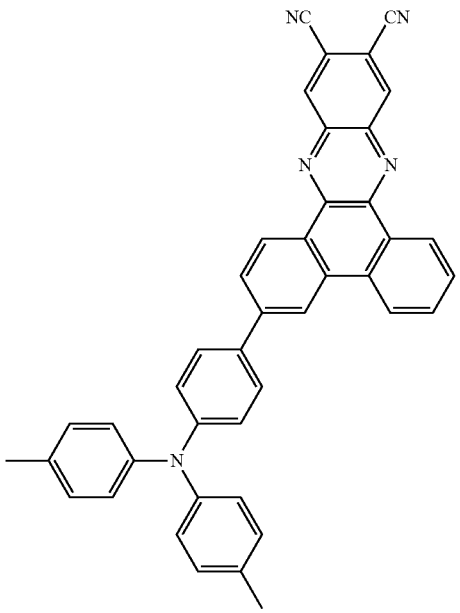

5

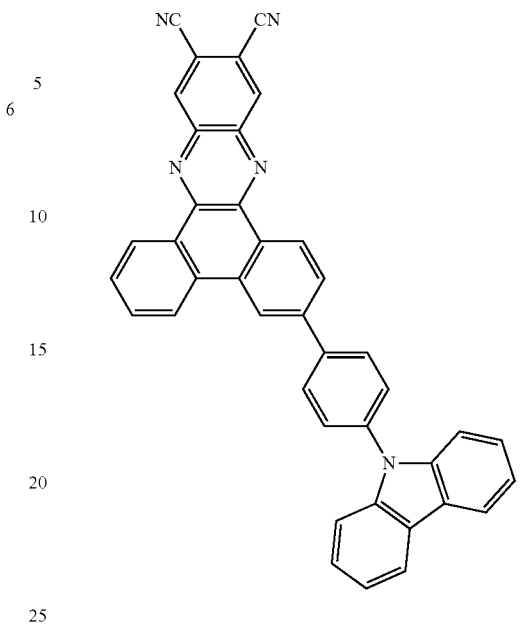

6

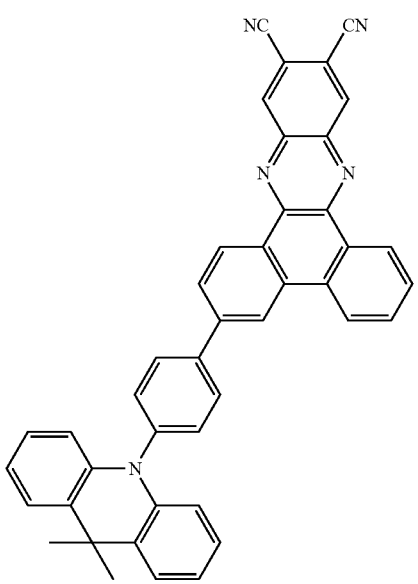

7

8

The compound D, F, H, or J is reacted with 4,5-diaminophthalonitrile, ethanol, THF, and hydrochloric acid at about 40° C. to obtain a compound 5, 6, 7, or 8.

Purification of synthesized compounds may be carried out by purification using column chromatography, adsorption purification using silica gel, activated carbon, activated clay, or the like, or recrystallization or crystallization using a solvent. Compound identification may be performed by NMR analysis or the like.

The compounds according to the present invention may be used as a light-emitting material. The light-emitting material according to the present invention can provide a light-emitting element such as an organic photoluminescence element or an organic electroluminescence element. The compound according to the present invention has a function of assisting the emission of another light-emitting material (host material), and therefore the compound may be doped with other light-emitting materials.

The organic photoluminescent element according to the present invention is formed by providing a light-emitting layer containing a light-emitting material according to the present invention on a substrate. The light-emitting layer may be formed by conducting a coating method such as spin coating, a printing method such as an ink-jet printing method, a vapor deposition method, or the like.

The organic electroluminescent element according to the present invention is formed by providing organic layers between an anode and a cathode. The term "organic layers" in the present invention refers to layers located between an anode and a cathode, the layers being substantially composed of organic substances, and the layers may include inorganic substances provided that the performance of the light-emitting element according to the present invention is not impaired.

The structure of one embodiment of an organic electroluminescent element according to the present invention is composed of a substrate, an anode, a hole injection layer, a hole transport layer, an electron-blocking layer, a light-emitting layer, a hole-blocking layer, an electron-transporting layer, and a cathode, which are provided in this order, and an electron injection layer may be further provided between the electron-transporting layer and the cathode. In the multilayered structure, it is possible to omit some of the organic layers, and, for example, an anode, a hole transport layer, a light-emitting layer, an electron-transporting layer, an electron injection layer, and a cathode may be provided on a substrate in this order, alternatively, or an anode, a hole transport layer, a light-emitting layer, an electron-transporting layer, and a cathode may be provided on a substrate in this order. The light-emitting material according to the present invention may be doped not only in a light-light-emitting layer, but also in a hole injection layer, a hole transport layer, an electron-blocking layer, a hole-blocking layer, an electron-transporting layer, or an electron injection layer.

The substrate is to be a support of the light-emitting element, and a silicon plate, a quartz plate, a glass plate, a metal plate, a metal foil, a resin film, or a resin sheet is used. In particular, a glass plate, or a transparent plate of synthetic resin such as polyester, polymethacrylate, polycarbonate, or polysulfone is preferred. In the case where a synthetic resin substrate is used, it is necessary to pay attention to the gas barrier property. In the case where the gas barrier property of the substrate is too low, the light-emitting element may be deteriorated by the outside air passing through the substrate. Therefore, it is preferable to ensure the gas barrier properties on either one or both sides of the synthetic resin substrate provided with a dense silicon oxide film or the like.

An anode is provided on the substrate. A material having a high work function is generally used to form the anode. Examples of the anode material include metals such as aluminum, gold, silver, nickel, palladium, and platinum; metal oxides such as indium oxide, tin oxide, ITO, zinc oxide, $In_2O_3$—ZnO, and IGZO; metal halides such as copper iodide, carbon black, and conductive polymers such as poly (3-methylthiophene), polypyrrole, and polyaniline. The anode is usually formed using a sputtering method, or a vacuum deposition method. In the case of fine particles of metal such as silver, fine particles of copper iodide, or carbon black, conductive metal oxide fine particles or conductive polymer fine powders are used, dispersed in a suitable binder resin solution, and then applied on a substrate to form an anode. Furthermore, in the case of the conductive polymer, the conductive polymer may be subjected to electrolytic polymerization to form a thin film directly on a substrate, or may be applied on a substrate to form an anode.

The anode may also be formed by laminating at least two substances different from each other. The thickness of the anode varies depending on the required transparency. When the transparency is required, the transmittance of visible light is usually at least 60%, and preferably at least 80%. In this case, the thickness is usually from 10 to 1000 nm, and preferably from 10 to 200 nm. In the case where the anode may be opaque, the thickness of the anode may be approximately the same as that of the substrate. It is preferable that the sheet resistance of the anode be at least several hundred Ω/□.

In a hole injection layer which is provided as needed, a porphyrin compound such as copper phthalocyanine, a naphthalene diamine derivative, a star-burst type triphenylamine derivative, a trimer or a tetramer of triphenylamin such as an arylamine compound having a structure in which at least three triphenylamin structures are bonded with single bonds or divalent groups free from hetero atoms in a molecule thereof, an acceptor heterocyclic compound such as hexacyano azatriphenylene or a coating type polymer material may be used. These materials may be subjected to deposition or a known method such as a spin coating method or an inkjet method to form a thin film.

It is preferable that the hole transpot material used in the hole transport layer provided as needed exhibit a high hole injection efficiency from an anode and realize transportation of the injected holes efficiently. For this purpose, a small ionization potential, high transparency to visible light, high hole mobility, excellent stability, and suppressed generation of impurities which become trapped during manufacture or use are preferable. Besides the aforementioned general requirements, when application to a vehicle display is intended, it is further preferable that the heat resistance of the element be high. Therefore, a material having a value of 70° C. or more as Tg is desirable.

As the hole transport layer which is provided as needed, triazole derivatives, oxadiazole derivatives, imidazole derivatives, carbazole derivatives, indolocarbazole derivatives, polyarylalkane derivatives, pyrazoline derivatives, pyrazolone derivatives, phenylenediamine derivatives, arylamine derivatives, amino-substituted chalcone derivatives, oxazole derivatives, styryl anthracene derivatives, fluorenone derivatives, hydrazone derivatives, stilbene derivatives, silazane derivatives, aniline copolymers, and electroconductive oligomer or the like may be used. More specifically, compounds containing a m-carbazolylphenyl group, benzidine derivatives such as N, N'-diphenyl-N, N'-di(m-tolyl)-benzidine (hereinafter abbreviated as TPD), N, N'-diphenyl-N, N'-di(α-naphthyl)-benzidine (hereinafter abbreviated as NPD), N, N, N', N'-tetrabiphenylbenzidine, 1,1-bis[(di-4-tolylamino)phenyl]cyclohexane (hereinafter abbreviated as TAPC), various triphenylamine trimers or tetramers, or carbazole derivatives may be used. One kind of these may be used, or at least two kinds thereof may be used in combination. The hole transport layer may be a film of a single layer structure, or may be a film of a laminated structure. Further, in the hole injection or transport layer, a coating type polymer material such as poly(3,4-ethylenedioxythiophene) (hereinafter abbreviated as PEDOT)/poly (styrenesulfonate) (hereinafter, abbreviated as PSS) may be used. These materials may be subjected to deposition or another known method such as a spin coating method or an inkjet method to form a thin film.

In the hole injection layer or the hole transport layer, materials in which tris-bromophenyl amine hexachloro antimony is P-doped to materials commonly used in the layer, or polymer compounds having the structure of the PD as the partial structure thereof may be used. As the hole injection or transport host material, a carbazole derivative such as CBP, TCTA, mCP, or the like may be used.

Compounds (hi1) to (hi7) which may be preferably used as hole injection materials are shown below.

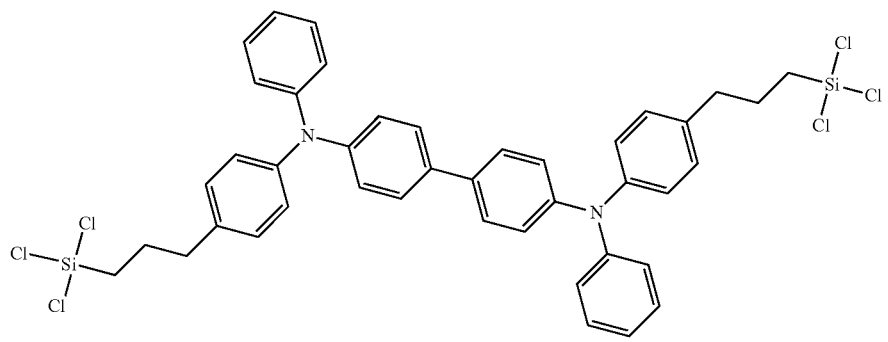
(hi1)
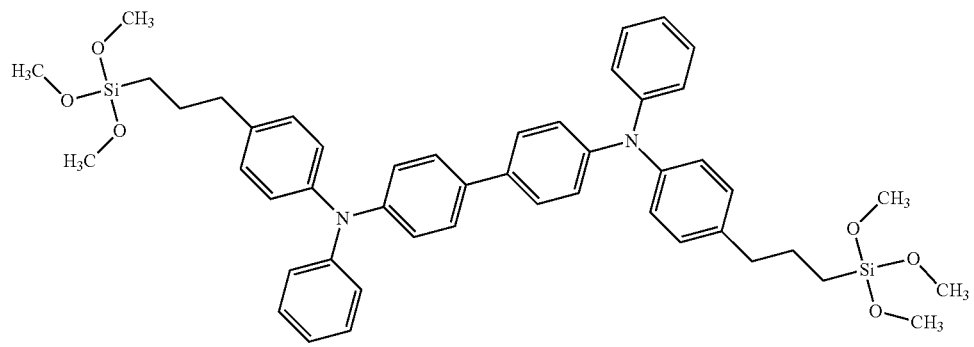
(hi2)
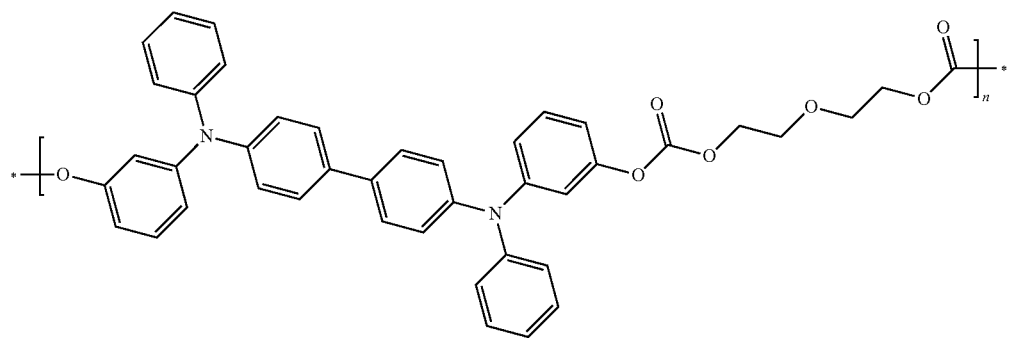
(hi3)
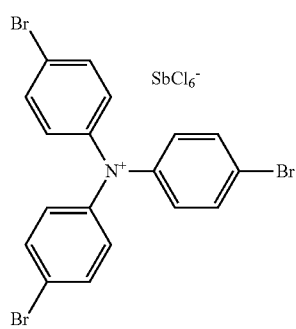
(hi4)

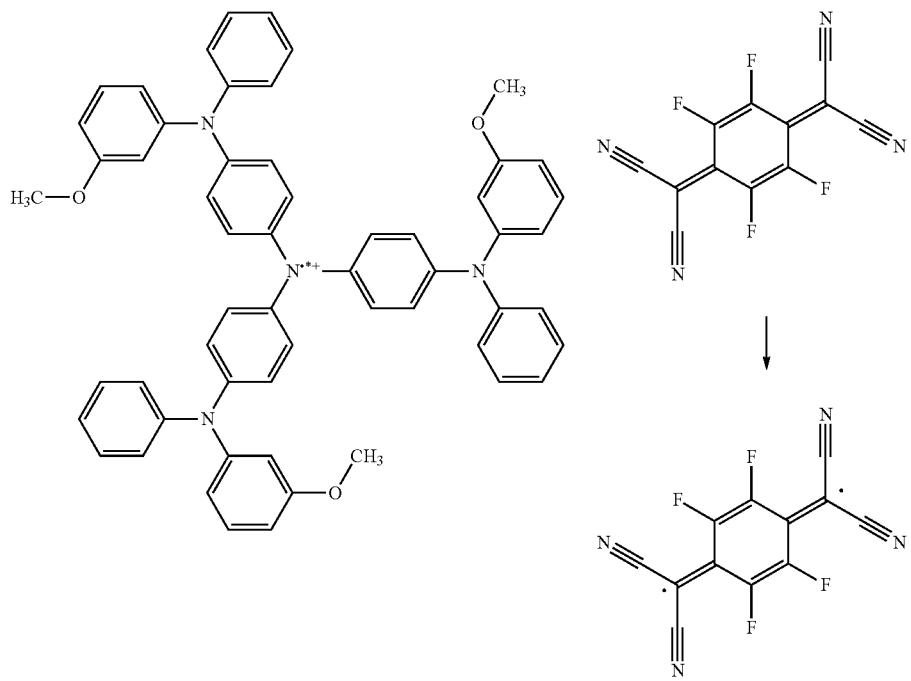
Compounds (ht1) to (ht37) which may be preferably used as hole transpot materials are shown below.
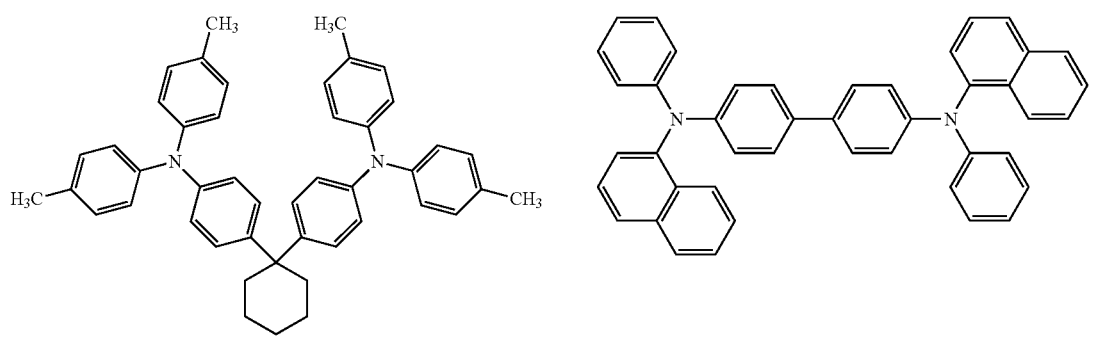

(ht3)
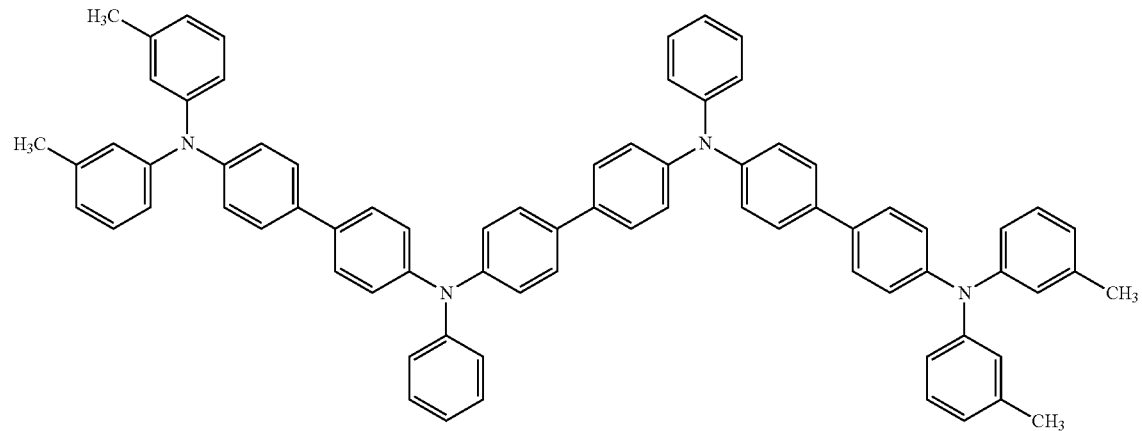
(ht4)
(ht5)
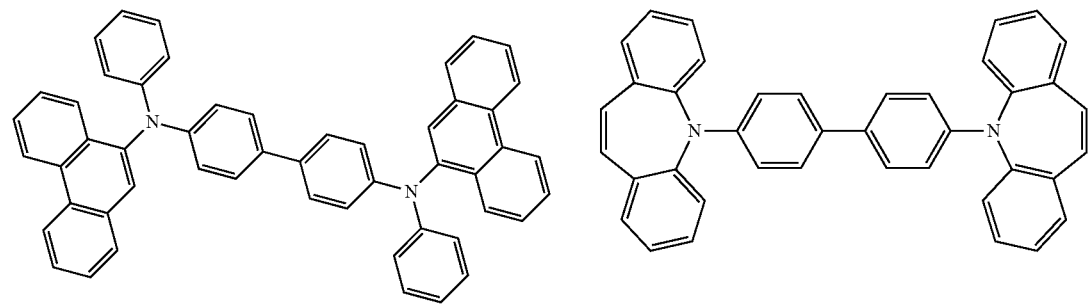
(ht6)
(ht7)
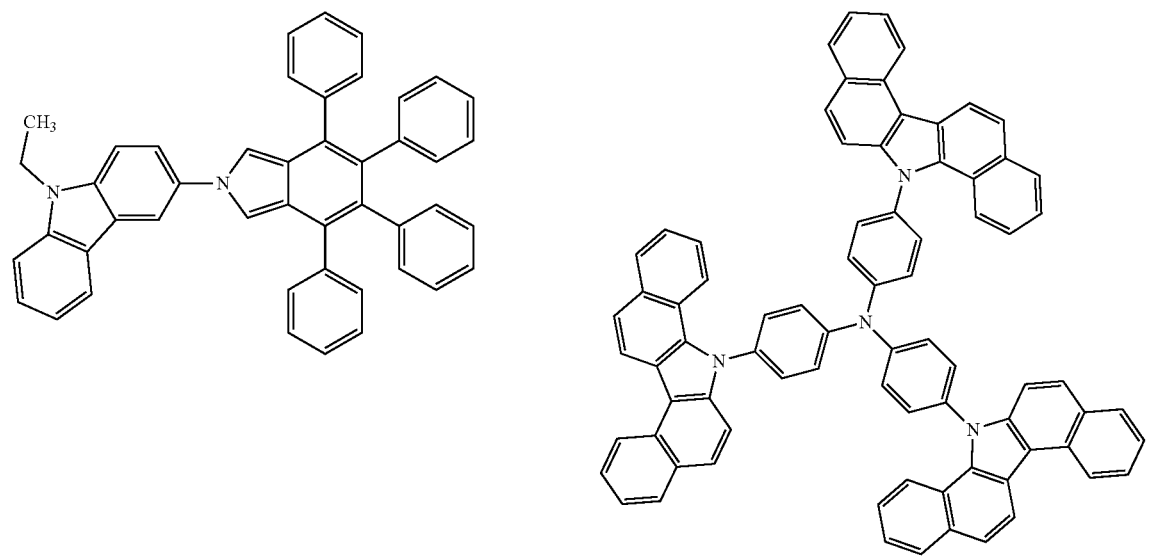

(ht8)
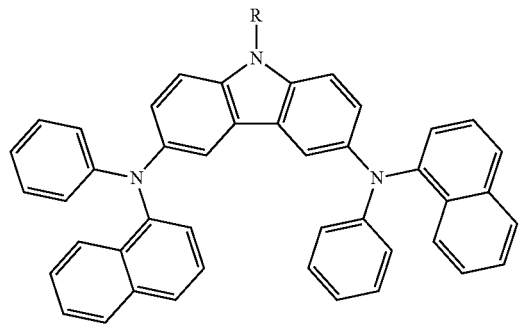
(ht9)
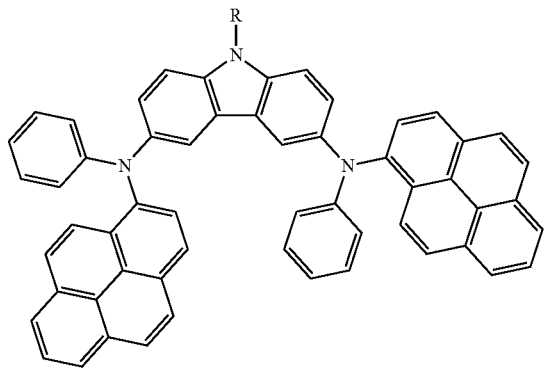
(ht10)
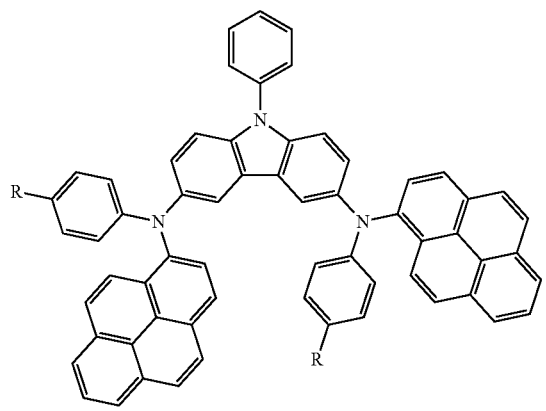
(ht11)
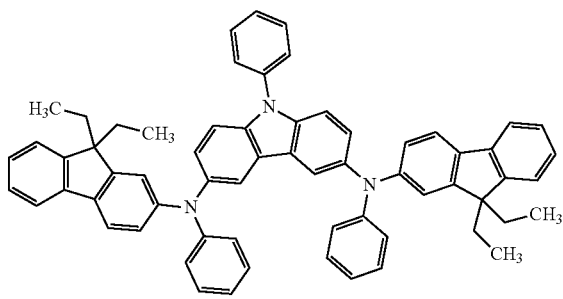
(ht12)
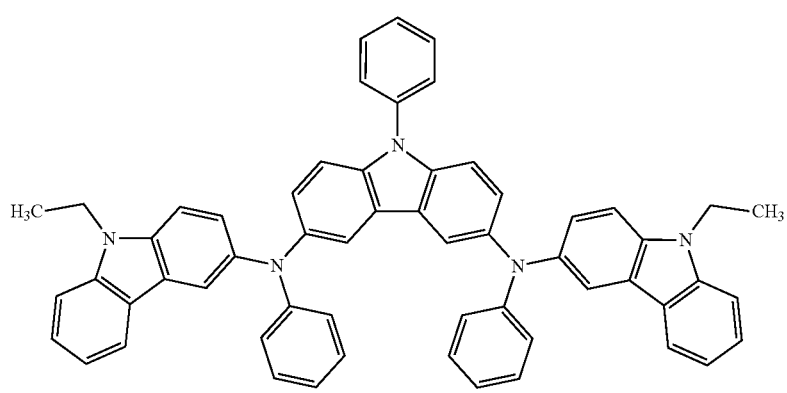

-continued
(ht13)
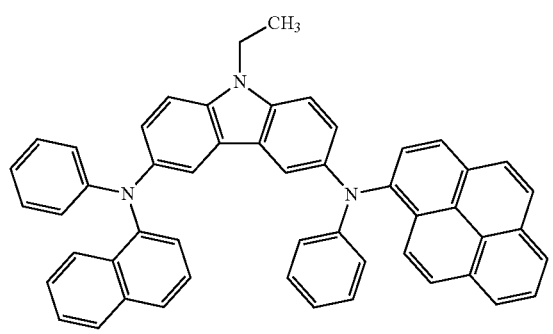
(ht14)
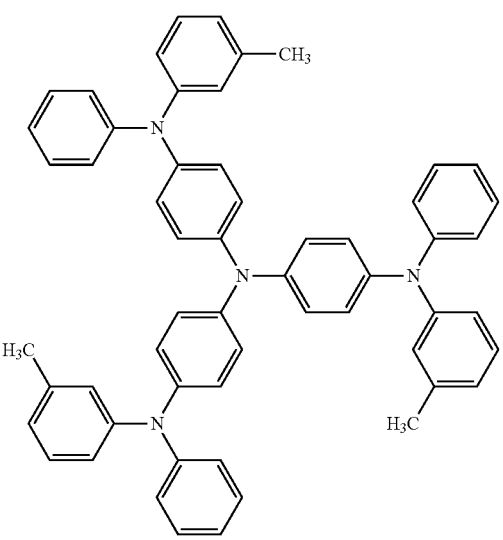
(ht15)
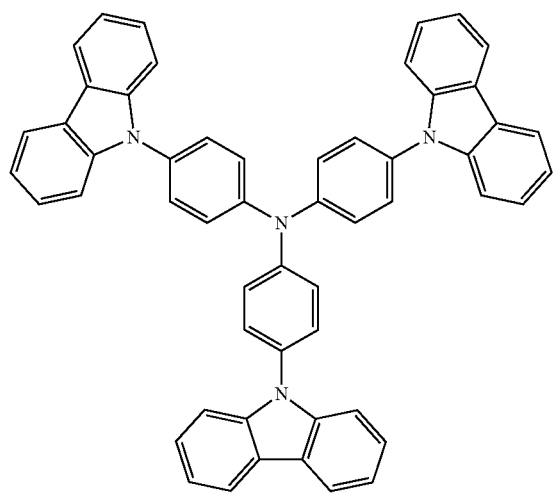
(ht16)
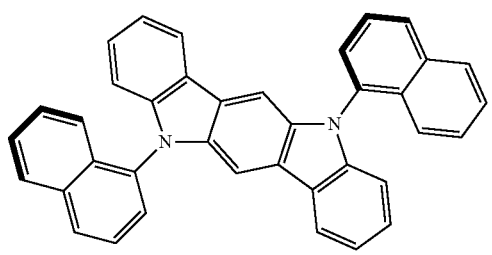
(ht17)
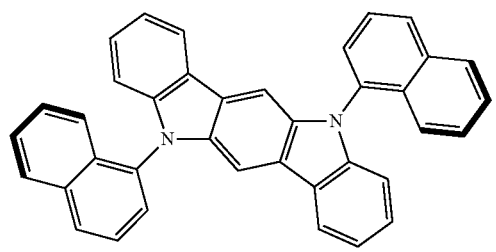
(ht18)
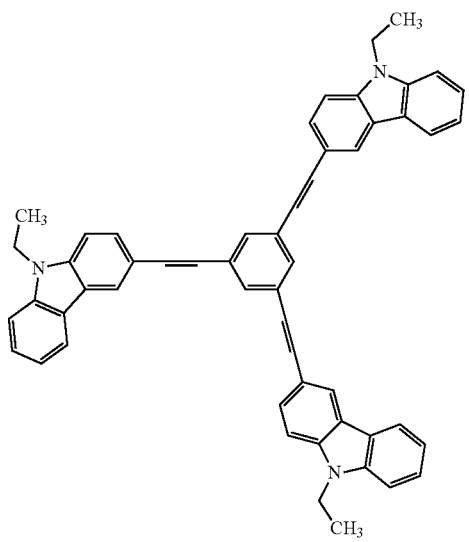

-continued
(ht19)
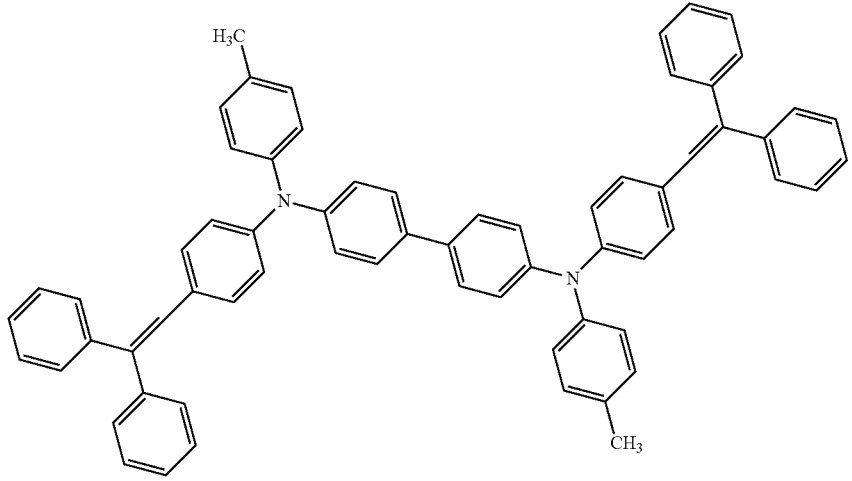
(ht20) (ht21)
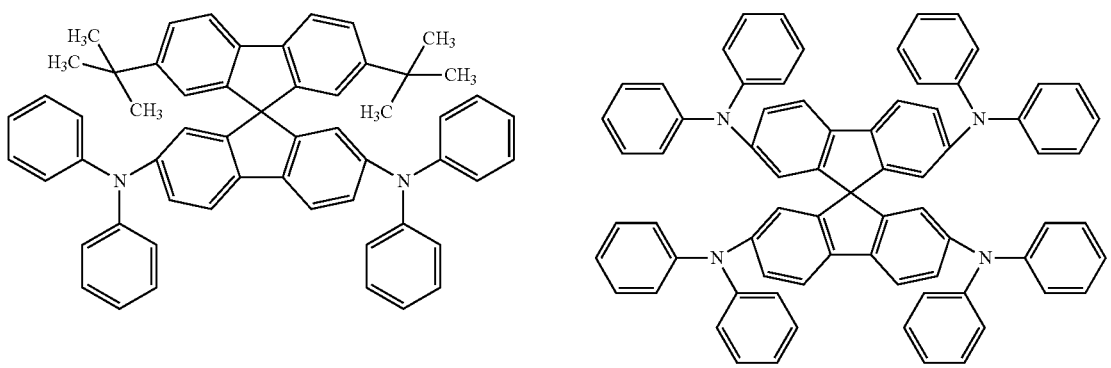
(ht22) (ht23)
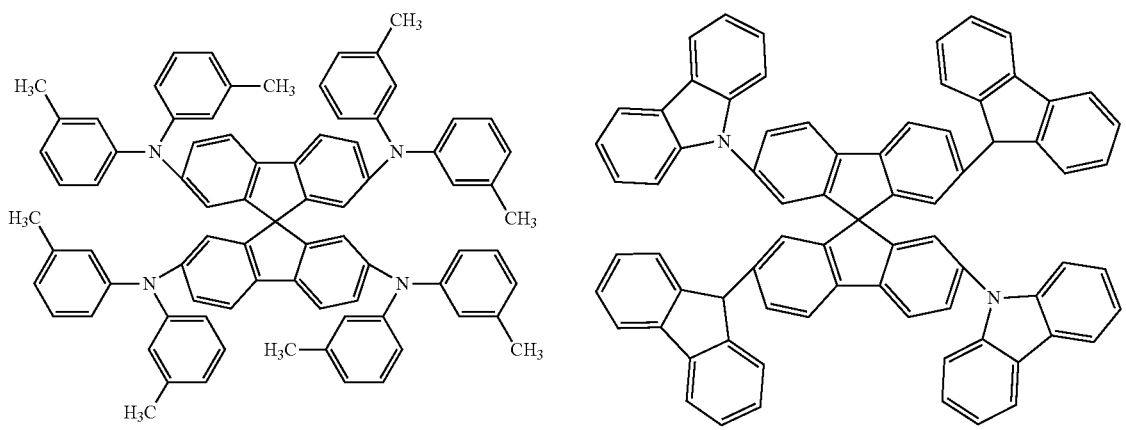
(ht24)
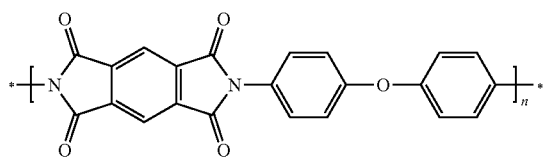
(ht25)
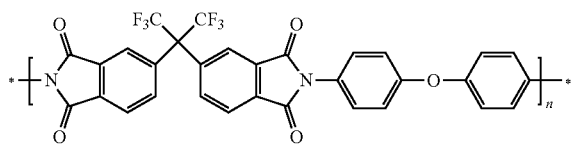

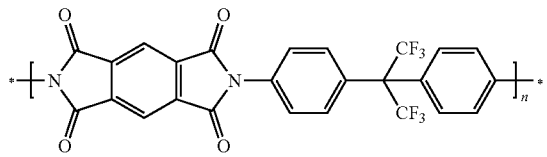
(ht26)
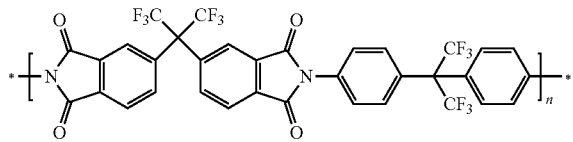
(ht27)
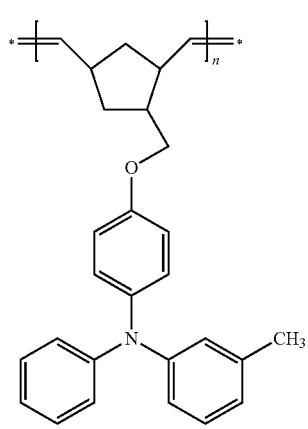
(ht28)
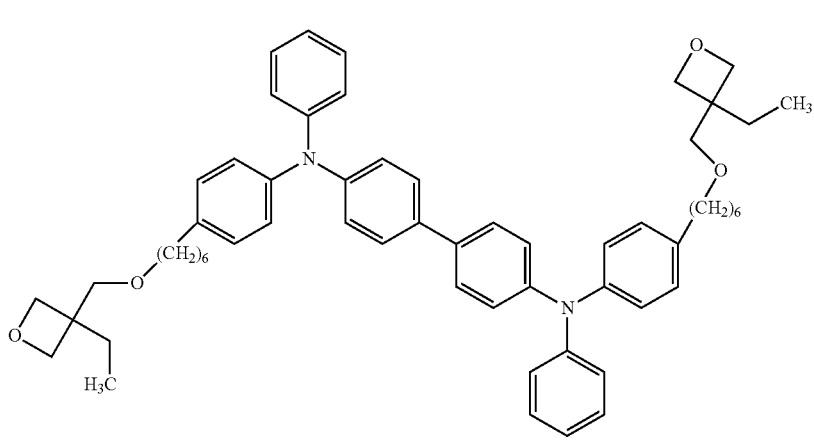
(ht29)
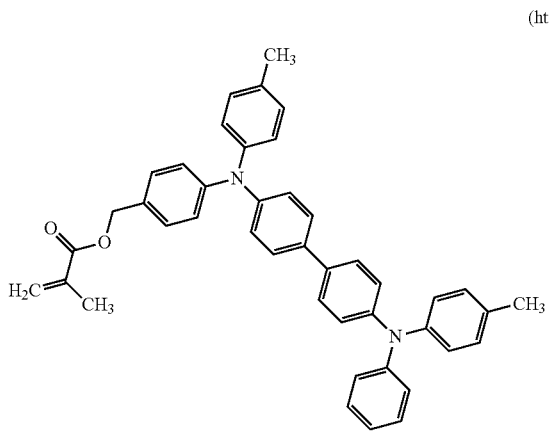
(ht30)
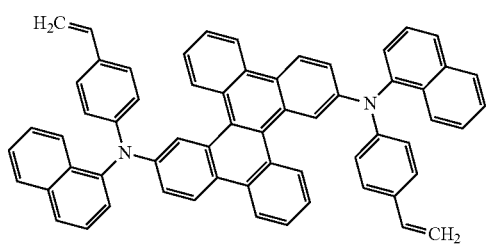
(ht31)

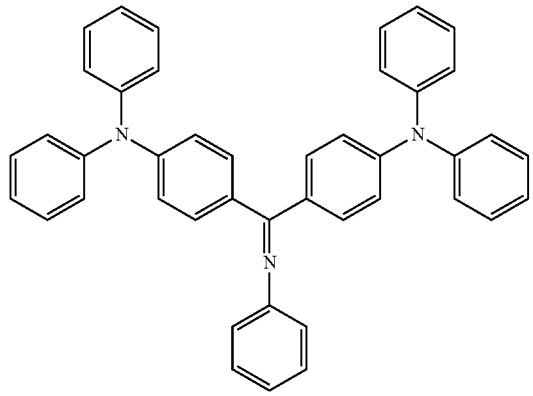
(ht32)
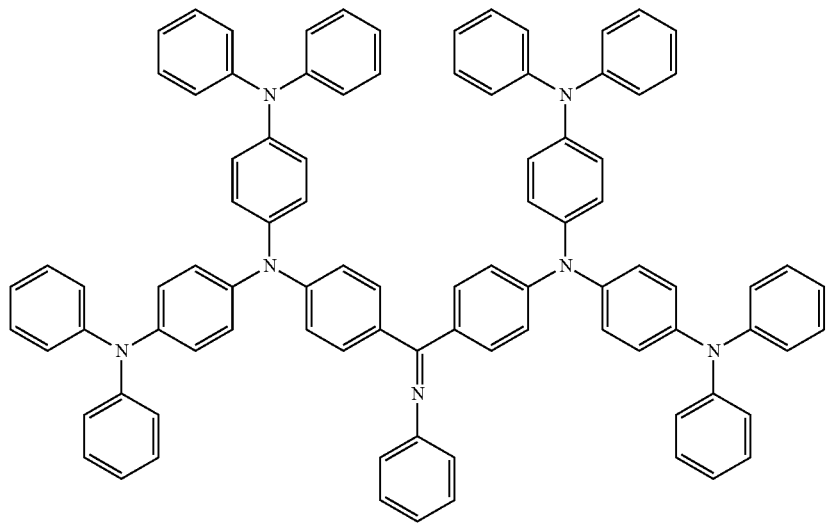
(ht33)
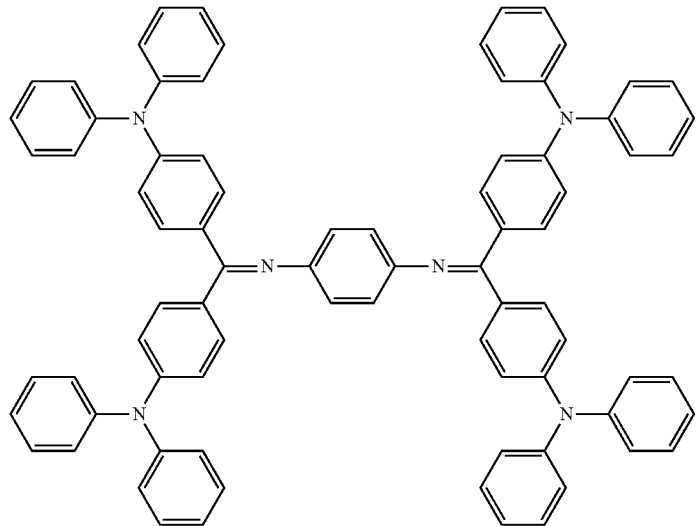
(ht34)

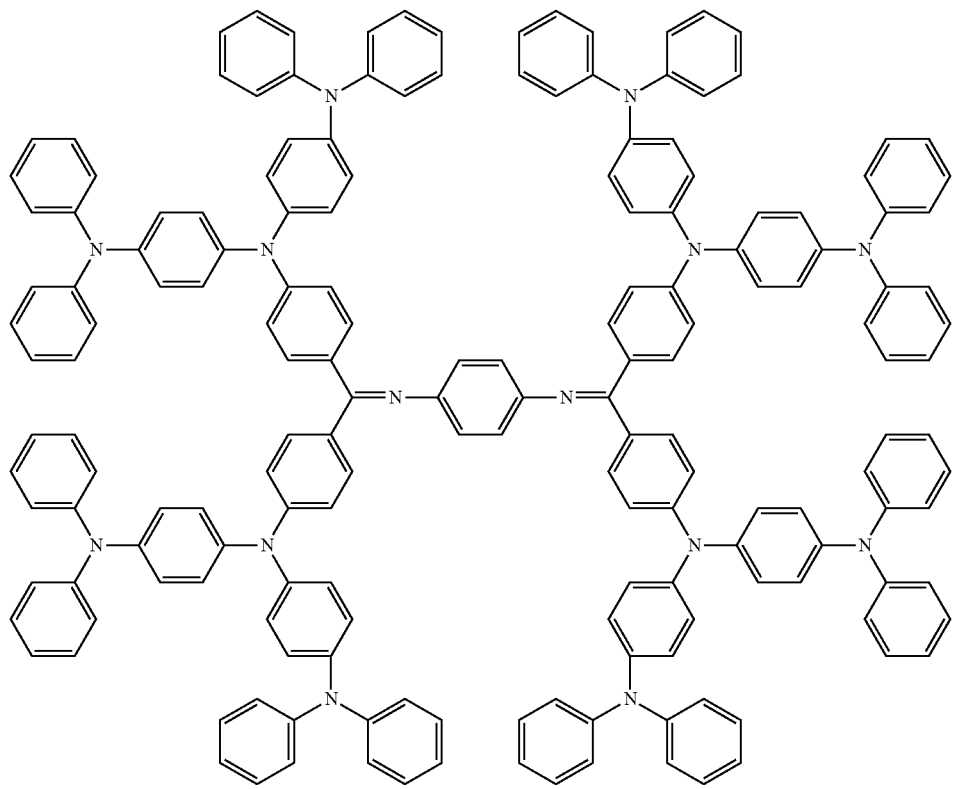

(ht35)

(ht36)

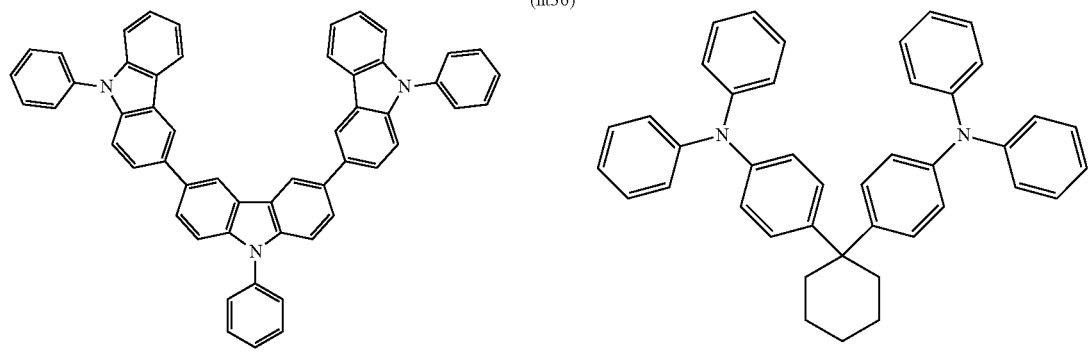

(ht37)

In an electron-blocking layer which is provided as needed, a compound having an electron blocking action, such as a carbazole derivative such as 4,4',4''-tri(N-carbazolyl) triphenylamine (hereinafter abbreviated as TCTA), 9,9-bis[4-(carbazol-9-yl) phenyl]fluorene, 1,3-bis(carbazol-9-yl) benzene (hereinafter abbreviated as mCP), or 2,2-bis(4-carbazol-9-yl-phenyl) adamantane (hereinafter, abbreviated as Ad-Cz), or a compound having a triphenylsilyl group and a triarylamine structure, such as 9-[4-(carbazol-9-yl) phenyl]-9-[4-(triphenylsilyl) phenyl]-9H-fluorene may be used. One kind of the materials may be used alone or at least two kinds thereof may be used in combination. The electron-blocking layer may be a film having a single layer structure, or may be a film having a laminated structure. The materials may be subjected to deposition or another known method such as a spin coating method or an inkjet method to form a thin film.

Compounds (es1) to (es5) which may be preferably used as electron-blocking materials are shown below.

(es1)

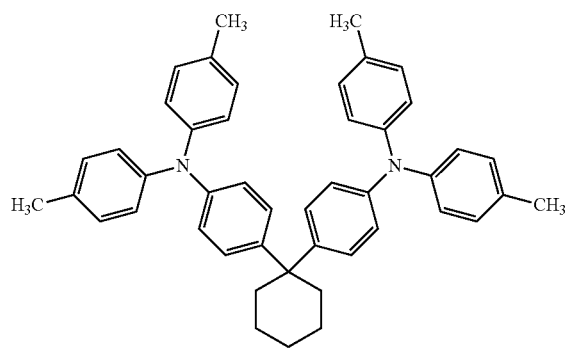

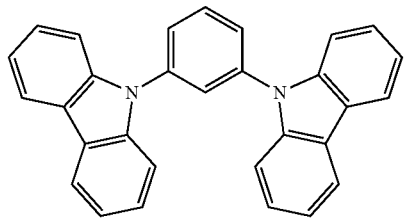
(es5)

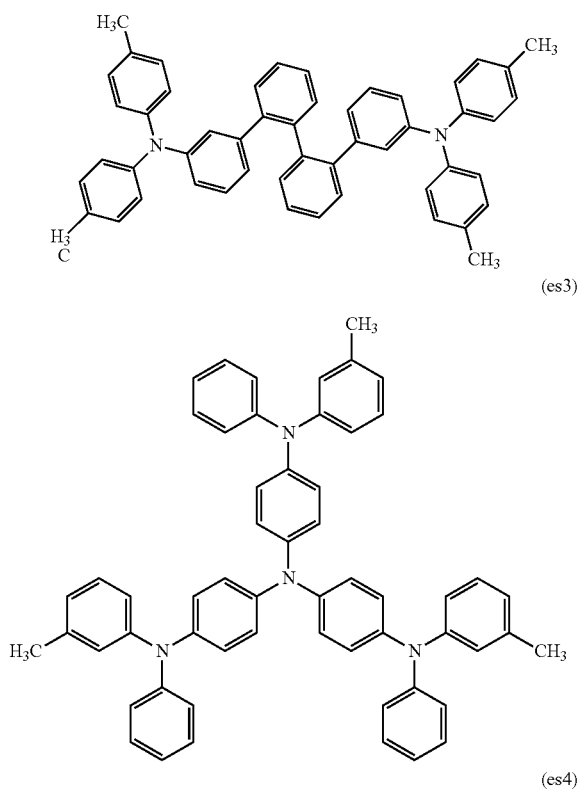
(es2)
(es3)
(es4)

A light-emitting layer is a layer which exhibits a light-emitting function by generating excitons due to recombination of holes and electrons respectively injected from an anode or a cathode. The light-emitting layer may be formed using a light-emitting material according to the invention alone, or may be formed by doping the light-emitting material according to the present invention to a host material. Examples of the host material include: metal complexes of quinolinol derivatives such as tris (8-hydroxyquinoline) aluminum (hereinafter abbreviated as Alq3); anthracene derivatives, bisstyrylbenzene derivatives, pyrene derivatives, oxazole derivatives, polyparaphenylene vinylene derivatives, compounds having a bipyridyl group and an ortho-terphenyl structure, mCP, thiazole derivatives, benzimidazole derivatives, and polydialkylfluorene derivatives. The light-emitting layer may contain a known dopant. Examples of the dopant include quinacridone, coumarin, rubrene, anthracene, perylene and derivatives thereof, benzopyran derivatives, rhodamine derivatives, and aminostyryl derivatives. A phosphorescent material such as a green phosphorescent material such as Ir(ppy)3, a blue phosphorescent material such as Flrpic, Flr6, or a red phosphorescent material such as Btp2Ir (acac) may also be used. One kind of the materials may be used alone, or at least two kinds thereof may be used in combination. The light-emitting layer may be a film of a single layer structure, or may be a film of a laminated structure. The materials may be subjected to deposition or another known method such as a spin coating method or an inkjet method to form a thin-film.

In the case where a host material is used, the lower limit of the amount of the light-emitting material according to the present invention which may be contained in the light-emitting layer is preferably 0.1% by mass and more preferably 1% by mass, and the upper limit thereof is preferably 50% by mass, more preferably 20% by mass, and more preferably 10% by mass.

Compounds (e11) to (e139) which may be preferably used as host materials in the light-emitting layer are shown below.

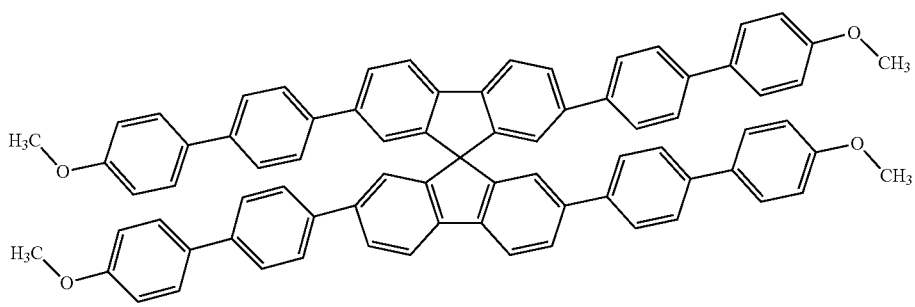
(e11)

-continued
(el2)
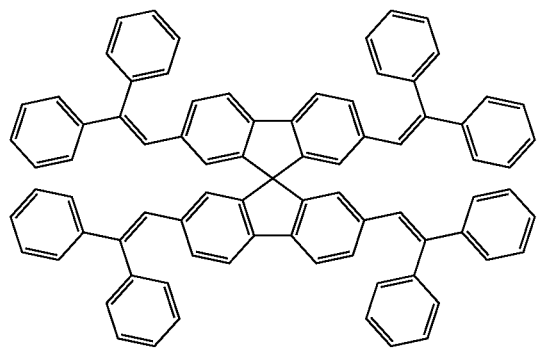
(el3)
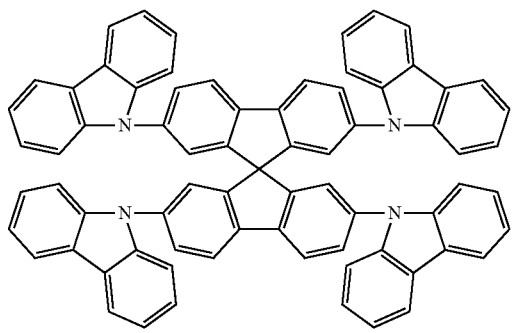
(el4)
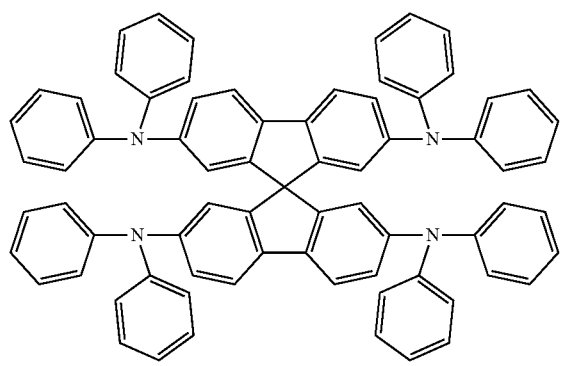
(el5)
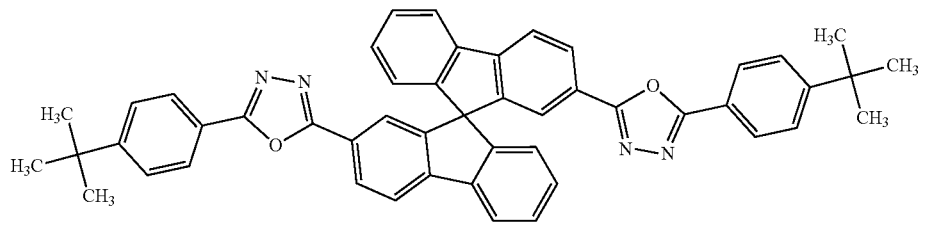
(el6)
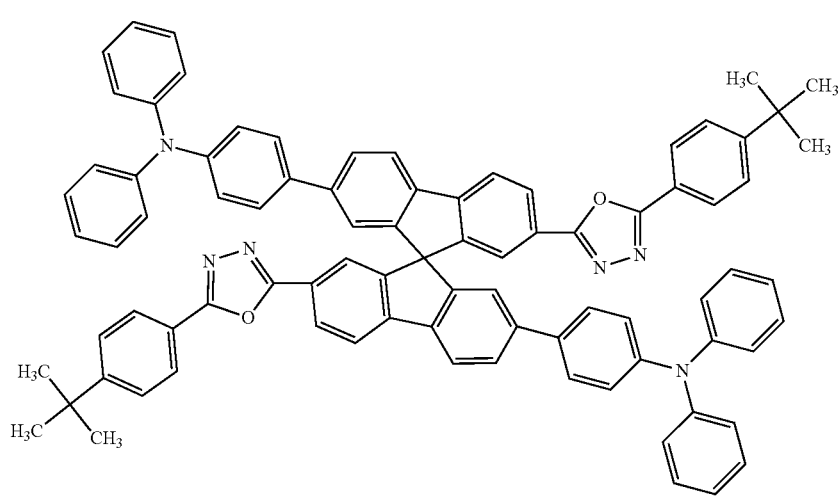

-continued
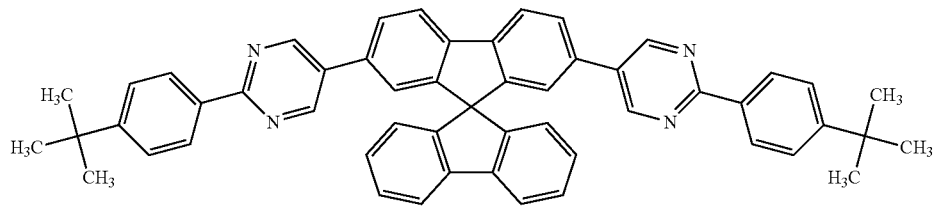
(el7)
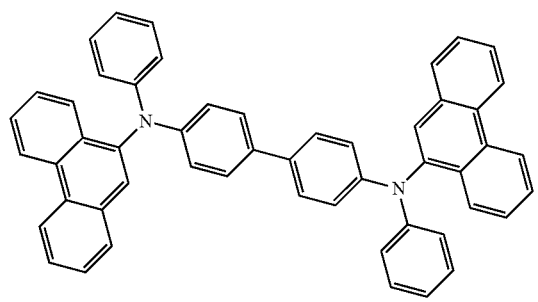
(el8)
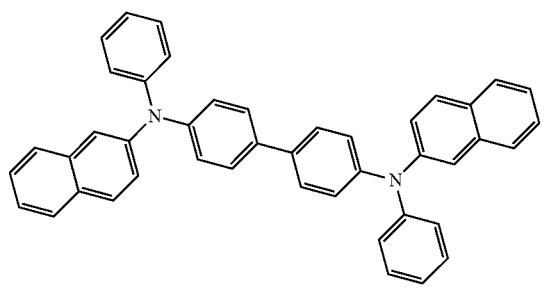
(el9)
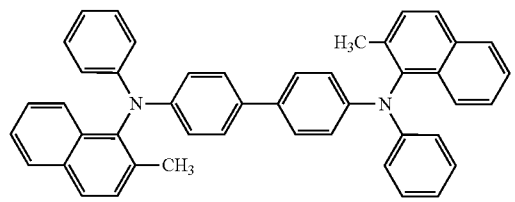
(el10)
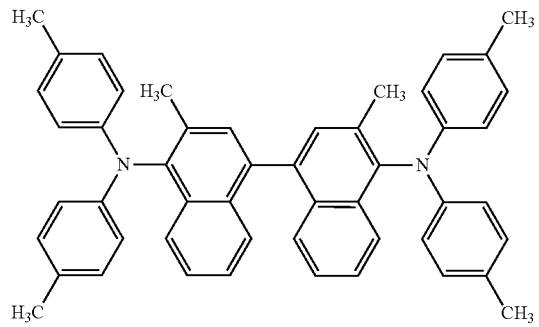
(el11)
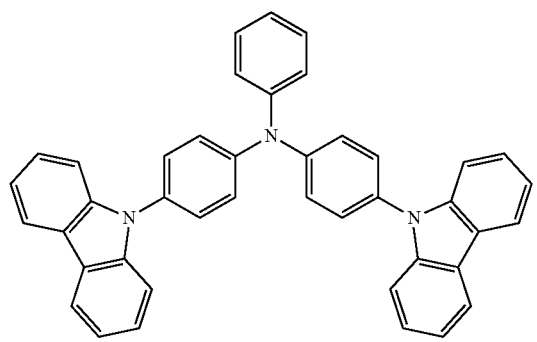
(el12)
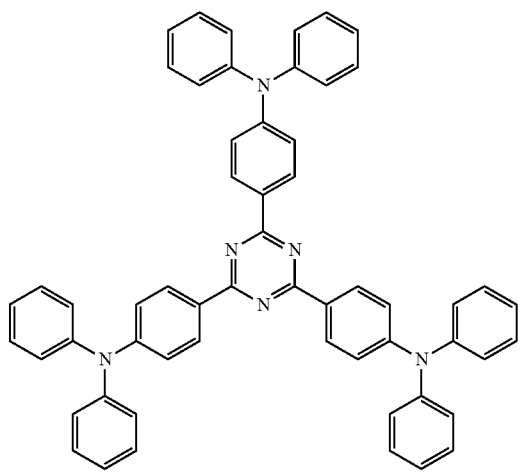
(el13)

-continued
(el14)
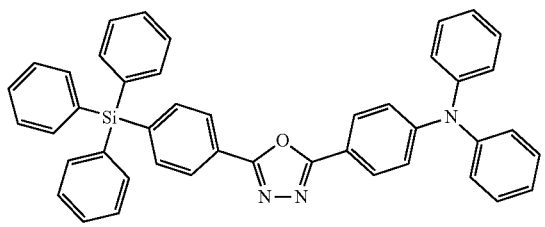
(el15)
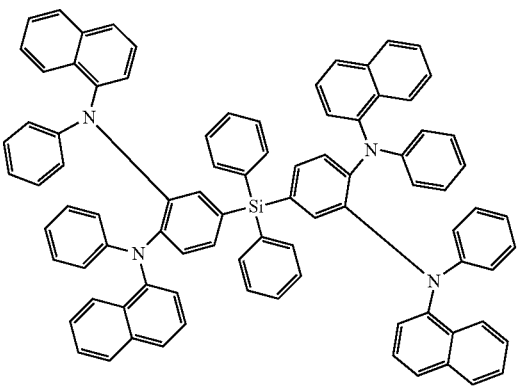
(el16)
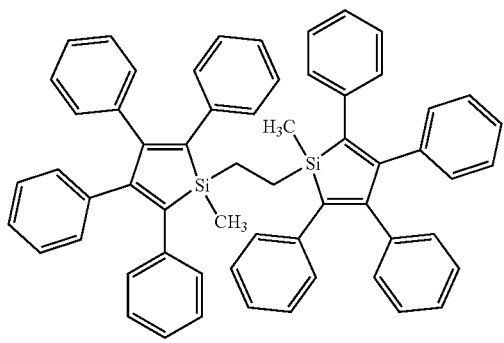
(el17)
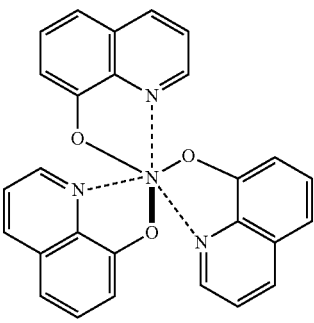
(el18)
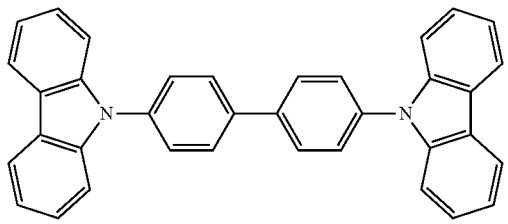
(el19)
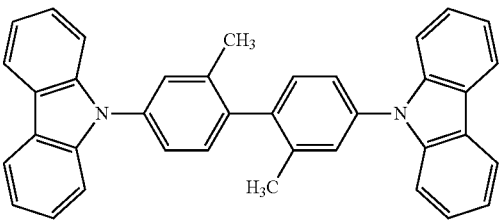
(el20)
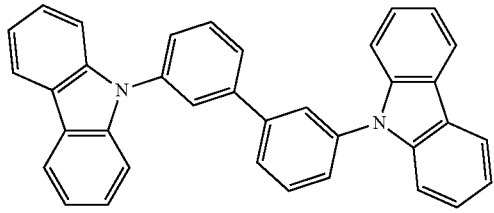
(el21)
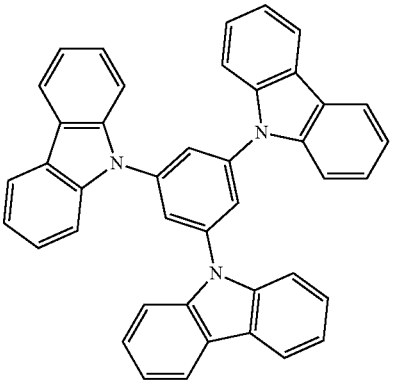
(el22)
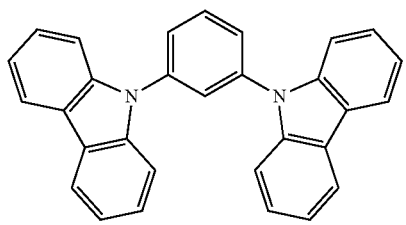
(el23)
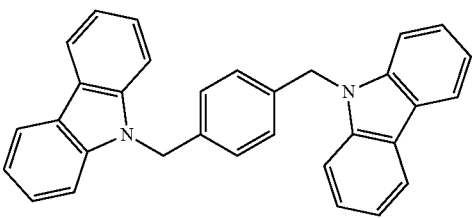

(el24) 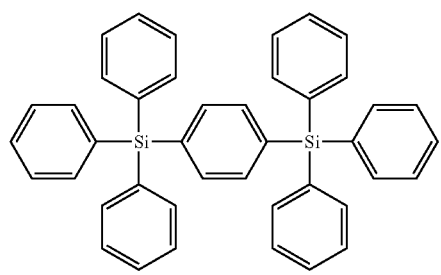
(el25) 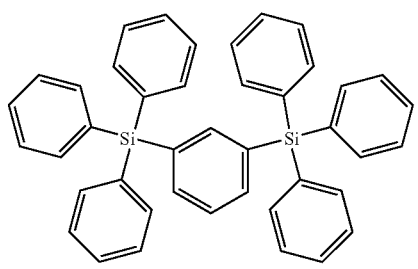
(el26) 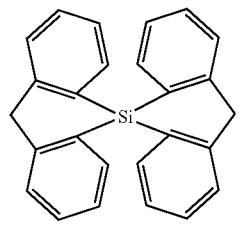
(el27) 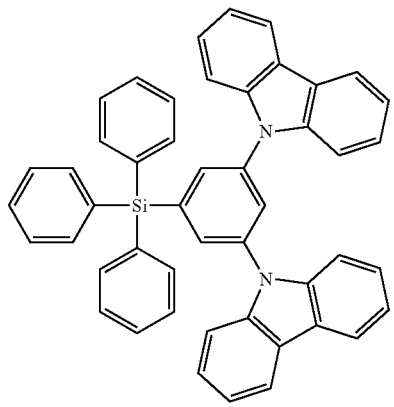
(el28) 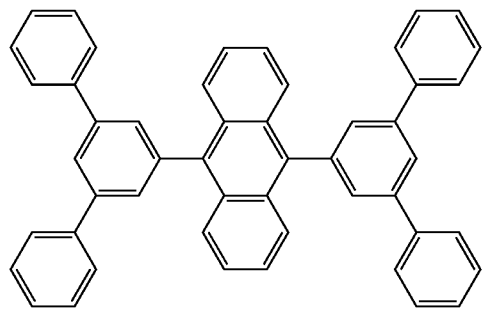
(el29) 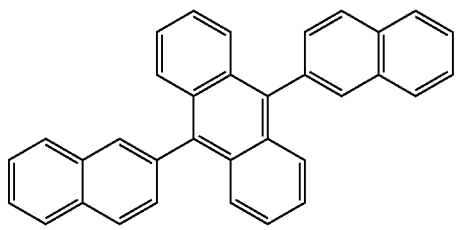
(el30) 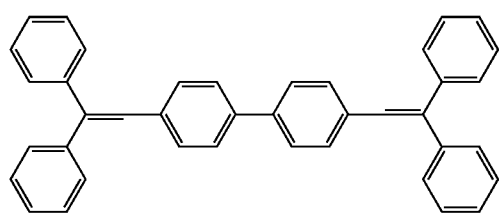
(el31) 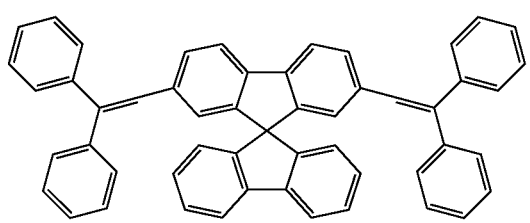

-continued
(el32)
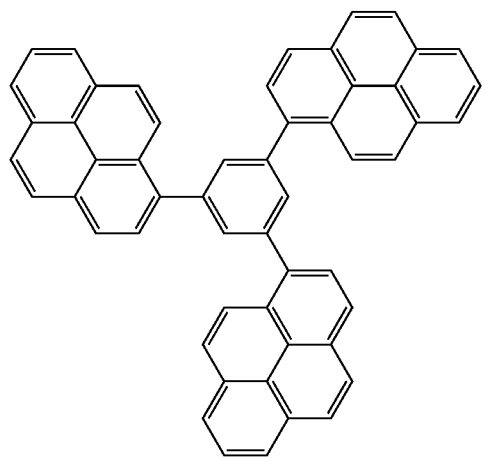
(el33)
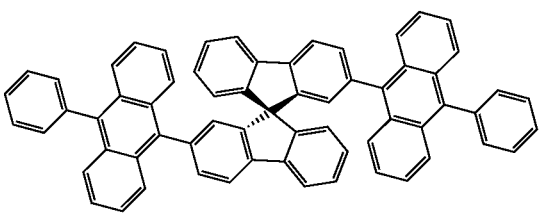
(el34)
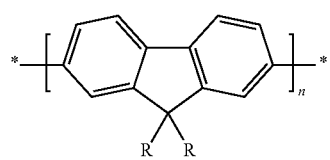
(el35)
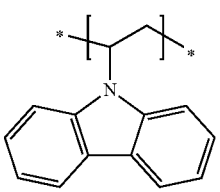
(el36)
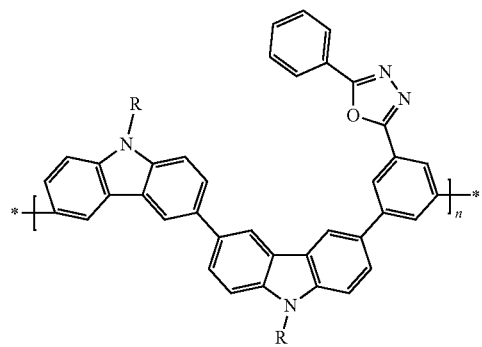
(el37)
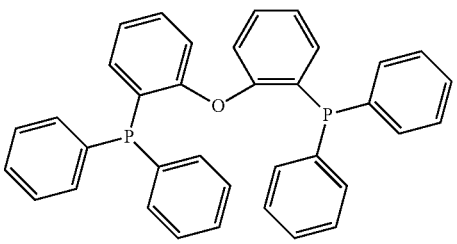
(el38)
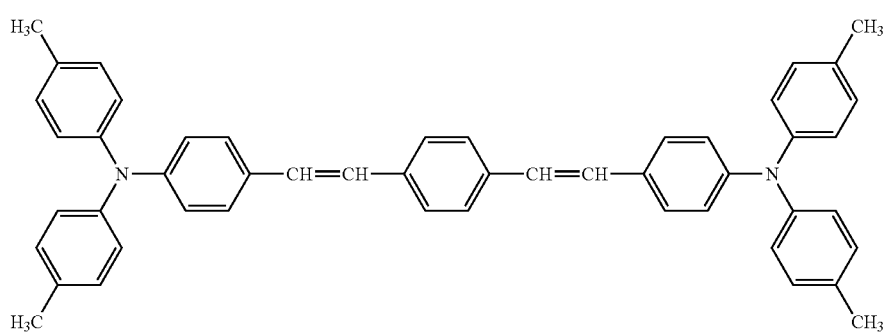
(el39)
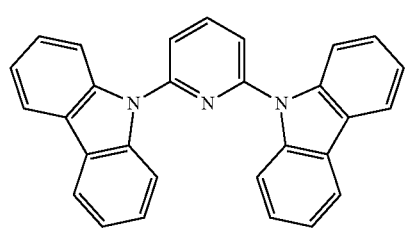

In a hole-blocking layer which is provided as needed, a compound having a hole-blocking action, such as a compound having a bipyridyl group and an ortho-terphenyl structure, a phenanthroline derivative such as bathocuproine (hereinafter abbreviated as BCP), a metal complex of quinolinol derivative such as aluminum (III) bis (2-methyl-8 quinolinate)-4-phenylphenolate (hereinafter, abbreviated as BAlq), various rare earth complexes, an oxazole derivative, a triazole derivative, or a triazine derivative may be used. These materials may also serve as materials of the electron-transporting layer. One kind of the materials may be used alone, or at least two kinds thereof may be used in combination. The hole-blocking layer may be a film of a single layer structure, or may be a film of a laminated structure. The materials may be subjected to deposition or another known method such as a spin coating method or an inkjet method to form a thin-film.

Compounds (hs1) to (hs11) which may be preferably used as hole-blocking materials are shown below.

(hs1)

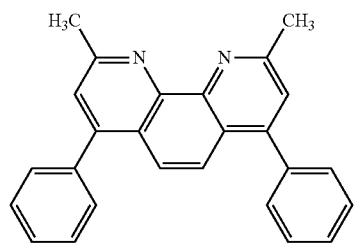

(hs2)

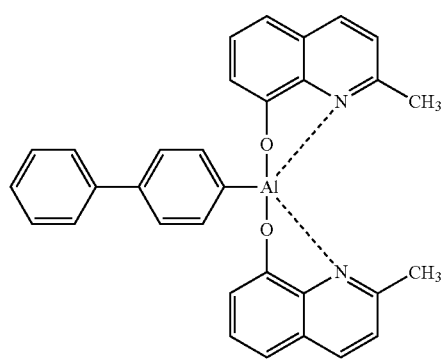

(hs3)

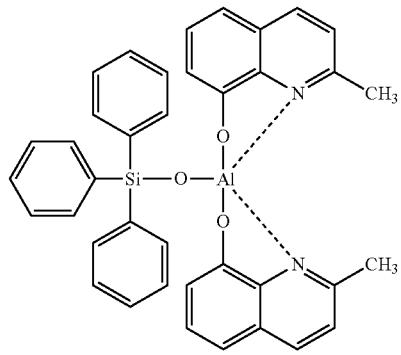

(hs4)

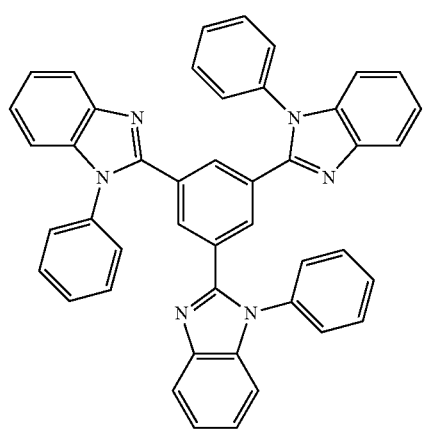

(hs5)

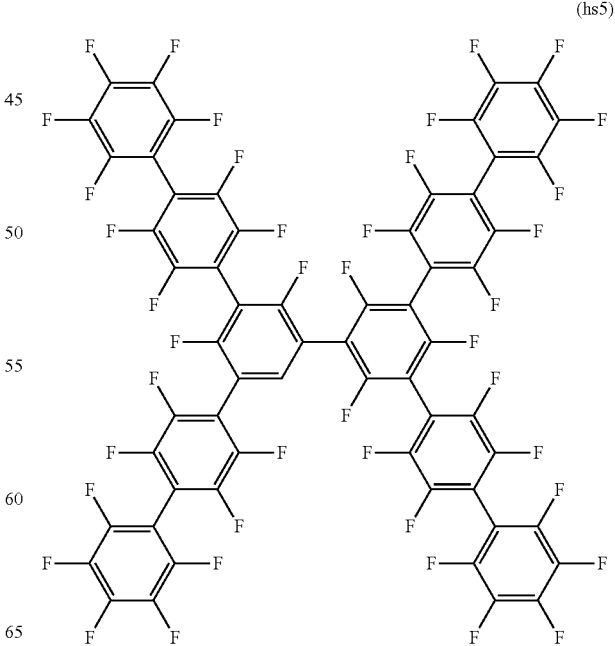

(hs6)
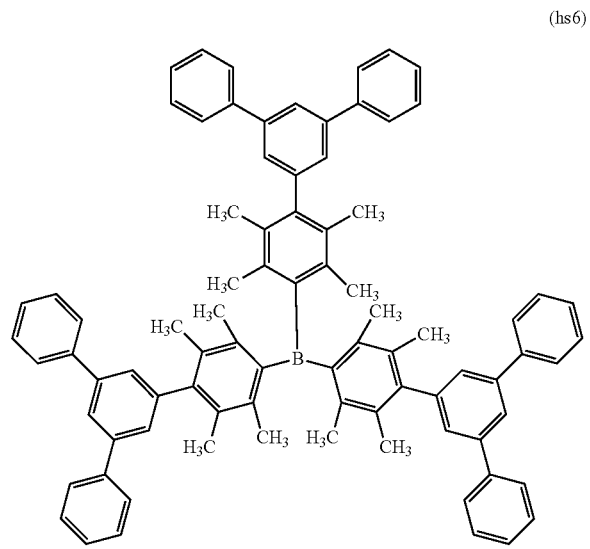

(hs10)
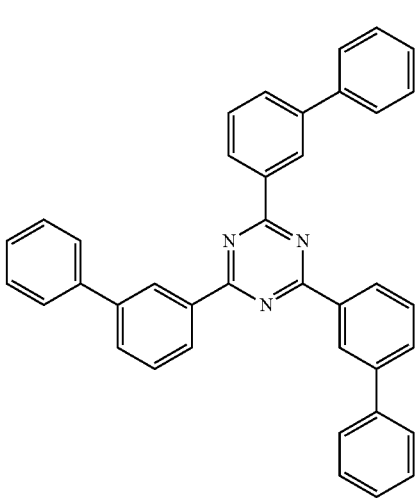

(hs7)
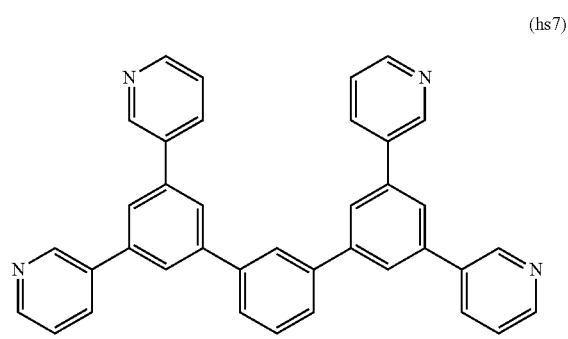

(hs11)
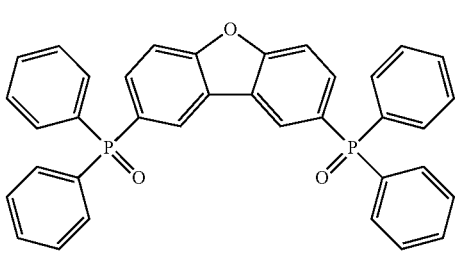

(hs8)
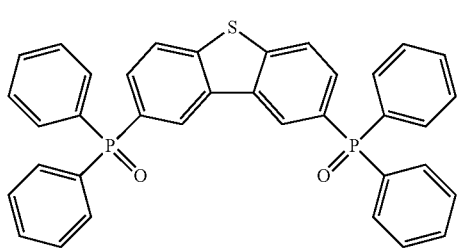

In addition to metal complexes of quinolinol derivatives such as Alq3 or BAlq, various other metal complexes, triazole derivatives, triazine derivatives, oxadiazole derivatives, thiadiazole derivatives, carbodiimide derivatives, quinoxaline derivatives, phenanthroline derivatives, or silole derivatives may be used in the electron-transporting layer which is provided as needed. One kind of the materials may be used alone, or at least two kinds thereof may be used in combination. The electron-transporting layer may be a film of a single layer structure, or may be a film of a laminated structure. The materials may be subjected to deposition or another known method such as a spin coating method or an inkjet method to form a thin-film.

(hs9)
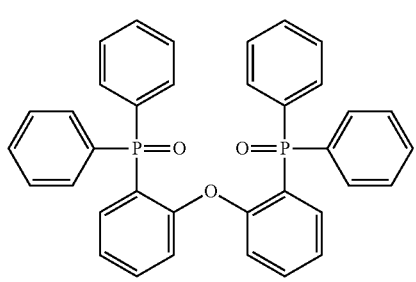

Although, in an electron injection layer which is provided as needed, alkali metal salts such as lithium fluoride or cesium fluoride, alkaline earth metal salts such as magnesium fluoride, or metal oxides such as aluminum oxide may be used, the materials may not be contained in a preferred selection of an electron-transporting layer and a cathode.

In the electron injection layer or the electron-transporting layer, a material in which a metal such as cesium is n-doped to a material commonly used in the layer may be used.

Compounds (et1) to (et30) which are preferably used as electron transporting materials are shown below.

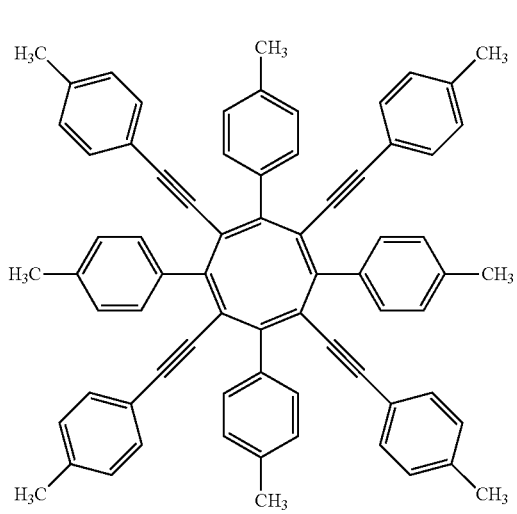
(et1)
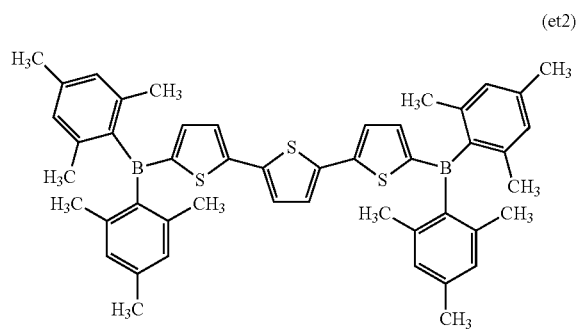
(et2)
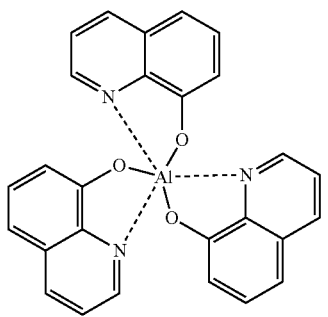
(et3)
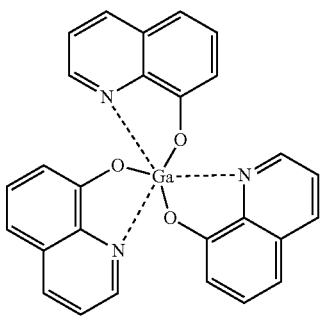
(et4)
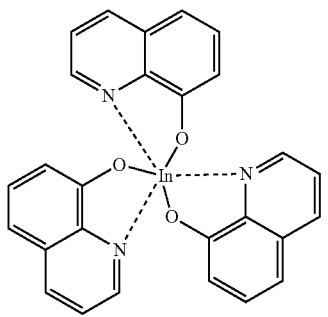
(et5)
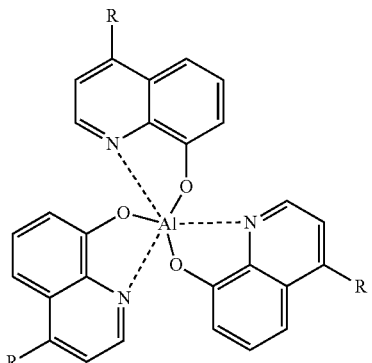
(et6)
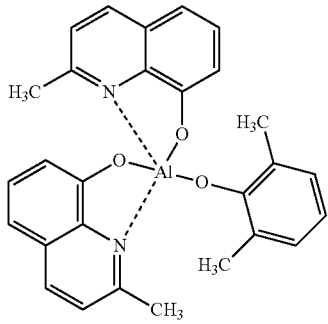
(et7)
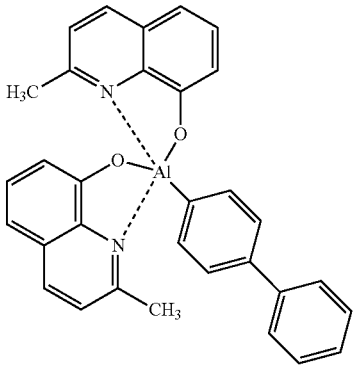
(et8)

-continued
(et9)
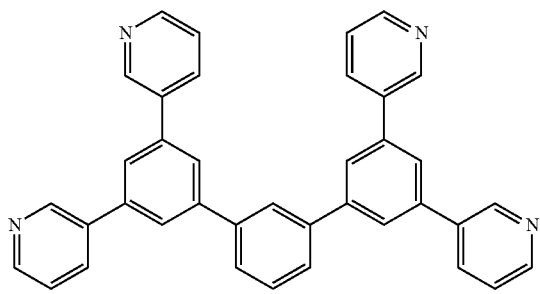
(et10)
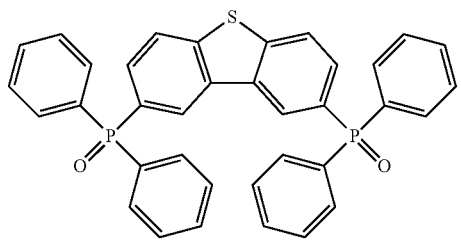
(et11)
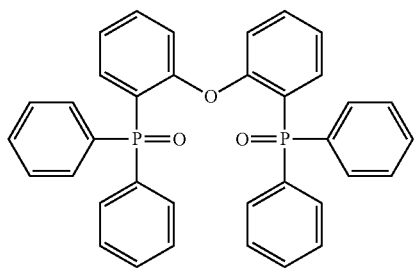
(et12)
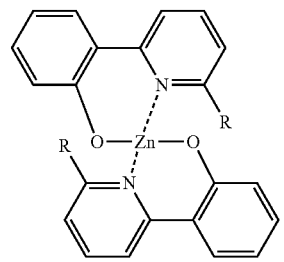 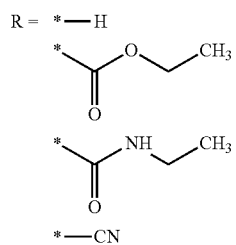
(et13)
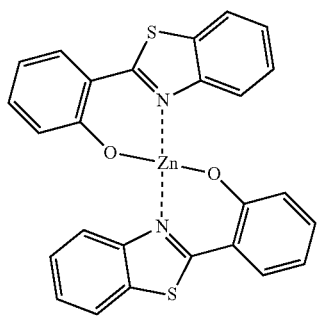
(et14)
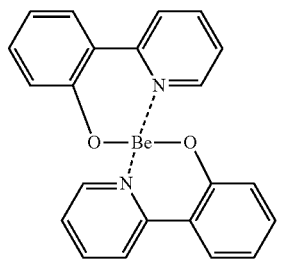
(et15)
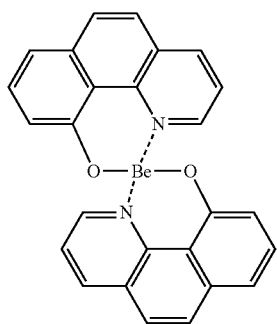
(et16)
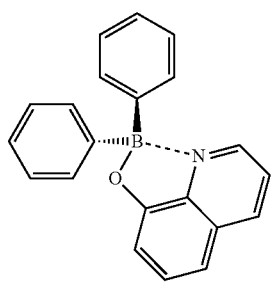

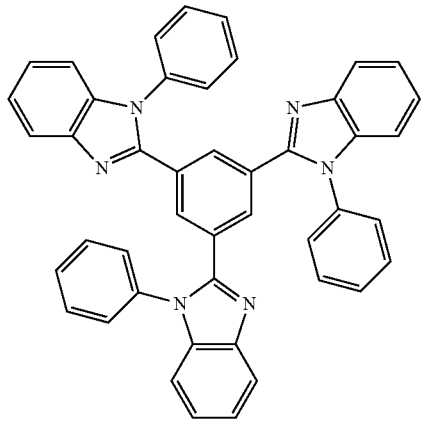
(et17)
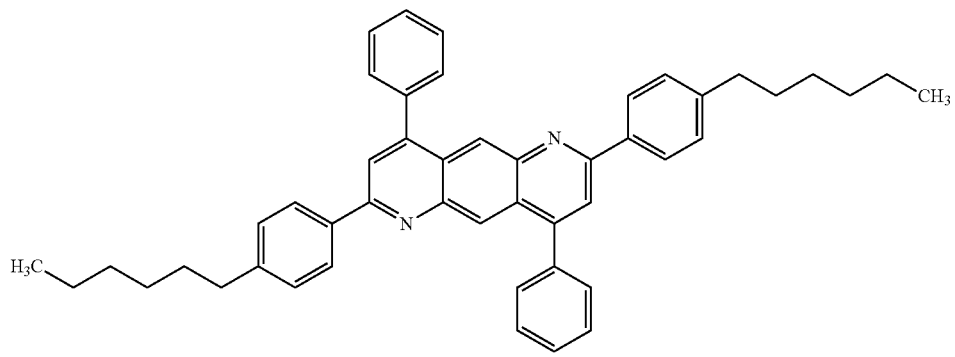
(et18)
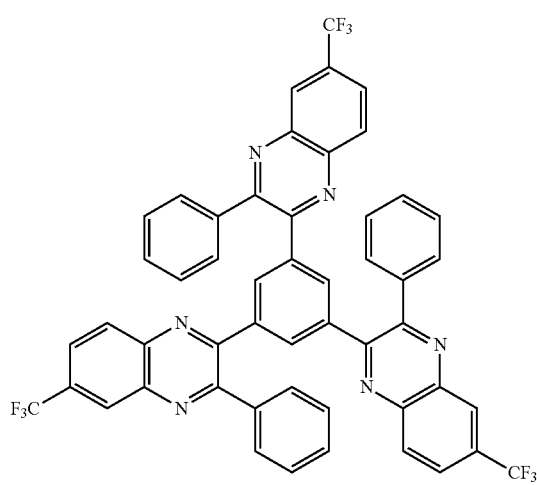
(et19)
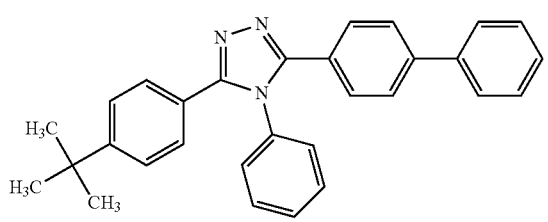
(et20)

(et21)
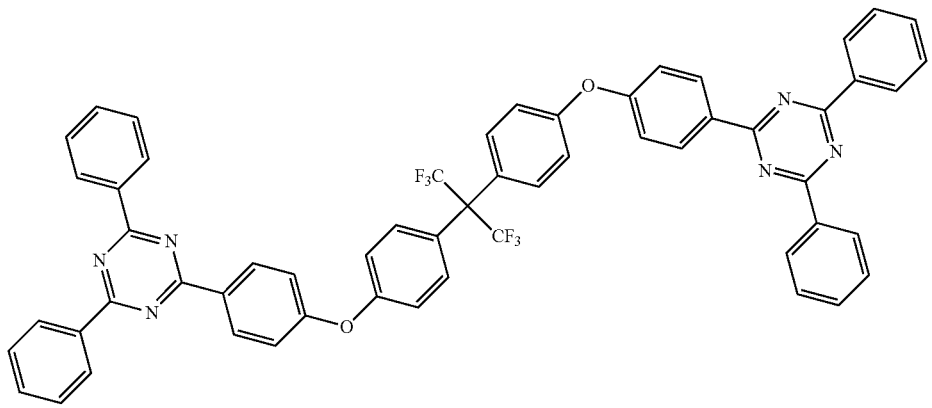
(et22)
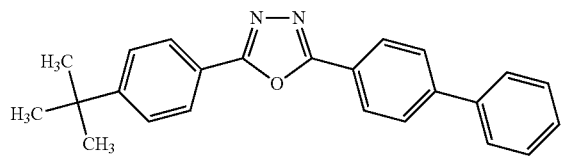
(et23)
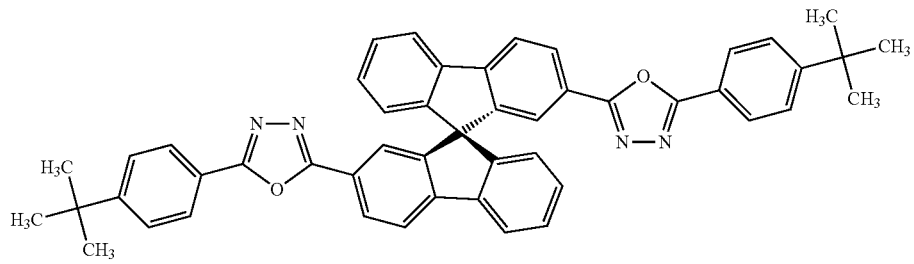
(et24)
(et25)
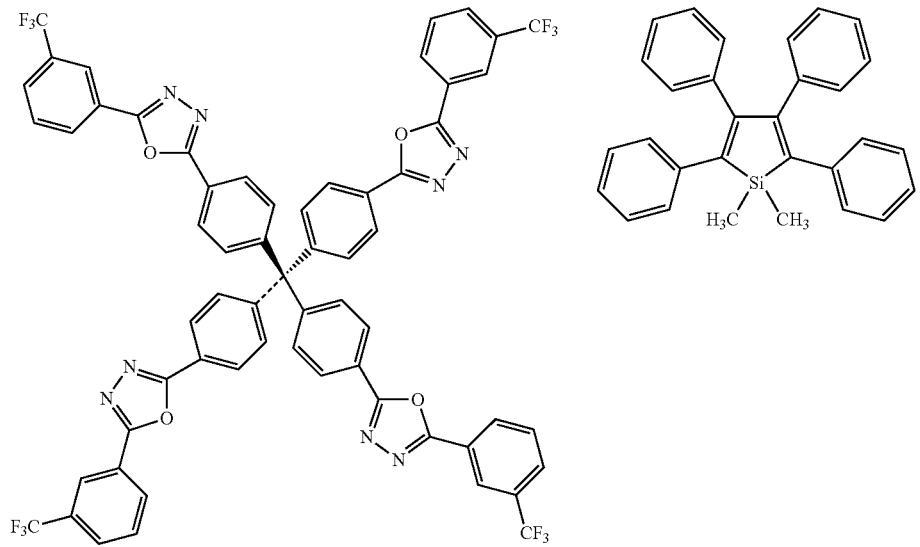

-continued
(et26) 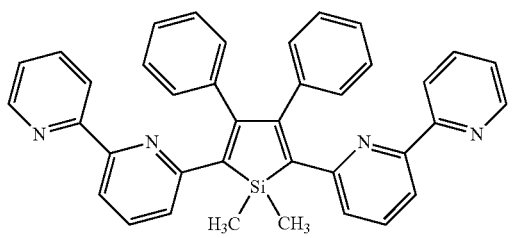
(et27) 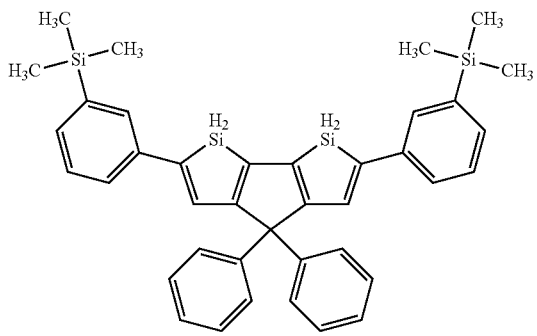
(et28) 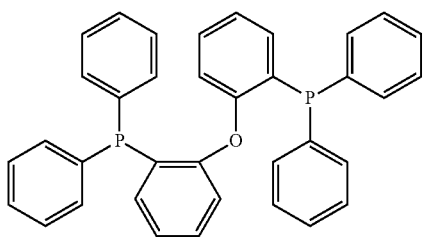
(et29) 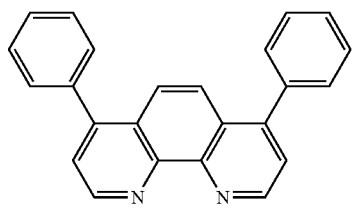
(et30) 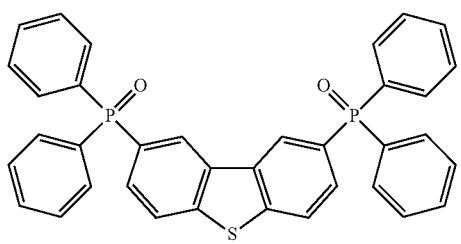
Compounds (ei1) to (ei4) which may be preferably used as electron injection materials are shown below.
(ei1) 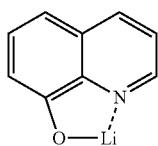
-continued
(ei4) 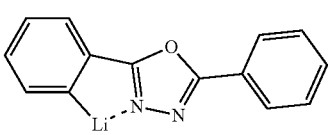
Compounds (st1) to (st5) which may be preferably used as stabilizing materials are shown below.
(ei2) 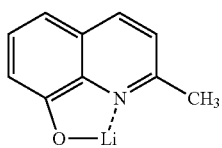
(st1) 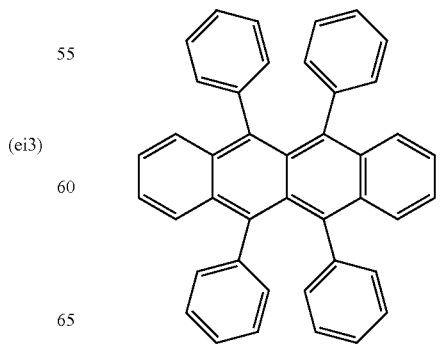
(ei3) 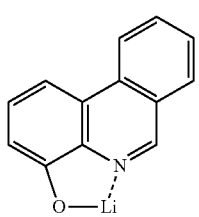

-continued (st2)
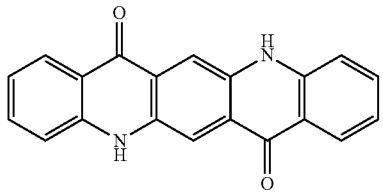

(st3)
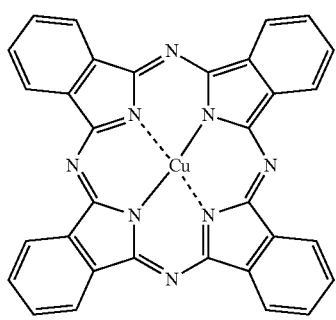

(st4)
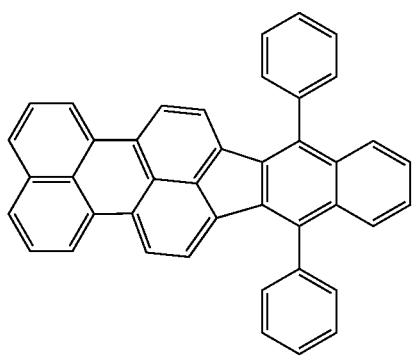

(st5)
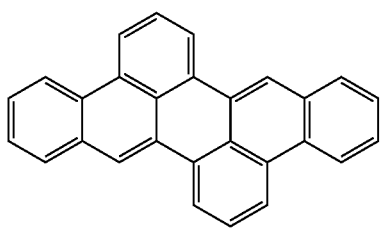

A material having a low work function is generally used in the cathode. Examples of the cathode material include sodium, an alloy of sodium and potassium, lithium, tin, magnesium, a mixture of magnesium and copper, a mixture of magnesium and aluminum, a mixture of magnesium and indium, a mixture of aluminum and aluminum oxide, indium, calcium, aluminum, silver, a mixture of lithium and aluminum, an alloy of magnesium and silver, an alloy of magnesium and indium, and an alloy of aluminum and magnesium. It is possible to obtain a transparent or semi-transparent cathode by using a transparent conductive material. The thickness of the cathode is usually 10 to 5000 nm, and preferably 50 to 200 nm. The sheet resistance of the cathode is preferably at least several hundreds Ω/□.

For the purpose of protecting the cathode formed of a metal having a low work function, a layer of metal having a high work function and being stable against atmosphere, such as aluminum, silver, nickel, chromium, gold, or platinum, is preferably laminated thereon, because the stability of the element is improved. A cathode interface layer may be provided between the cathode and an adjacent organic layer (such as an electron-transporting layer or an electron injection layer) to improve the contact therebetween. Examples of a material used in the cathode interface layer include aromatic diamine compounds, quinacridone compounds, naphthacene derivatives, organic silicon compounds, organic phosphorus compounds, compounds containing a N-phenyl carbazole skeleton, and N-vinylcarbazole polymer.

The light-emitting element according to the present invention may also be applied in any of a single element, an element having a structure in which components thereof are arranged in an array configuration, and an element having a structure in which an anode and a cathode are arranged in the X-Y matrix configuration.

EXAMPLES

Hereinafter, examples of the present invention are described.

Example 1

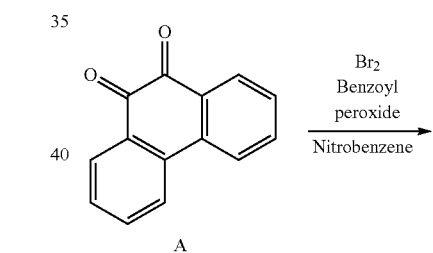

A

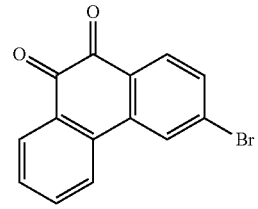

B

A compound A (9.25 g, 44.4 mmol) was charged in a 100 mL Schlenk tube, and then 20 mL of nitrobenzene was added thereto. Then, benzoyl peroxide (0.39 g, 1.61 mmol) was added thereto, and bromine (2.29 mL, 44.4 mmol) was added thereto dropwise. Then, the resultant was stirred while conducting heating for 4 hours at 60° C. Methanol was added to the resultant solution to precipitate a solid, and the solid was removed therefrom by filtration. The resulting solid was purified by silica gel column chromatography (developing solvent: toluene) to obtain a yellow solid (yield amount: 3.02 g, yield: 24%).

Chemical shift values (δ) of the compound measured by ¹H NMR (400 MHz, CDCl₃) were as follows: δ 8.22 (dd, J=7.6, 1.6 Hz, 1H), 8.18 (d, J=1.6 Hz, 1H), 8.06 (d, J=8.4 Hz, 1H), 7.98 (d, J=8.0 Hz, 1H), 7.75 (td, J=7.6, 1.2 Hz, 1H), 7.62 (dd, J=8.4, 2.0 Hz, 1H), 7.53 (t, J=7.6 Hz, 1H). It was confirmed by ¹H NMR measurement that the obtained compound was a compound B.

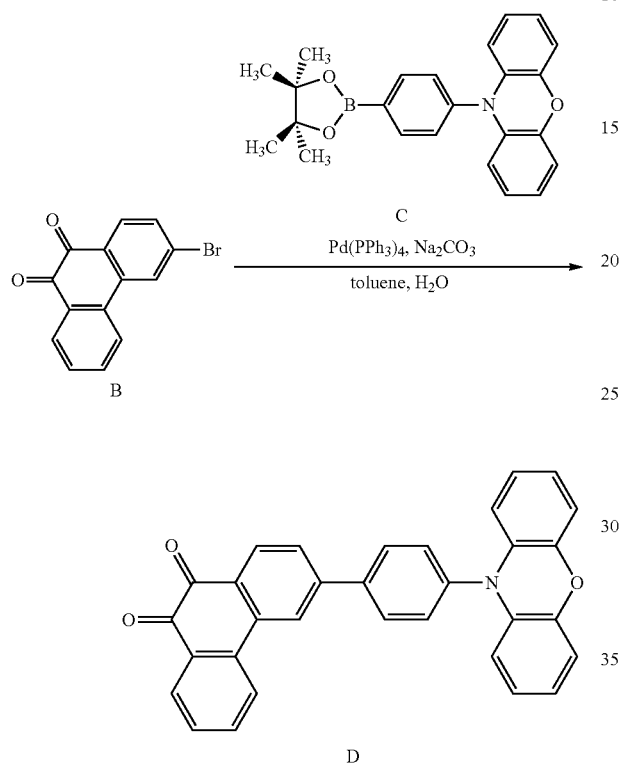

The compound B (0.97 g, 3.38 mmol), a compound C (1.43 g, 3.71 mmol), Pd(PPh₃)₄ (0.20 g, 0.17 mmol), 40 mL of toluene, and 20 mL of a 2M aqueous Na₂CO₃ solution were charged in a three-necked flask having a capacity of 300 mL under a nitrogen atmosphere, followed by stirring the resultant mixture while conducting heating at 75° C. for 12 hours. Water was added to the resultant solution, the resultant mixture was subjected to extraction using chloroform, and then the resultant extract was dried by adding sodium sulfate thereto. Sodium sulfate hydrate was removed by filtration, and the solvent was distilled off from the filtrate using an evaporator. The resultant solid was purified by silica gel column chromatography (developing solvent=hexane:ethyl acetate=10:1) to obtain a black solid (yield amount: 0.95 g, yield: 60%).

Chemical shift values (δ) of the compound measured by ¹H NMR (400 MHz, CDCl₃) were as follows: δ 9.30 (d, J=8.4 Hz, 1H), 9.24 (d, J=7.2 Hz, 1H), 8.91 (s, 1H), 8.78 (d, J=8.0 Hz, 1H), 8.12 (dd, J=8.0 Hz, 1.2 Hz, 1H), 8.08 (d, J=8.4 Hz, 2H), 8.00 (t, J=7.2 Hz, 1H), 7.89 (t, J=6.8 Hz, 1H), 7.63 (d, J=8.4 Hz, 2H), 6.68 (m, 6H), 6.20 (d, J=8.8 Hz, 2H). It was confirmed by ¹H NMR measurement that the obtained compound was a compound D.

As the compound C, a compound prepared in accordance with the method described in paragraphs [0098] to [0101] of WO 2015/080183 was used.

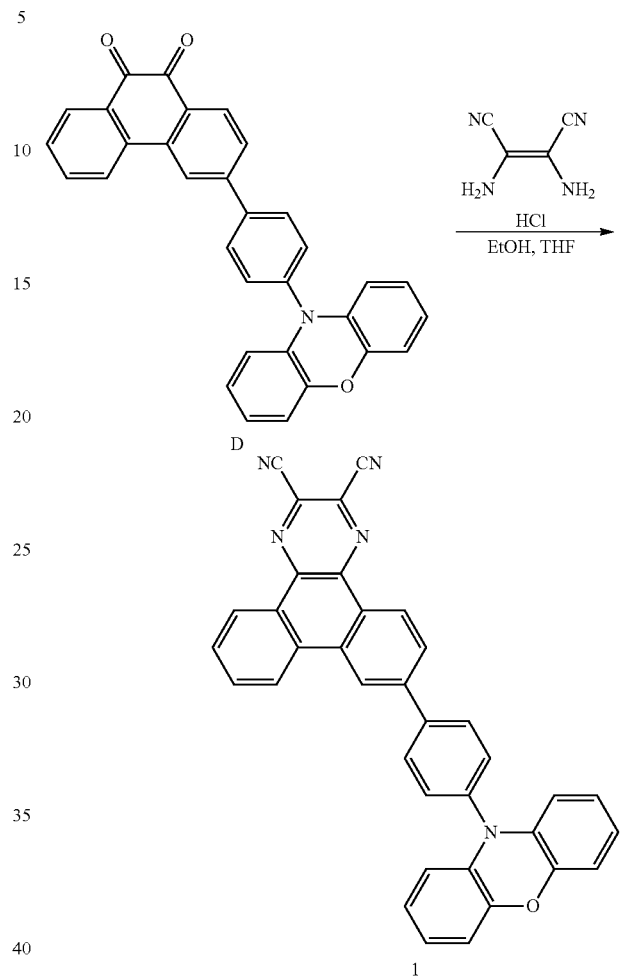

The compound D (0.70 g, 1.50 mmol), diaminomaleonitrile (0.19 g, 1.80 mmol), 40 mL of ethanol, 40 mL of THF (tetrahydrofuran), and 0.23 mL of 12M hydrochloric acid were charged in a three-necked flask having a capacity of 300 mL, and then the resultant mixture was stirred while conducting heating at 40° C. for 24 hours. Water was added to the resultant solution, the resultant mixture was subjected to extraction with chloroform, and then the resultant extract was dried by adding sodium sulfate thereto. Sodium sulfate hydrate was removed by filtration, and the solvent was distilled off from the filtrate using an evaporator. The resulting solid was purified by silica gel column chromatography (developing solvent: toluene) to obtain a red solid (yield amount: 0.40 g, yield: 49%).

Chemical shift values (δ) of the compound measured by ¹H NMR (400 MHz, CDCl₃) were as follows: δ 9.31 (d, J=8.8 Hz, 1H), 9.24 (dd, J=8.0 Hz, 1.2 Hz, 1H), 8.90 (d, 1.6 Hz, 1H), 8.78 (d, J=8.4 Hz, 1H), 8.13 (dd, J=8.4 Hz, 1.6 Hz, 1H), 8.05 (d, J=8.4 Hz, 2H), 8.00 (td, J=7.2 Hz, 1.6 Hz, 1H), 7.89 (td, J=7.2 Hz, 1.2 Hz 1H), 7.57 (d, J=8.4 Hz, 2H), 6.69 (m, 6H), 6.06 (dd, J=8.0 Hz 2.0 Hz, 2H). It was confirmed by ¹H NMR measurement that the obtained compound was a compound 1 (Px-CNBQx).

Example 2

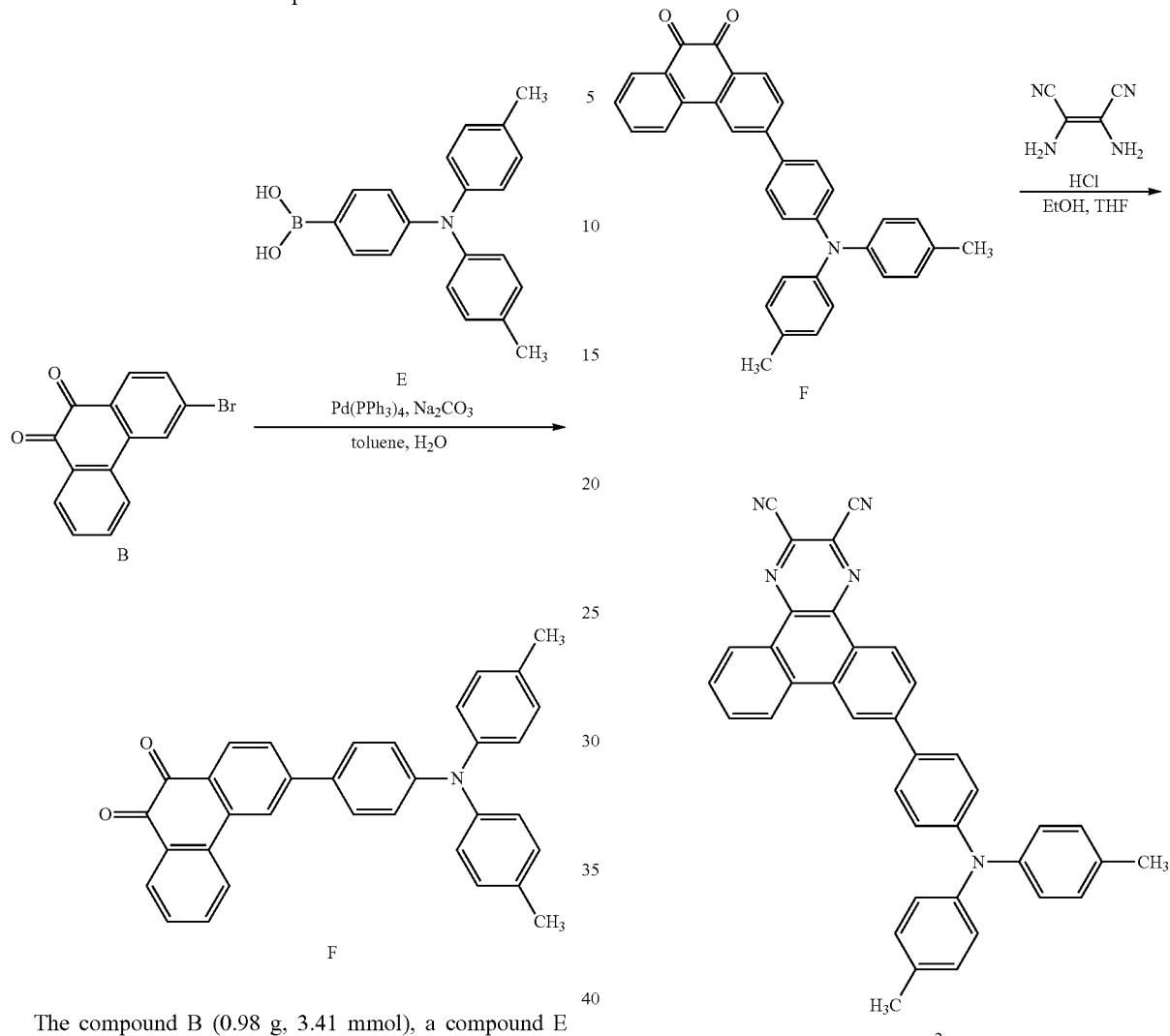

The compound B (0.98 g, 3.41 mmol), a compound E (1.19 g, 3.75 mmol), Pd(PPh$_3$)$_4$ (0.20 g, 0.17 mmol), 40 mL of toluene, and 20 mL of 2M aqueous Na$_2$CO$_3$ solution were charged in a three-necked flask having a capacity of 300 mL under a nitrogen atmosphere, and the mixture was stirred while conducting heating at 75° C. for 11 hours. Water was added to the resultant solution, the mixture was subjected to extraction with chloroform, and then the resultant extract was dried by adding sodium sulfate. Sodium sulfate hydrate was removed by filtration, and the solvent was distilled off from the filtrate using an evaporator. The resultant solid was purified by silica gel column chromatography (developing solvent: hexane:ethyl acetate=5:1) to obtain a black solid (yield amount: 1.39 g, yield: 85%).

Chemical shift values (δ) of the compound measured by $^1$H NMR (400 MHz, CDCl$_3$) were as follows: δ 8.25-8.20 (m, 2H), 8.17 (d, J=1.6 Hz, 1H), 8.11 (d, J=8.0 Hz, 1H), 7.73 (td, J=8.0, 1.6 Hz, 1H), 7.63 (dd, J=8.4, 1.6 Hz, 1H), 7.54 (dd, J=8.8, 2.0 Hz, 2H), 7.49 (td, J=7.6, 0.8 Hz, 1H), 7.13-7.05 (m, 10H), 2.35 (s, 6H). It was confirmed by $^1$H NMR measurement that the obtained compound was a compound F.

As the compound E, a compound prepared in accordance with the method described in paragraphs [0141] and [0142] of Japanese Unexamined Patent Application, Publication No. 2008-291011 was used.

A compound F (0.70 g, 1.46 mmol), diaminomaleonitrile (0.19 g, 1.76 mmol), 40 mL of ethanol, 40 mL of THF, and 0.23 mL of 12M hydrochloric acid were charged in a three-necked flask having a capacity of 300 mL, and the mixture was stirred while conducting heating at 40° C. for 24 hours. Water was added to the resultant solution, the resultant mixture was subjected to extraction with chloroform, and then the resultant extract was dried by adding sodium sulfate thereto. Sodium sulfate hydrate was removed by conducting filtration, and the solvent was distilled off from the filtrate using an evaporator. The resultant solid was purified by silica gel column chromatography (developing solvent: toluene) to obtain a red solid (yield amount: 0.52 g, yield: 64%).

Chemical shift values (δ) of the compound measured by $^1$H NMR (400 MHz, CDCl$_3$) were as follows: δ 9.16 (t, J=8.4 Hz, 2H), 8.76 (d, J=1.6 Hz, 1H), 8.70 (d, 8.4 Hz, 1H), 8.01 (dd, J=8.8 Hz, 2.0 Hz 1H), 7.96 (td, J=8.4 Hz, 1.2 Hz, 1H), 7.84 (td, J=8.4 Hz, 1.2 Hz, 1H), 7.66 (dt, J=8.8 Hz, 2.0 Hz 2H), 7.19-7.10 (m, 10H), 2.36 (s, 6H). It was confirmed by $^1$H NMR measurement that the obtained compound was a compound 2 (Da-CNBQx).

Example 3

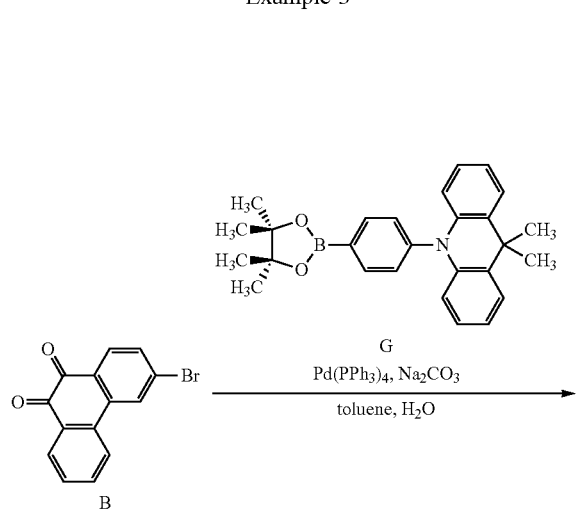

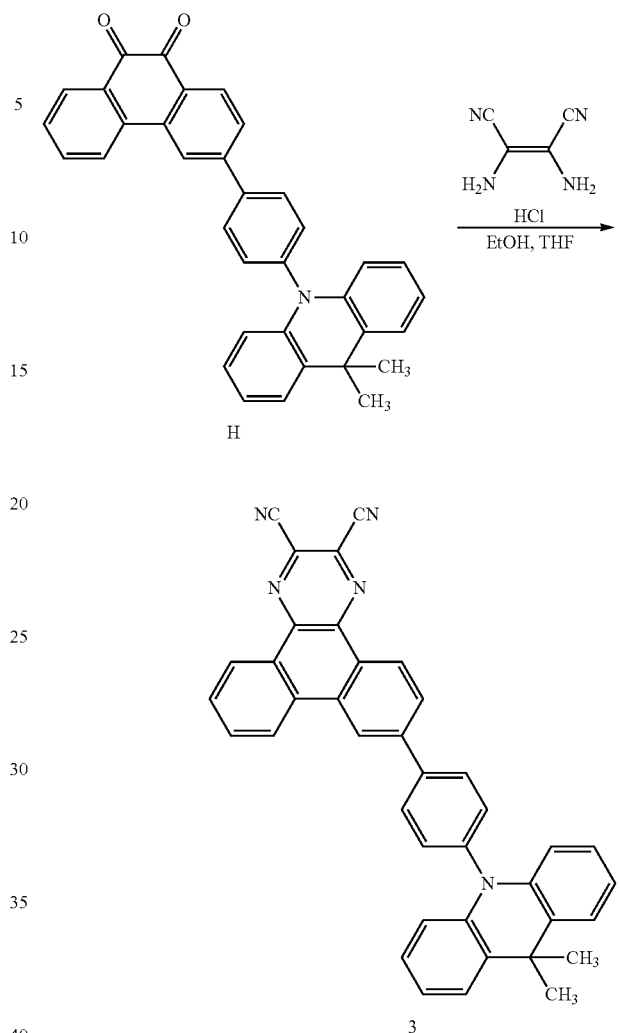

The compound B (1.50 g, 5.22 mmol), a compound G (2.36 g, 5.74 mmol), Pd(PPh₃)₄ (0.30 g, 0.26 mmol), 50 mL of toluene, and 25 mL of a 2M aqueous $Na_2CO_3$ solution were charged in a three-necked flask having a capacity of 300 mL under a nitrogen atmosphere, and the mixture was stirred while conducting heating at 75° C. for 14 hours. Water was added to the resultant solution, the resultant mixture was subjected to extraction with chloroform, and then the resultant extract was dried by adding sodium sulfate thereto. Sodium sulfate hydrate was removed by conducting filtration, and the solvent was distilled off from the filtrate using an evaporator. The resultant solid was purified by silica gel column chromatography (developing solvent: hexane:ethyl acetate=3:1) to obtain a yellow solid (yield amount: 2.13 g, yield: 83%).

Chemical shift values (δ) of the compound measured by ¹H NMR (400 MHz, $CDCl_3$) were as follows: δ 8.34 (d, J=8.4 Hz, 2H), 8.26 (dd, J=7.6, 1.2 Hz, 1H), 8.19 (d, J=8.0 Hz, 1H), 7.96 (d, J=8.4 Hz, 2H), 7.81-7.75 (m, 2H), 7.55-7.48 (m, 5H), 7.01-6.96 (m, 4H), 6.35 (d, J=8.4 Hz, 2H), 1.72 (s, 6H). It was confirmed by 1H NMR measurement that the obtained compound was a compound H.

The compound G was a compound prepared in accordance with paragraphs [0092] to [0095] of WO 2015/080183.

The compound H (1.00 g, 2.03 mmol), diaminomaleonitrile (0.30 g, 2.78 mmol), 50 mL of ethanol, 25 mL of THF, and 0.31 mL of 12M hydrochloric acid were charged in a three-necked flask having a capacity of 300 mL, and the resultant mixture was stirred while conducting heating at 40° C. for 24 hours. Water was added to the resultant solution, the resultant mixture was subjected to extraction with chloroform, and then the resultant extract was dried by adding sodium sulfate thereto. Sodium sulfate hydrate was removed by conducting filtration, and the solvent was distilled off from the filtrate using an evaporator. The resultant solid was purified by silica gel column chromatography (developing solvent: toluene) to obtain an orange solid (yield amount: 0.19 g, yield: 17%).

Chemical shift values (δ) of the compound measured by ¹H NMR (400 MHz, $CDCl_3$) were as follows: δ 9.32 (d, J=8.4 Hz, 1H), 9.25 (dd, J=8.0, 1.3 Hz, 1H), 8.95 (d, J=1.6 Hz, 1H), 8.82 (d, J=8.4 Hz, 1H), 8.18 (dd, J=8.8, 1.6 Hz, 1H), 8.09 (dd, J=6.4, 2.0 Hz, 2H), 8.02 (td, J=8.0 Hz, 1.2 Hz, 1H), 8.90 (td, J=8.0 Hz, 0.8 Hz, 1H), 7.57 (d, J=8.8 Hz, 2H), 7.51 (dd, J=8.0 Hz, J=1.6 Hz, 2H), 7.05-6.96 (m, 4H), 6.40 (dd, J=8.0, 1.2 Hz, 2H), 1.74 (s, 6H). It was confirmed by ¹H NMR measurement that the obtained compound was a compound 3 (Ac-CNBQx).

Example 4

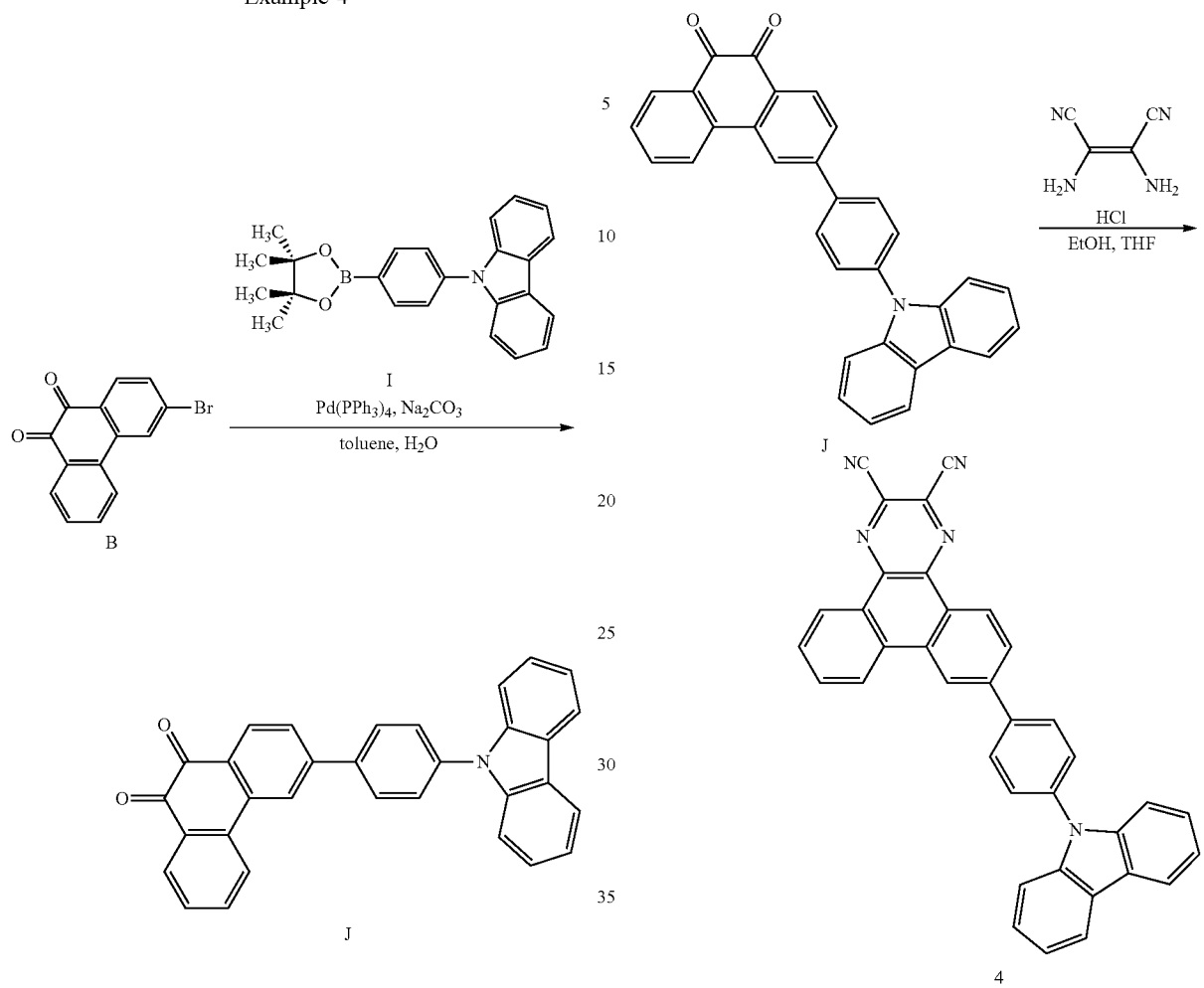

The compound B (1.00 g, 3.48 mmol), a compound 1 (1.41 g, 3.82 mmol), Pd(PPh$_3$)$_4$ (0.20 g, 0.17 mmol), 50 mL of toluene, and 25 mL of a 2M aqueous Na$_2$CO$_3$ solution were charged in a three-neck flask having a capacity of 300 mL under a nitrogen atmosphere, and the mixture was stirred while conducting heating at 75° C. for 6 hours. Water was added to the resultant solution, the resultant mixture was subjected to extraction with chloroform, and then the resultant extract was dried by adding sodium sulfate thereto. Sodium sulfate hydrate was removed by conducting filtration, and the solvent was distilled off from the filtrate using an evaporator. The resultant solid was purified by silica gel column chromatography (developing solvent: hexane:ethyl acetate=3:1) to obtain a yellow solid (yield amount: 1.61 g, yield: 97%).

Chemical shift values (δ) of the compound measured by $^1$H NMR (400 MHz, CDCl$_3$) were as follows: δ 8.34 (d, J=8.0 Hz, 1H), 8.32 (d, J=1.2 Hz, 1H), 8.26 (dd, J=7.6, 1.2 Hz, 1H), 8.20-8.17 (m, 3H), 7.95 (dd, J=6.8, 2.0 Hz, 2H), 7.81-7.76 (m, 4H), 7.55-7.43 (m, 5H), 7.35-7.31 (m, 2H). It was confirmed by $^1$H NMR measurement that the obtained compound was a compound J.

The compound I was a compound prepared in accordance with paragraphs [0346] and [0347] of WO 2013/180097.

The compound J (0.70 g, 1.56 mmol), diaminomaleonitrile (0.20 g, 1.85 mmol), 40 mL of ethanol, 20 mL of THF, and 0.24 mL of a 12M hydrochloric acid were charged in a three-necked flask having a capacity of 300 mL, and the mixture was stirred while heating at 40° C. for 24 hours. Water was added to the resultant solution, the resultant mixture was subjected to extraction with chloroform, and then the resultant extract was dried by adding sodium sulfate thereto. Sodium sulfate hydrate was removed by conducting filtration, and the solvent was distilled off from the filtrate using an evaporator. The resultant solid was purified by silica gel column chromatography (developing solvent: toluene) to obtain a yellow solid (yield amount: 0.40 g, yield: 49%).

Chemical shift values (δ) of the compound measured by $^1$H NMR (400 MHz, CDCl$_3$) were as follows: δ 9.32 (d, J=8.4 Hz, 1H), 9.25 (dd, J=10.8, 2.8 Hz, 1H), 8.94 (d, J=2.0 Hz, 1H), 8.80 (d, J=8.8 Hz, 1H), 8.20-8.16 (m, 3H), 8.07 (dd, J=8.8, 2.4 Hz, 2H), 8.01 (td, J=8.8, 1.6 Hz, 1H), 7.89 (td, J=7.2, 1.2 Hz, 1H), 7.81 (dd, J=8.4, 2.0 Hz, 2H), 7.55-7.52 (m, 2H), 7.47 (dd, J=7.2, 1.2 Hz, 2H), 7.36-7.31 (m, 2H). It was confirmed by $^1$H NMR measurement that the obtained compound was a compound 4 (Cz-CNBQx).

Organic photoluminescent elements and organic electroluminescent elements were prepared using the compounds 1-4 to evaluate light-emission characteristics. Evaluation of the light-emission characteristics was conducted using a source meter (manufactured by Keithley Co.: 2400 series), a semiconductor parameter analyzer (manufactured by Agilent Technologies: E5273A), an optical power meter measuring device (manufactured by Newport Corporation: 1930C), an optical spectrometer (manufactured by Ocean Optics Corporation: USB2000), spectroradiometer (manufactured by TOPCON CORPORATION: SR-3), and a streak camera (manufactured by Hamamatsu Photonics KK: C4334 type).

Example 5

Figure 2:
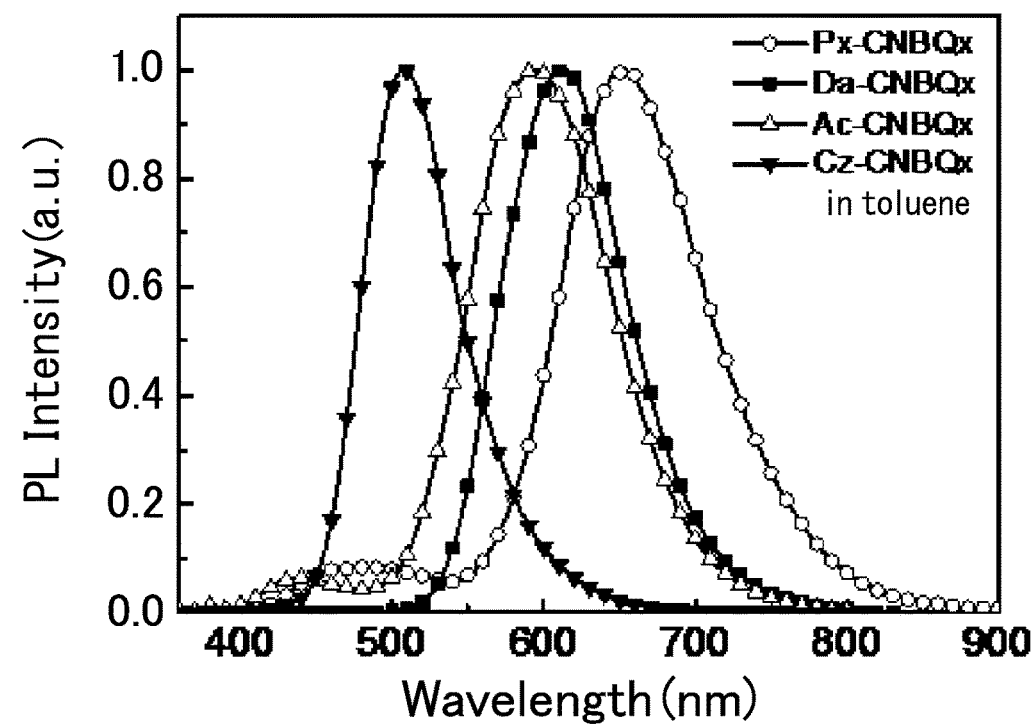
FIG. 2 is a drawing that indicates emission spectra of a Px-CNBQz toluene solution, a Da-CNBQz toluene solution, an Ac-CNBQx toluene solution, and a Cz-CNBQx toluene solution, prepared in Example 5.

In a glove box under an argon atmosphere, toluene solutions of Px-CNBQx (Compound 1), Da-CNBQx (Compound 2), Ac-CNBQx (Compound 3), and Cz-CNBQx (Compound 4) were prepared. These solutions were subjected to measurement of the luminescent spectrum and the absorption spectrum by 340 nm excitation light. Furthermore, toluene solutions (air) prepared without conducting bubbling and toluene solutions ($N_2$) prepared by conducting bubbling with nitrogen gas were subjected to measurement of quantum yield ($\varphi_{PL}$) by a photoluminescence method. The results are shown in FIGS. 1 and 2 and Table 1.

TABLE 1

| Compound | Absorption peak wavelength $\lambda_{abs}$ [nm] | Luminescent peak wavelength $\lambda_{PL}$ [nm] | $\Phi_{PL}$ [%] (air→$N_2$) |
|---|---|---|---|
| Px-CNBQx | 334, 380, 397, 457 | 652 | <1 |
| Da-CNBQx | 314, 377, 459 | 613 | 73→96 |
| Ac-CNBQx | 340, 383, 403, 435 | 595 | 27→28 |
| Cz-CNBQx | 340, 403 | 508 | 82→95 |

Example 6

Figure 3:
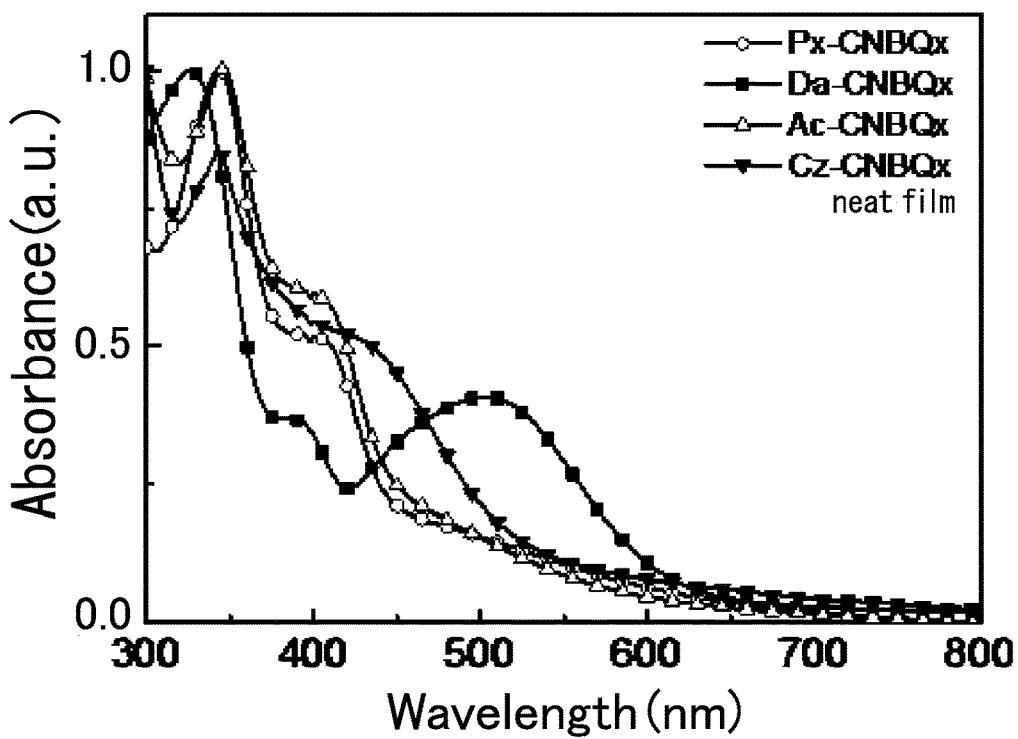
FIG. 3 is a drawing that indicates absorption spectra of organic photoluminescent elements, prepared in Example 6.

Px-CNBQx, Da-CNBQx, Ac-CNBQx and Cz-CNBQx were used as evaporation sources, and deposited on quartz substrates under a condition in which the vacuum degree was $10^{-4}$ Pa or less, and thus organic photoluminescent elements each having a thin-film (neat film) having a thickness of 100 nm were obtained. These organic photoluminescent elements were subjected to measurement of the absorption spectrum. The results are shown in FIG. 3.

Example 7

Figure 4:
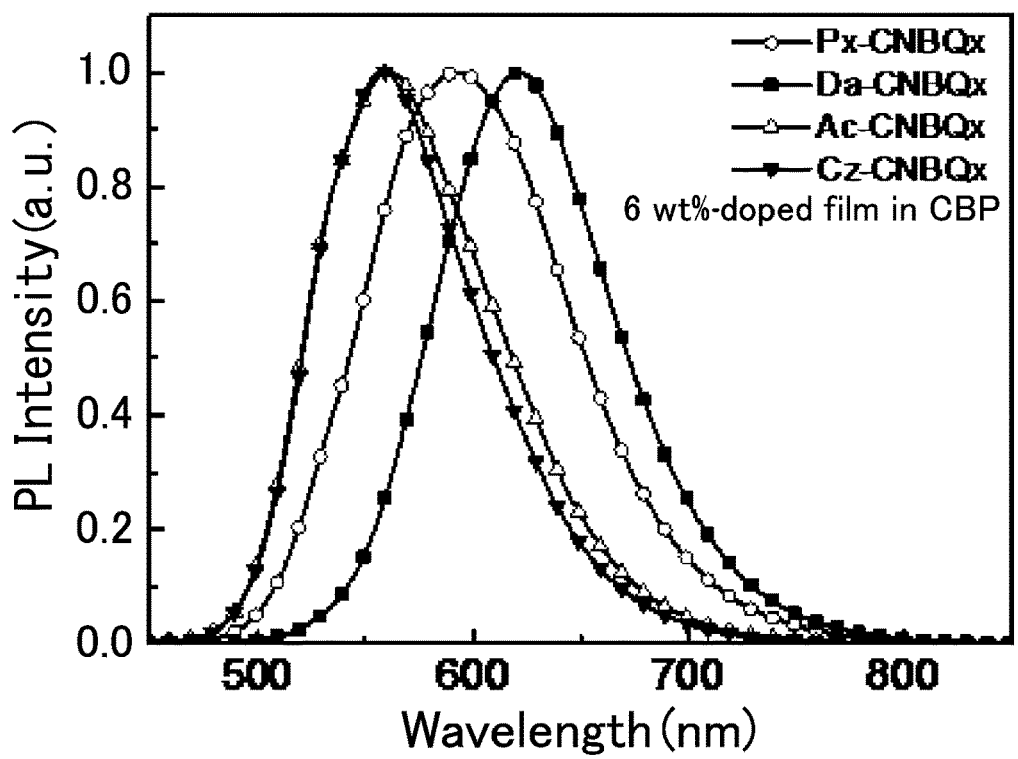
FIG. 4 is a drawing that indicates emission spectra of organic photoluminescent elements, prepared in Example 7.

The combination of CBP and Px-CNBQx, Da-CNBQx, Ac-CNBQx or Cz-CNBQx was used as an evaporation source and deposited on a quartz substrate at $10^{-4}$ Pa or less, and thus an organic photoluminescent element having a thin film in which the concentration of Px-CNBQx, Da-CNBQx, Ac-CNBQx or Cz-CNBQx was 6.0% by weight and the thickness was 100 nm was obtained. The organic photoluminescent element was subjected to measurement of the luminescent spectrum and the absorption spectrum by excitation light having a wavelength of 340 nm. Furthermore, toluene solutions (air) prepared without conducting bubbling and toluene solutions ($N_2$) prepared by conducting bubbling with nitrogen gas were subjected to measurement of quantum yield ($\varphi_{PL}$) by a photoluminescence method. The results are shown in FIG. 4 and Table 2. The full-width at half-maximum, FWHM (μm), which was the wavelength width when the luminescent intensity became half of the peak luminescent intensity, and the full-width at half-maximum, FWHM (eV), which was the energy width when the luminescent intensity became half of the peak luminescent intensity, were confirmed from the results shown in FIG. 4.

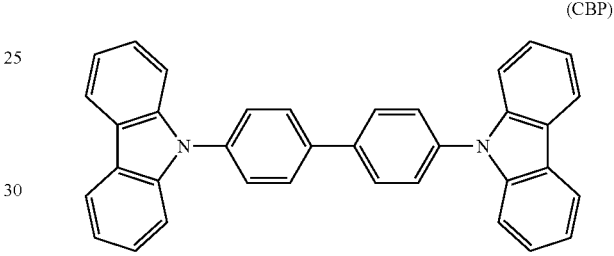

(CBP)

TABLE 2

| Compound | Absorption peak wavelength $\lambda_{abs}$ [nm] | Luminescent peak wavelength $\lambda_{PL}$ [nm] | FWHM [nm] | FWHM [eV] | $\Phi_{PL}$ [%] (air→$N_2$) |
|---|---|---|---|---|---|
| Px-CNBQx | 343, 405[a], 490[a] | 593 | 109 | 0.385 | 47→52 |
| Ds-CNBQx | 327, 390[a], 502 | 521 | 97 | 0.314 | 82→35 |
| Ac-CNBQx | 345, 405[a], 475[a] | 561 | 97 | 0.377 | 67→75 |
| Cz-CNBQx | 343, 430[a] | 558 | 89 | 0.352 | 78→87 |

[a]Shoulder peak

Example 8

Figure 5:
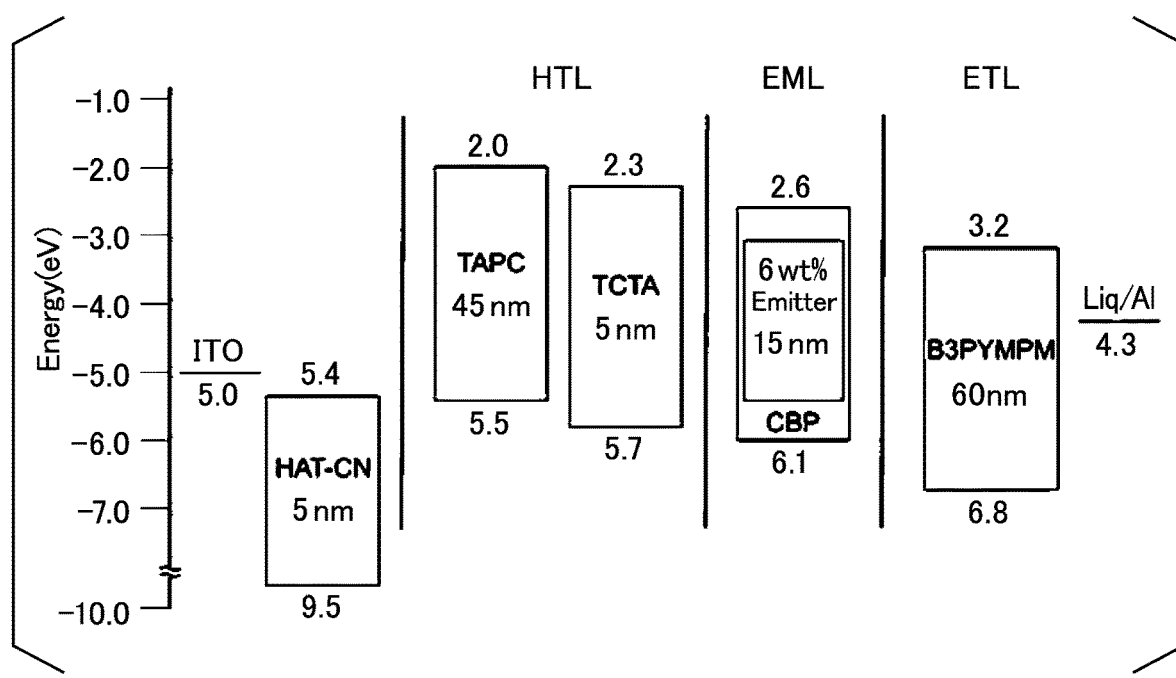
FIG. 5 is a drawing that indicates a constitution of organic electroluminescent elements prepared in Example 8.

A HAT-CN layer having a thickness of 5 nm, a TAPC layer having a thickness of 45 nm, a TCTA layer having a thickness of 5 nm, a light-emitting layer having a thickness of 15 nm, and a B3PYMPM layer having a thickness of 60 nm were laminated in this order by conducting vacuum evaporation (at $5.0 \times 10^{-4}$ Pa or less) on a glass substrate on which an anode composed of indium tin oxide (ITO) with a film thickness of 110 nm was formed (see FIG. 5).

Px-CNBQx, Da-CNBQx, the Ac-CNBQx, or Cz-CNBQx was used as a doping material of the light-emitting layer. The concentration of the doping material was set to be 6.0% by weight.

Then, an 8-hydroxy quinolinato lithium film having a thickness of 1 nm, and an aluminum film having a thickness of 80 nm were laminated in this order by a vacuum deposition method to form a cathode, and thus an organic electroluminescence element was obtained.

Figure 6:
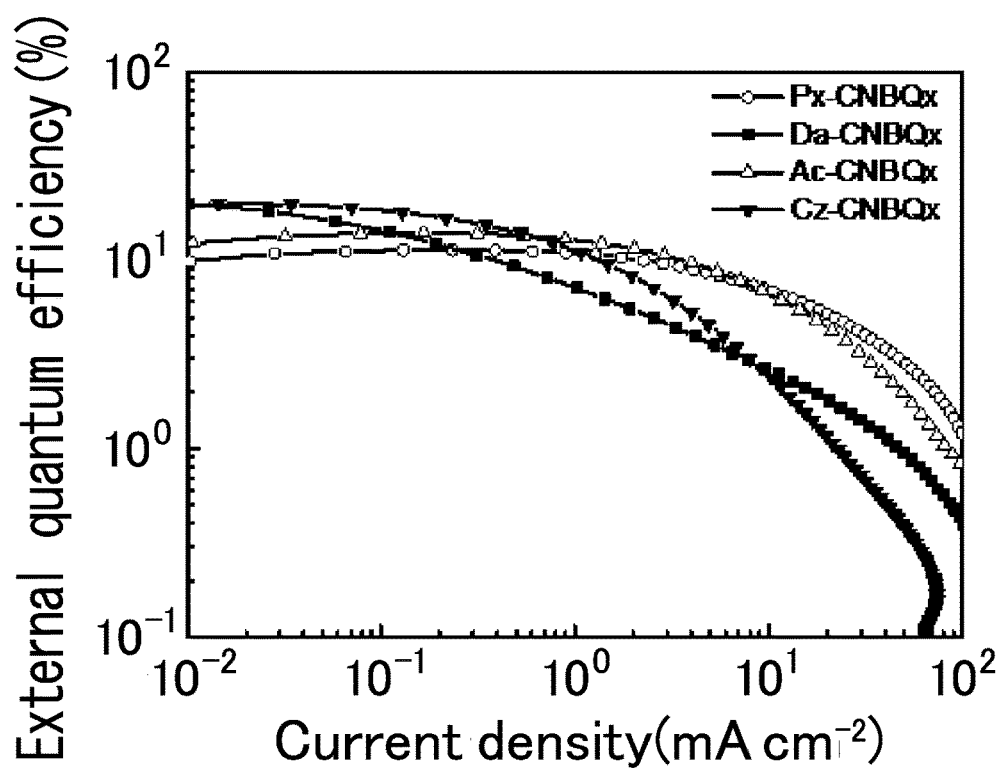
FIG. 6 is a drawing that indicates current density-external quantum efficiency characteristics of organic electroluminescent elements prepared in Example 8.
Figure 7:
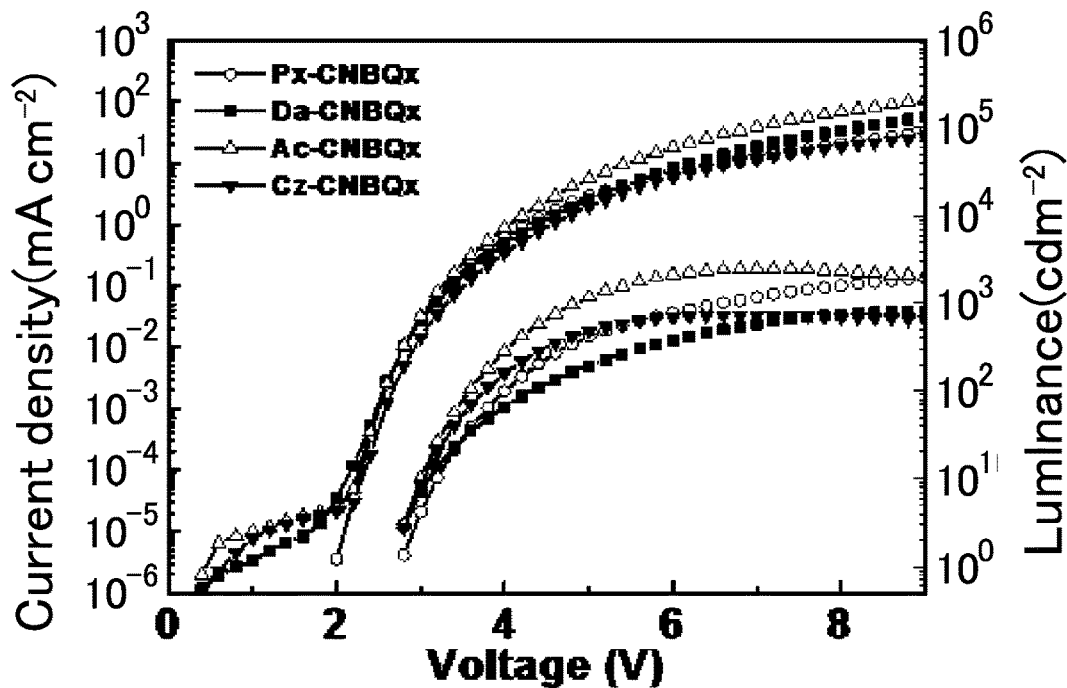
FIG. 7 is a drawing that indicates voltage-current density-emission intensity characteristic of organic electroluminescent elements prepared in Example 8.
Figure 8:
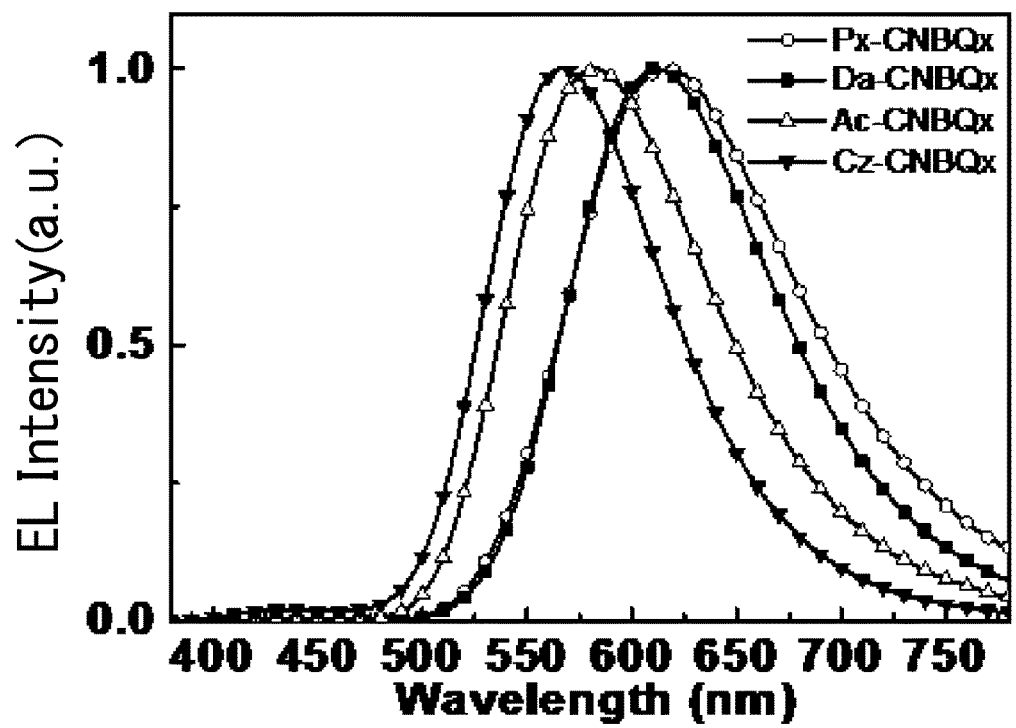
FIG. 8 is a drawing that indicates emission spectra of organic electroluminescent elements prepared in Example 8.
Figure 9:
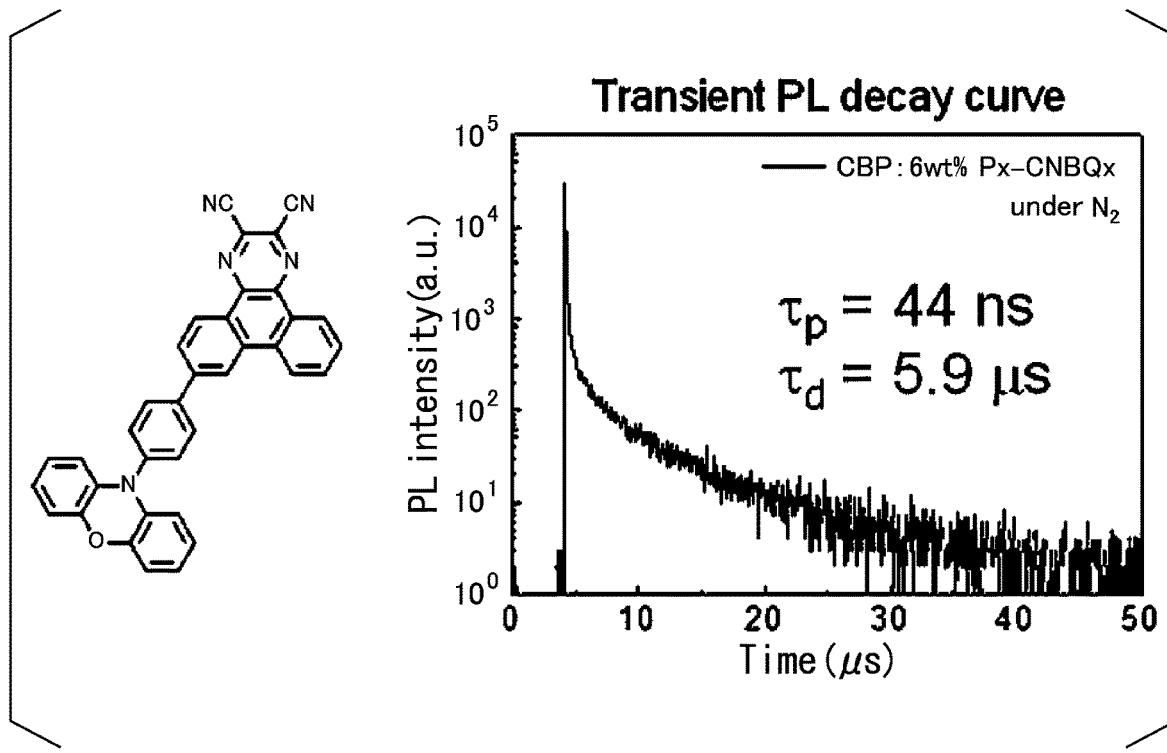
FIG. 9 is a drawing that indicates a transient decay curve of an organic photoluminescent element prepared using Px-CNBQx in a light-emitting layer in Example 8.
Figure 10:
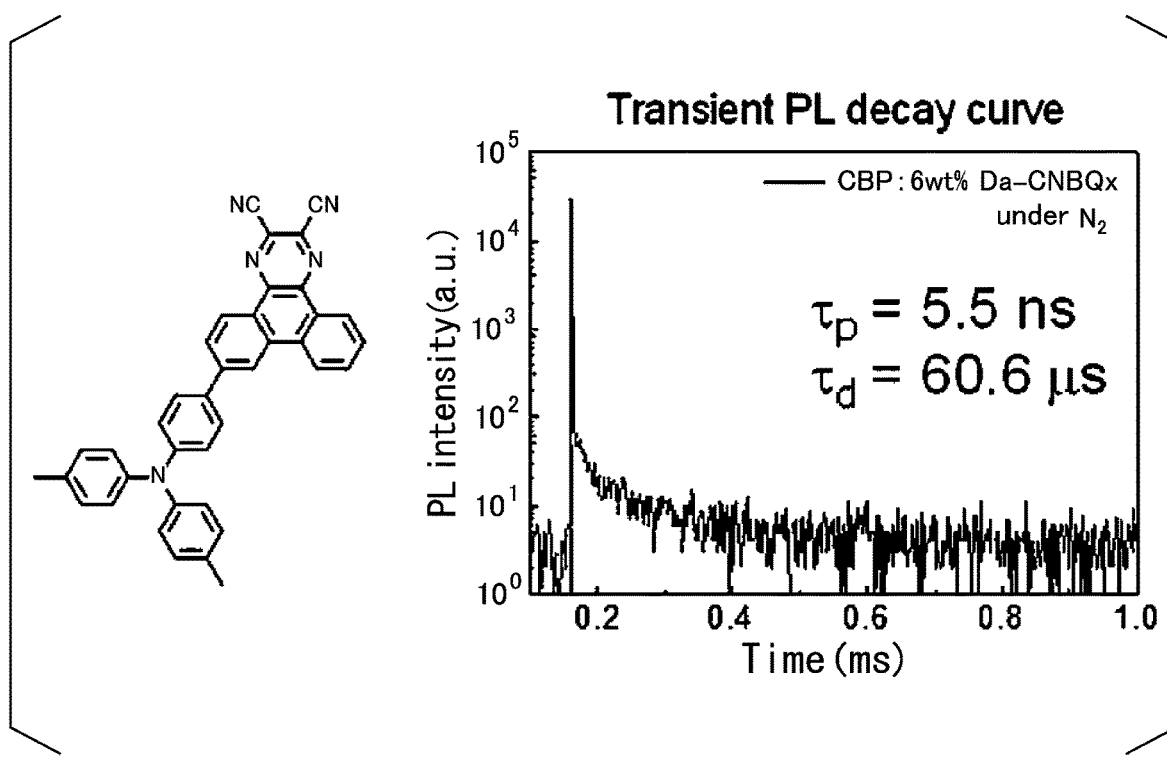
FIG. 10 is a drawing that indicates a transient decay curve of an organic photoluminescent element prepared using Da-CNBQx in a light-emitting layer in Example 8.
Figure 11:
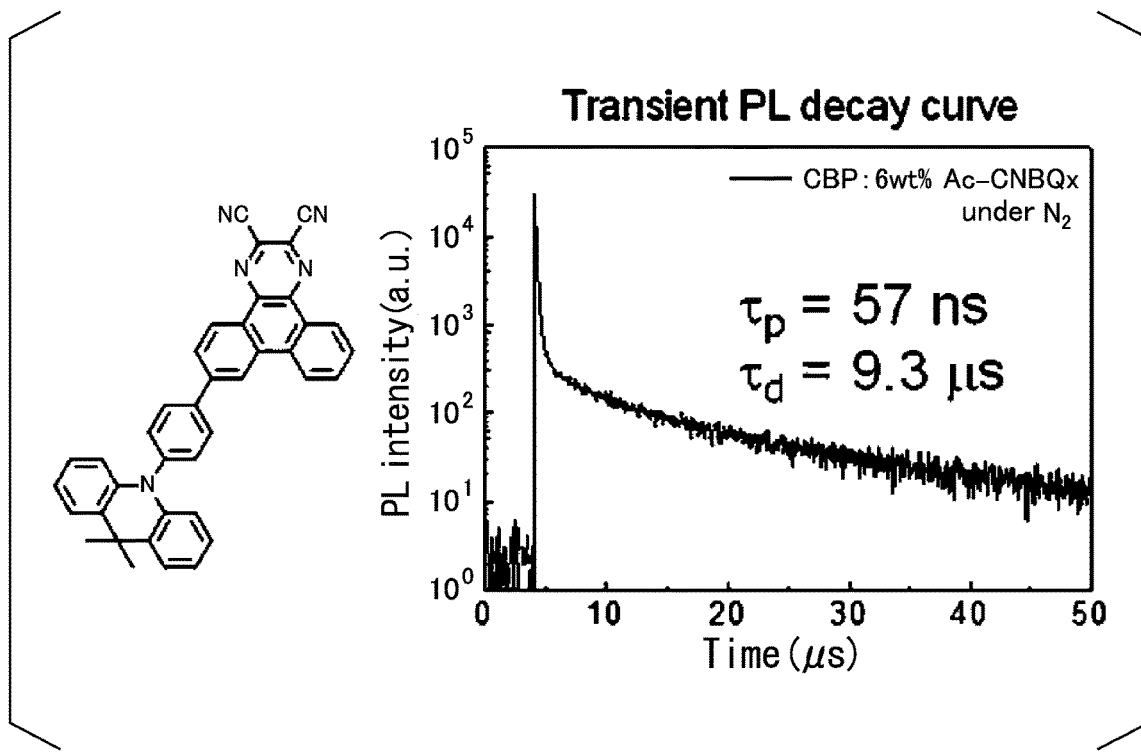
FIG. 11 is a drawing that indicates a transient decay curve of an organic photoluminescent element prepared using Ac-CNBQx in a light-emitting layer in Example 8.
Figure 12:
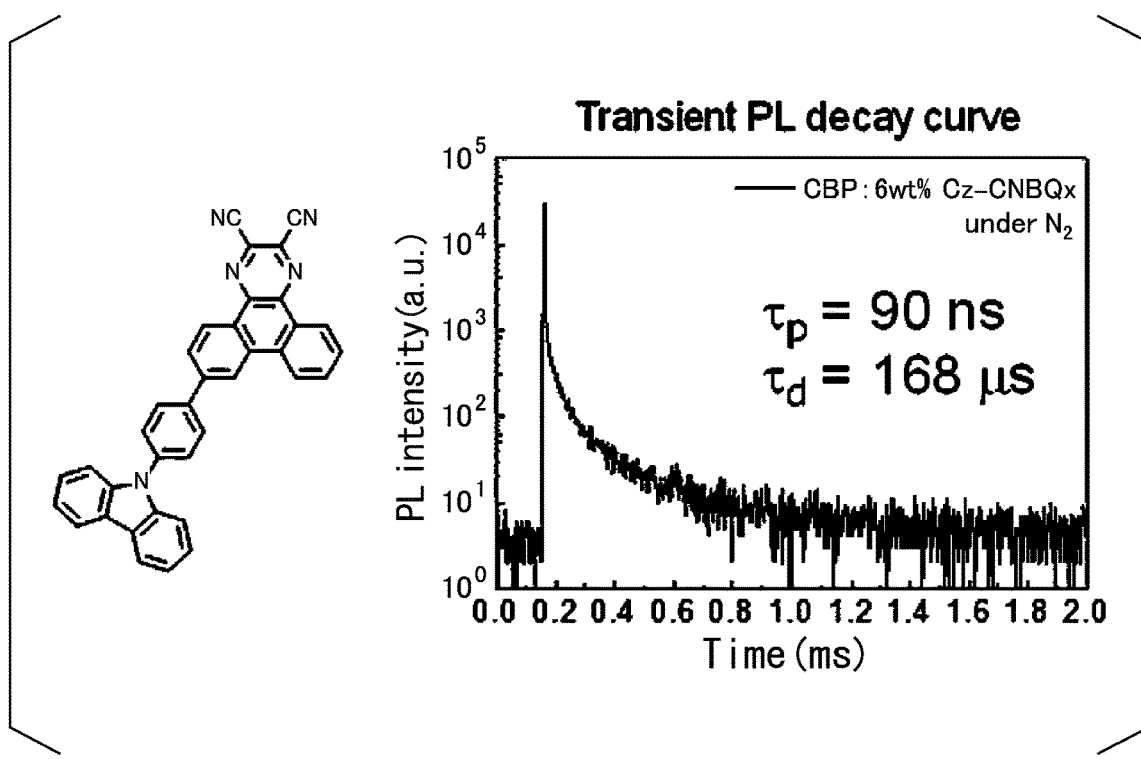
FIG. 12 is a drawing that indicates a transient decay curve of an organic photoluminescent element prepared using Cz-CNBQx in a light-emitting layer in Example 8.
Figure 13:
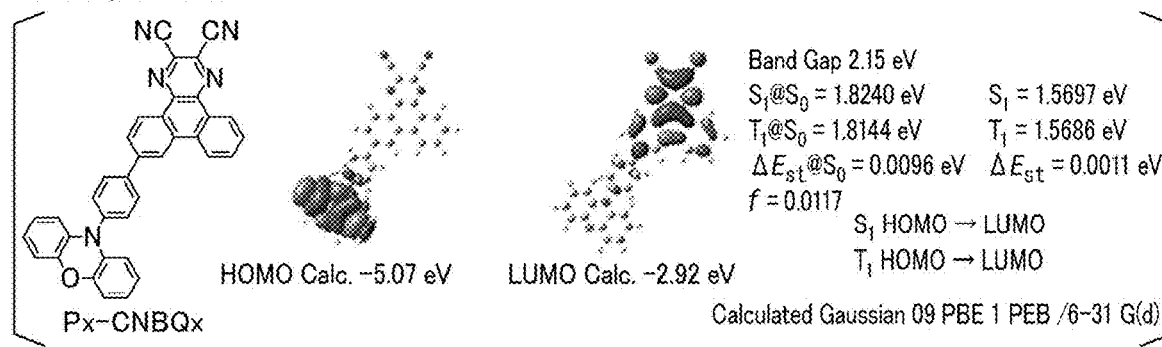
FIG. 13 is a drawing that indicates results of DFT calculation of Px-CNBQx.
Figure 14:
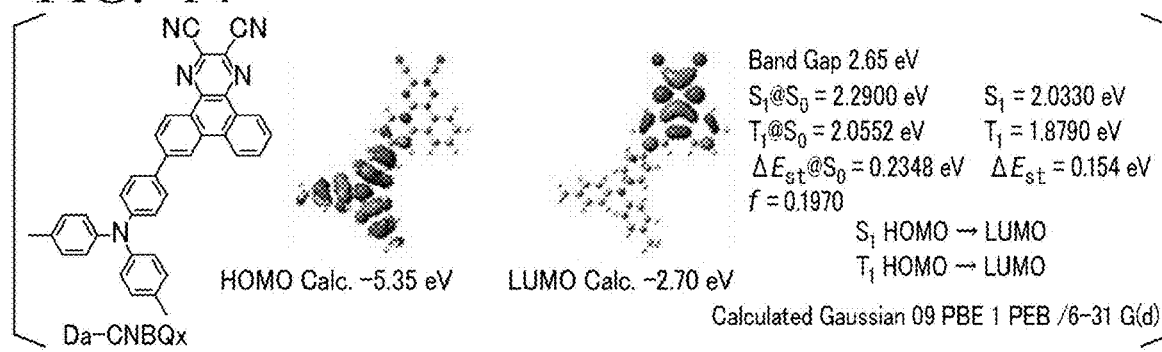
FIG. 14 is a drawing that indicates results of DFT calculation of Da-CNBQx.
Figure 15:
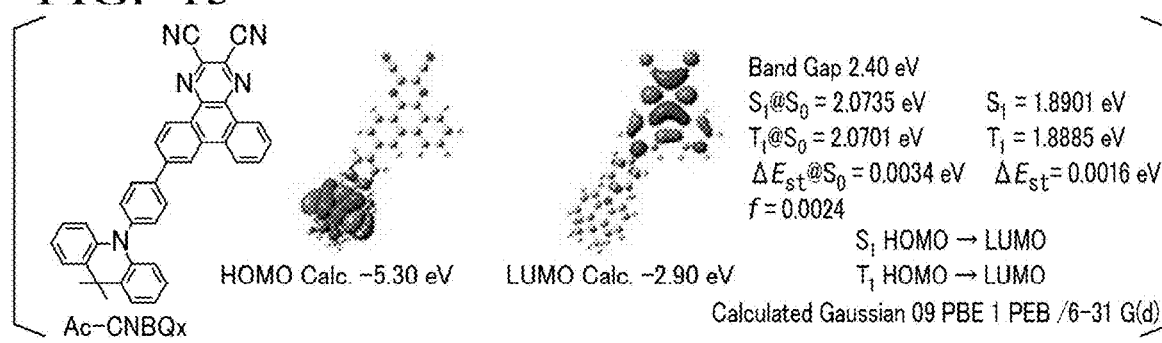
FIG. 15 is a drawing that indicates results of DFT calculation of Ac-CNBQx.
Figure 16:
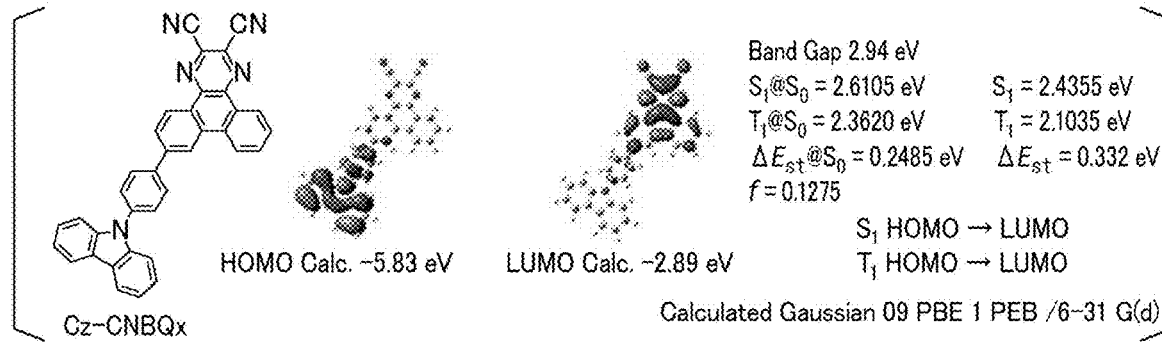
FIG. 16 is a drawing that indicates results of DFT calculation of Cz-CNBQx.
Figure 17:
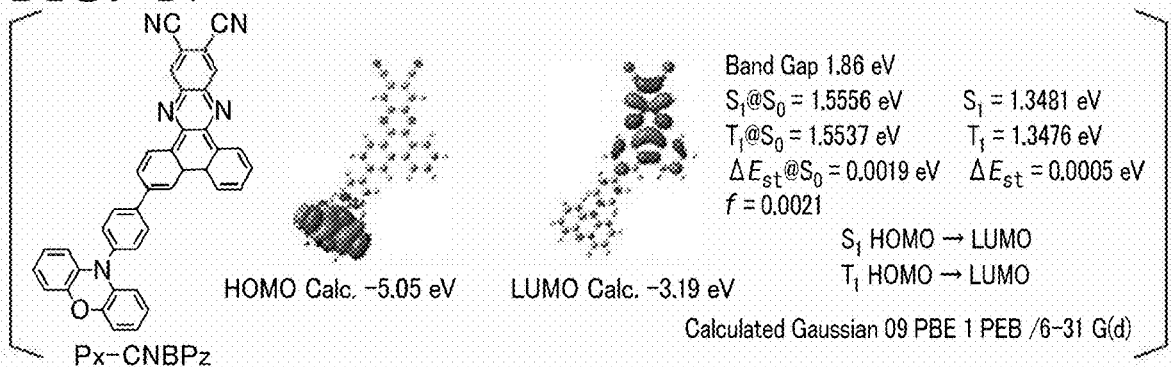
FIG. 17 is a drawing that indicates results of DFT calculation of Px-CNBPz.
Figure 18:
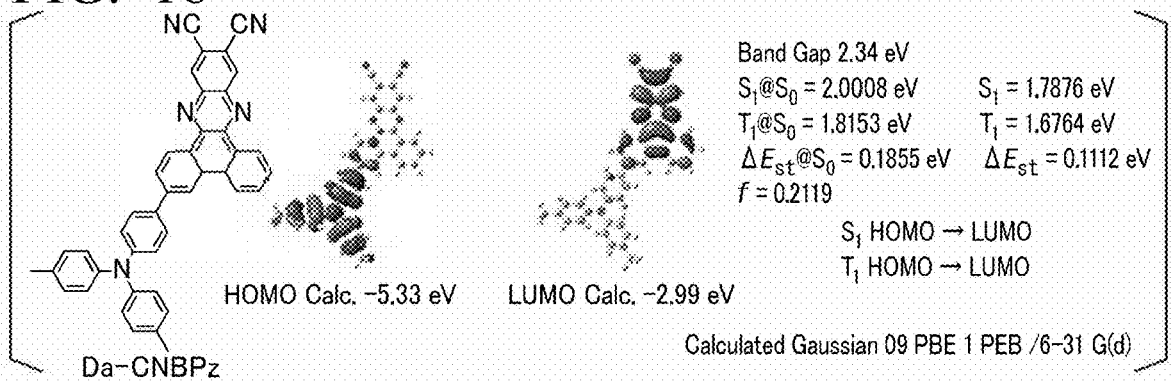
FIG. 18 is a drawing that indicates results of DFT calculation of Da-CNBPz.
Figure 19:
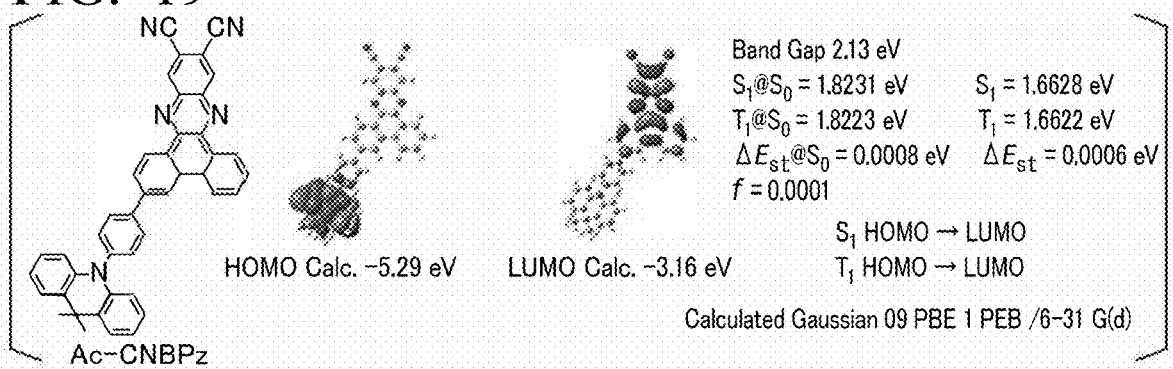
FIG. 19 is a drawing that indicates results of DFT calculation of Ac-CNBPz.
Figure 20:
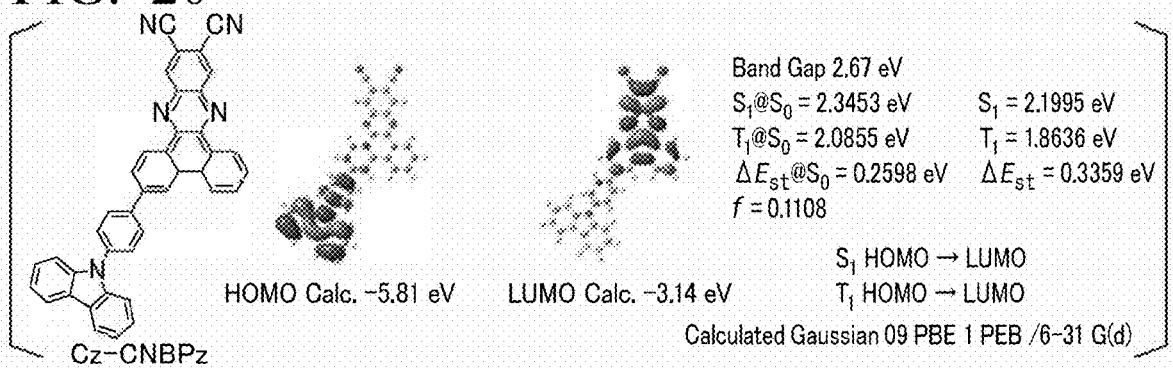
FIG. 20 is a drawing that indicates results of DFT calculation of Cz-CNBPz.

The characteristics of the organic electroluminescent element were measured. The luminescent spectra are shown in FIG. 8. The voltage-current density-luminescent intensity characteristics are shown in FIG. 7. The current density-external quantum efficiency characteristics are shown in FIG. 6. From the results shown in FIG. 8, the full-width at half-maximum, FWHM (μm), which was the wavelength width when the luminescent intensity became the half-value of the luminescent intensity peak, and the full-width at half-maximum, FWHM (eV), which was the energy width when the luminescent intensity became the half-value of the luminescent intensity peak, were obtained. In addition, from the results shown in FIG. 7, the luminescent start voltage (Vmax) and the maximum luminance (Lmax) were obtained. From the results shown in FIG. 6, the external quantum efficiency (EQE), the maximum external quantum efficiency (EQEmax), the maximum current efficiency (CEmax), and the maximum luminous efficiency (PEmax) were obtained. The results are shown in Table 3.

The transient decay curves of the organic photolumninescent elements are shown in FIGS. 9 to 12. The transient decay curves were obtained by measuring the process of deactivation of the luminous intensity when irradiation with excitation light having a wavelength of 340 nm was conducted, and indicated the luminescent lifetime. $\tau_p$ in FIGS. 9 to 12 indicates the luminescent lifetime of the instant fluorescent component, and $\tau_d$ indicates the luminescent lifetime of the delayed fluorescence component. As a result, in all of the organic photoluminescent elements, initial linear components (instant fluorescence components) were observed, and components which deviated from linearity after a few seconds (delayed fluorescence component) were observed. That is, it was confirmed that Px-CNBQx, Da-CNBQx, Ac-CNBQx and Cz-CNBQx were thermally-activated delayed fluorescence materials which exhibited delayed fluorescence components in addition to the instant fluorescence components.

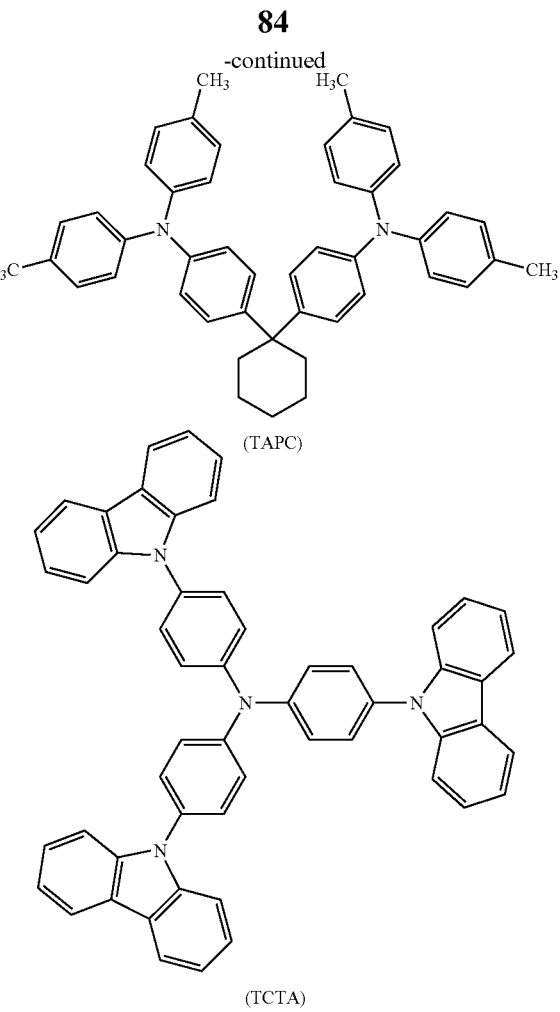

(TAPC)

(TCTA)

TABLE 3

| Compound in light-emitting layer | Luminescent peak wavelength $\lambda_{EL}$ [nm] | FWHM [nm] | FWHM [eV] | $V_{on}$ [V] | $L_{max}$ [cdm$^{-2}$] | $EQE_{max}$ | EQE 10 cdm$^{-2}$ [%] | EQE 100 cdm$^{-2}$ [%] | EQE 1000 cdm$^{-2}$ [%] | $CE_{max}$ [cdA$^{-1}$] | $PE_{max}$ [lmW$^{-1}$] |
|---|---|---|---|---|---|---|---|---|---|---|---|
| Px—CNBQx | 619 | 125 | 0.421 | 2.8 | 2261 | 11.4 | 11.2 | 11.2 | 7.1 | 16.5 | 15.5 |
| Da—CNBQx | 611 | 109 | 0.380 | 2.8 | 826 | 19.9 | 17.0 | 7.6 | — | 28.9 | 32.4 |
| Ac—CNBQx | 584 | 106 | 0.408 | 2.8 | 2449 | 14.0 | 10.1 | 13.9 | 9.6 | 34.0 | 33.3 |
| Cz—CNBQx | 567 | 97 | 0.378 | 2.8 | 726 | 20.0 | 19.9 | 17.0 | — | 54.9 | 61.7 |

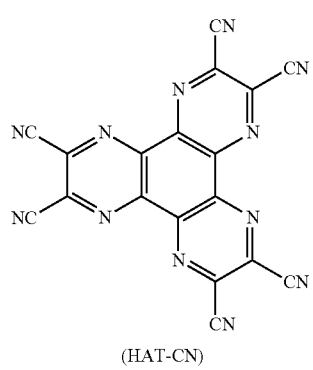

(HAT-CN)

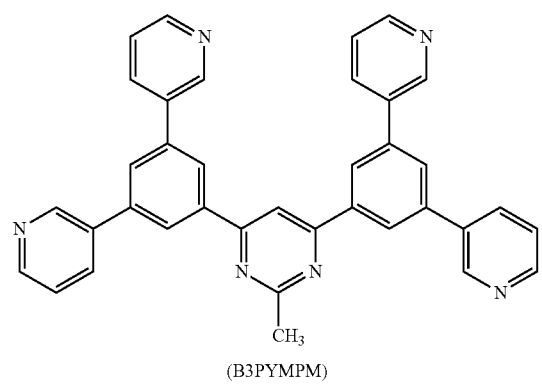

(B3PYMPM)

Example 9

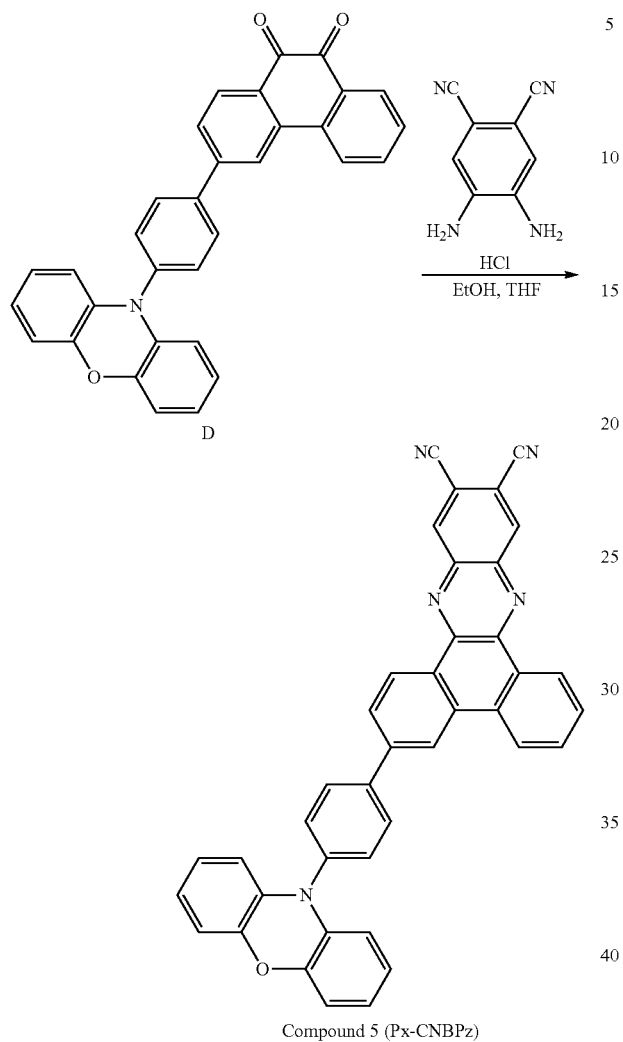

Compound 5 (Px-CNBPz)

The compound D was prepared in the same manner as that in Example 1.

The compound D (0.30 g, 0.64 mmol), 4,5-diaminophthalonitrile (0.12 g, 0.77 mmol), 40 mL of ethanol, 40 mL of THF, and 1 mL of 12M hydrochloric acid were charged in a three-necked flask having a capacity of 300 mL, the temperature in the reaction system was set at 40° C., and then the mixture was stirred while conducting heating for 18 hours.

The precipitated solid was collected by filtration, washed with water and methanol and then dried. The resultant solid was purified by gel permeation chromatography to obtain a dark red solid (yield amount: 0.20 g, yield: 53%).

The chemical shift values (δ) of the compound measured by $^1$H NMR were as follows: $^1$H NMR δ 9.45 (d, J=8.5 Hz, 1H), 9.38 (dd, J=8.0, 1.2 Hz, 1H), 8.84 (d, J=1.6 Hz, 1H), 8.80 (d, J=2.0 Hz, 2H), 8.71 (d, J=8.0 Hz, 1H), 8.10 (dt, J=8.0, 1.8 Hz, 3H), 7.98-7.92 (m, 1H), 7.88-7.82 (m, 1H), 7.63 (dt, J=8.7, 2.0 Hz, 2H), 6.78-6.57 (m, 4H), 6.21 (d, J=8.5 Hz, 1H), 6.17-6.08 (m, 3H). It was confirmed by $^1$H NMR measurement that the obtained compound was compound 5 (Px-CNBPz).

Example 10

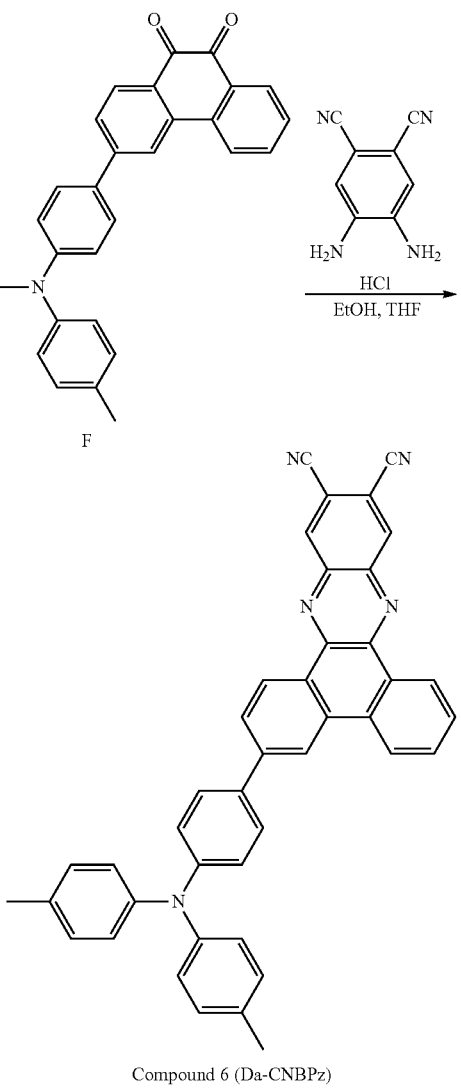

Compound 6 (Da-CNBPz)

The compound F was prepared in a similar manner to that of Example 2.

The compound F (1.00 g, 2.1 mmol), 4,5-diaminophthalonitrile (0.40 g, 2.5 mmol), 40 mL of ethanol, 40 mL of THF, and 1 mL of 12M hydrochloric acid were charged in a three-necked flask having a capacity of 300 mL, the temperature in the reaction system was set at 40° C., and then the mixture was stirred while conducting heating for 15 hours. The precipitated solid was collected by filtration, washed with water and methanol and then dried. The resultant solid was purified by sublimation purification to obtain a red solid (yield amount: 0.94 g, yield ratio: 75%).

The chemical shift values (δ) of the compound measured by $^1$H NMR (400 MHz, CDCl$_3$) were as follows: δ 9.34 (m, 2H), 8.77 (m, J=2.8 Hz, 2H), 8.71 (d, J=1.6 Hz, 1H), 8.65 (d, J=8.0 Hz, 1H), 7.98 (dd, J=8.4, 1.6 Hz, 1H), 7.94-7.90 (m, 1H), 7.83-7.79 (m, J=7.6, 1.0 Hz, 1H), 7.68 (dt, J=9.4, 2.4 Hz, 2H), 7.19 (dt, J=9.2, 2.4 Hz, 2H), 7.16-7.07 (m, 8H), 2.37 (s, 6H). It was confirmed by $^1$H NMR measurement that the obtained compound was compound 6 (Da-CNBPz).

Example 11

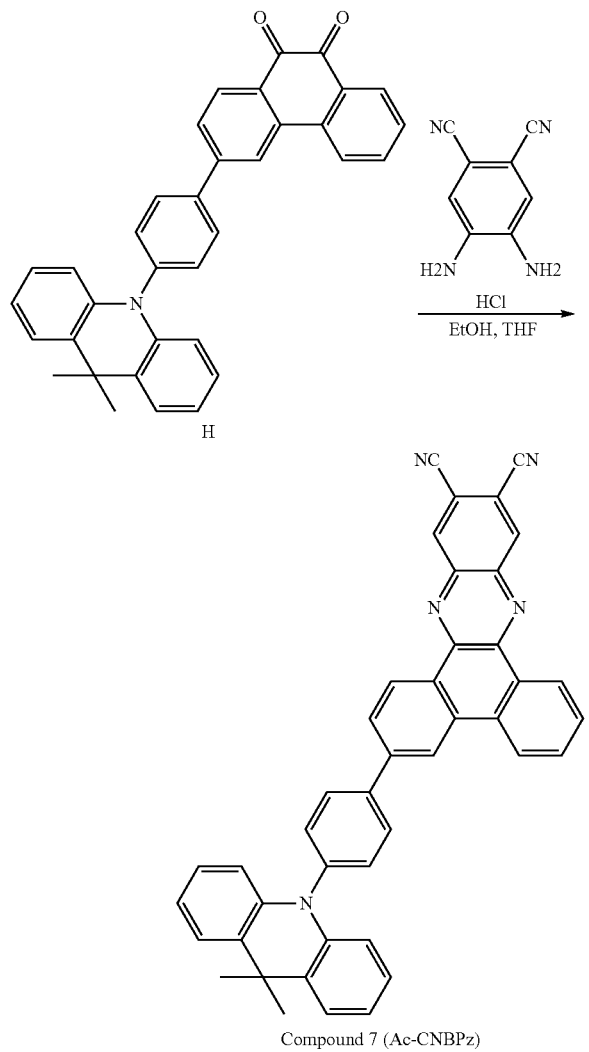

Compound 7 (Ac-CNBPz)

The compound H was prepared in a similar manner to that of Example 3.

The compound H (0.80 g, 1.6 mmol), 4,5-diaminophthalonitrile (0.31 g, 2.0 mmol), 40 mL of ethanol, 40 mL of THF, and 1 mL of 12M hydrochloric acid were charged in a three-necked flask having a capacity of 300 mL, the temperature of the reaction system was set at 40° C., and then the mixture was stirred while conducting heating for 18 hours. The precipitated solid was collected by filtration, washed with water and methanol, and then dried. The resultant solid was purified by gel permeation chromatography to obtain a yellow solid (yield amount: 0.77 g, yield: 34%).

The chemical shift values (δ) of the compound measured by $^1$H NMR (400 MHz, CDCl$_3$) were as follows: δ 9.48 (d, J=8.4 Hz, 1H), 9.41 (dd, J=8.0, 1.2 Hz, 1H), 8.89 (d, J=1.6 Hz, 1H), 8.85 (d, J=2.4 Hz, 2H), 8.74 (d, J=7.8, 1H), 8.14 (dd, J=8.4, 1.6 Hz, 1H), 8.10 (dt, J=8.8, 2.2 Hz, 2H), 8.00-7.92 (m, 1H), 7.87-7.94 (m, 1H), 7.56 (d, J=8.4 Hz, 2H), 7.53-7.48 (m, 2H), 7.06-6.91 (m, 4H), 6.41 (dd, J=8.0, 1.2 Hz, 2H), 1.74 (s, 6H). It was confirmed by $^1$H NMR measurement that the obtained compound was compound 7 (Ac-CNBPz).

Example 12

Figure 21:
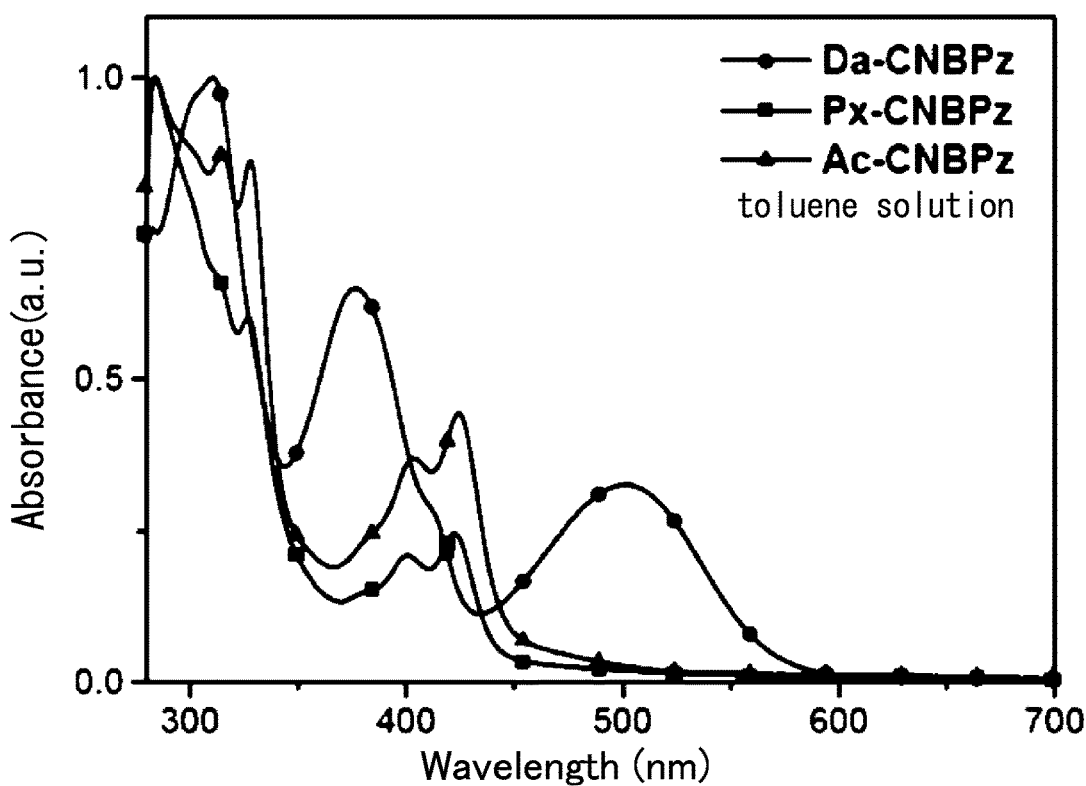
FIG. 21 is a drawing that indicates absorption spectra of a Px-CNBPz toluene solution, a Da-CNBPz toluene solution, and an Ac-CNBPz toluene solution, prepared in Example 12.
Figure 22:
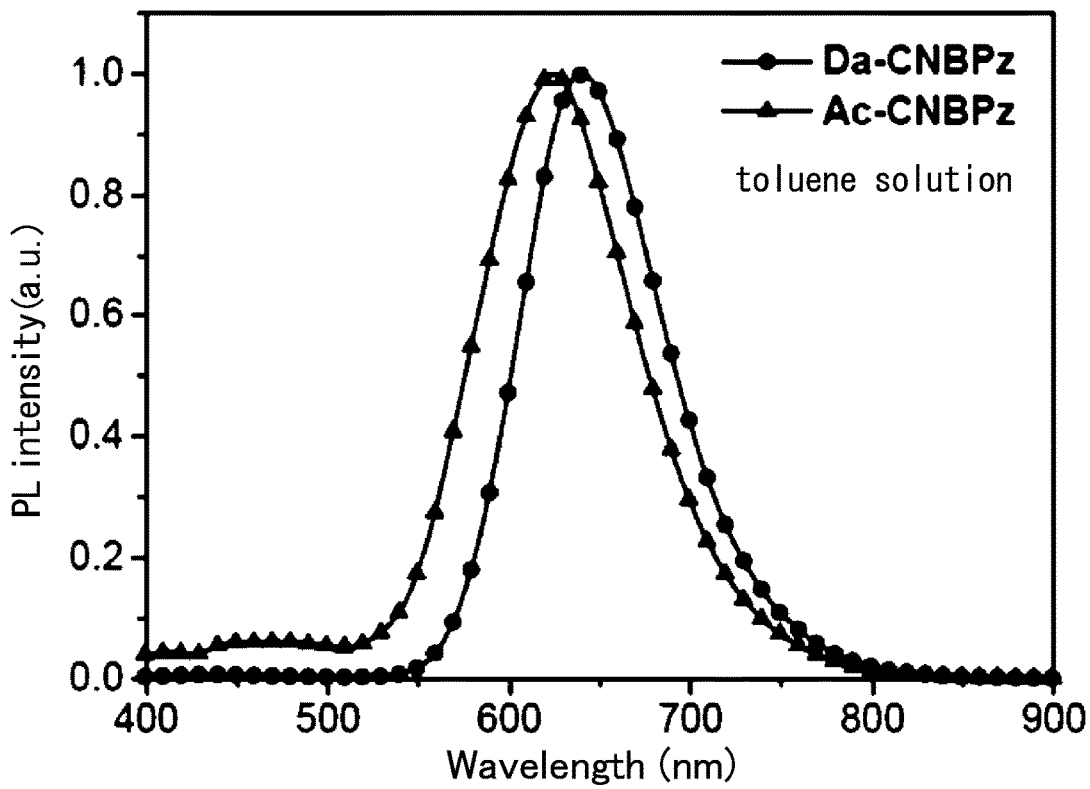
FIG. 22 is a drawing that indicates emission spectra of a Px-CNBPz toluene solution, a Da-CNBPz toluene solution, and an Ac-CNBPz toluene solution, prepared in Example 12.

In a glove box under an argon atmosphere, a toluene solution of the compound 5 (Px-CNBPz), a toluene solution of the compound 6 (Da-CNBPz), and a toluene solution of the compound 7 (Ac-CNBPz) were prepared. The luminescent spectrum, the absorption spectrum, and the quantum yield ($\varphi_{PL}$) of the solutions were measured by applying excitation light having a wavelength of 340 nm thereto. The results are shown in FIGS. 21 and 22 and Table 4.

Example 13

Figure 23:
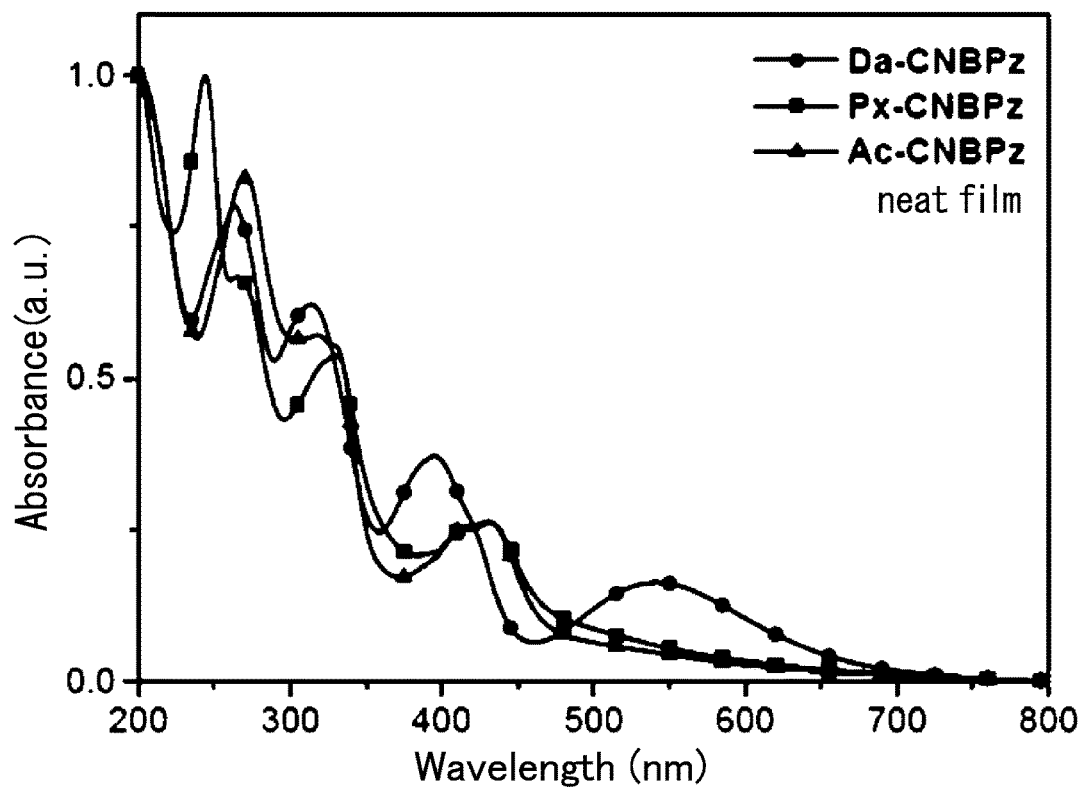
FIG. 23 is a drawing that indicates absorption spectra of organic photoluminescent elements prepared in Example 13.

The compound 5 (Px-CNBPz), the compound 6 (Da-CNBPz), and the compound 7 (Ac-CNBPz) were used as evaporation sources at a vacuum degree of 10$^{-4}$ Pa or less and deposited on quartz substrates, and thus organic photoluminescent elements each having a thin film (neat film) with a thickness of 100 nm were obtained. The absorption spectrum of these organic photoluminescent elements was measured. In addition, the levels of the highest occupied molecular orbital (HOMO) and the lowest unoccupied molecular orbital (LUMO) were obtained from the photoelectron yield spectroscopy and the absorption spectroscopy to obtain a HOMO-LUMO energy gap (Eg). The results are shown in FIG. 23 and Table 4.

TABLE 4

| Compound | Absorbance peak length $\lambda_{abs}$[nm] Example 13 | Luminescence peak length $\lambda_{PL}$[nm] Example 13/ Example 14 | $\Phi_{PL}$[%] Example 13/ Example 14 | HOMO [eV] | LUMO [eV] | $E_g$ [eV] |
|---|---|---|---|---|---|---|
| Da—CNBPz | 311, 376, 410$^{a)}$, 501 | 640/688 | 85/72 | −5.5 | −3.5 | 2.0 |
| Px—CNBPz | 284, 300, 327, 401, 422, 500$^{a)}$ | —$^{b)}$/637 | <1/41 | −5.5 | −3.5 | 2.0 |
| Ac—CNBPz | 284, 300$^{f)}$, 328, 403, 424, 470$^{a)}$ | 624/615 | 31/67 | −5.7 | −3.6 | 2.1 |

$^{a)}$Shoulder peak
$^{b)}$Unmeasured

Example 14

Figure 24:
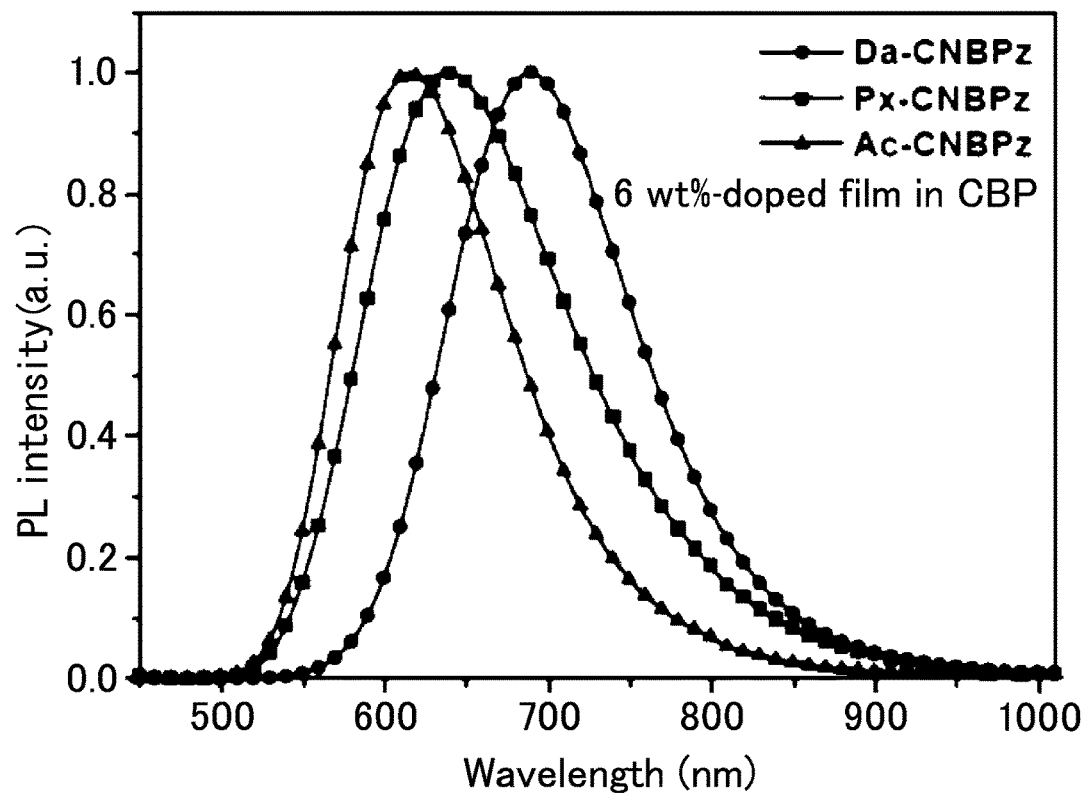
FIG. 24 is a drawing that indicates emission spectra of organic photoluminescent elements prepared in Example 14.

A combination of CBP and the compound 5 (Px-CNBPz), that of CBP and the compound 6 (Da-CNBPz), and that of CBP and the compound 7 (Ac-CNBPz) were used as evaporation sources and deposited on quartz substrates at 10$^{-4}$ Pa or less, and thus organic photoluminescent elements, each having a concentration of the compound 5 (Px-CNBPz), the compound 6 (Da-CNBPz), or the compound 7 (Ac-CNBPz) of 6.0% by weight, and a thin film with a thickness of 100 nm, were obtained. The luminescent spectrum of these organic photoluminescent elements was measured by applying excitation light having a wavelength of 340 nm thereto. The results are shown in FIG. 24.

Example 15

A HAT-CN layer having a thickness of 5 nm, a TAPC layer having a thickness of 45 nm, a TCTA layer having a thickness of 5 nm, a light-emitting layer having a thickness of 15 nm, and a B3PYMPM layer having a thickness of 60 nm were laminated in this order by conducting vacuum evaporation (at $5.0 \times 10^{-4}$ Pa or less) on a glass substrate on which an anode made of indium tin oxide (ITO) was formed with a thickness of 110 nm.

The compound 5 (Px-CNBPz), the compound 6 (Da-CNBPz), or the compound 7 (Ac-CNBPz) was used as a doping material of the light-emitting layer. The concentration of the doping material was set to be 6.0% by weight.

Then, an 8-hydroxy quinolinato lithium film having a thickness of 1 nm, and an aluminum film having a thickness of 80 nm were laminated in this order by a vacuum deposition method to form a cathode, and thus an organic electroluminescence element was obtained.

Figure 25:
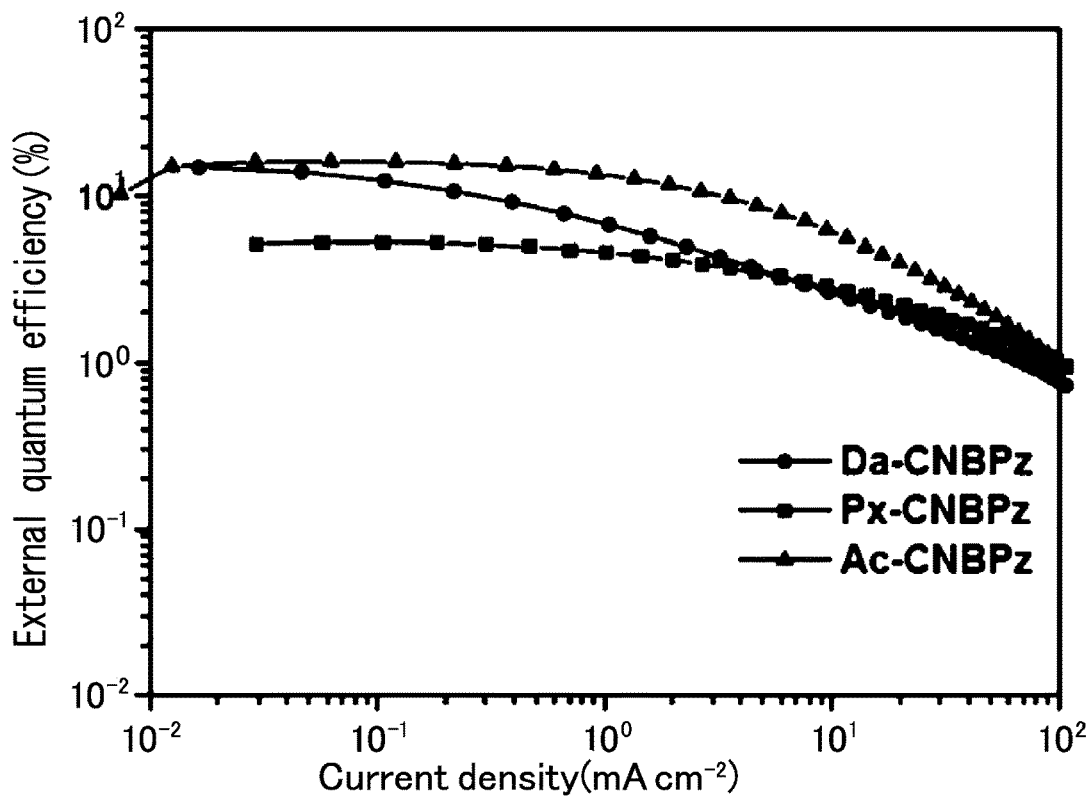
FIG. 25 is a drawing that indicates current density-external quantum efficiency characteristics of organic electroluminescent elements prepared in Example 15.
Figure 26:
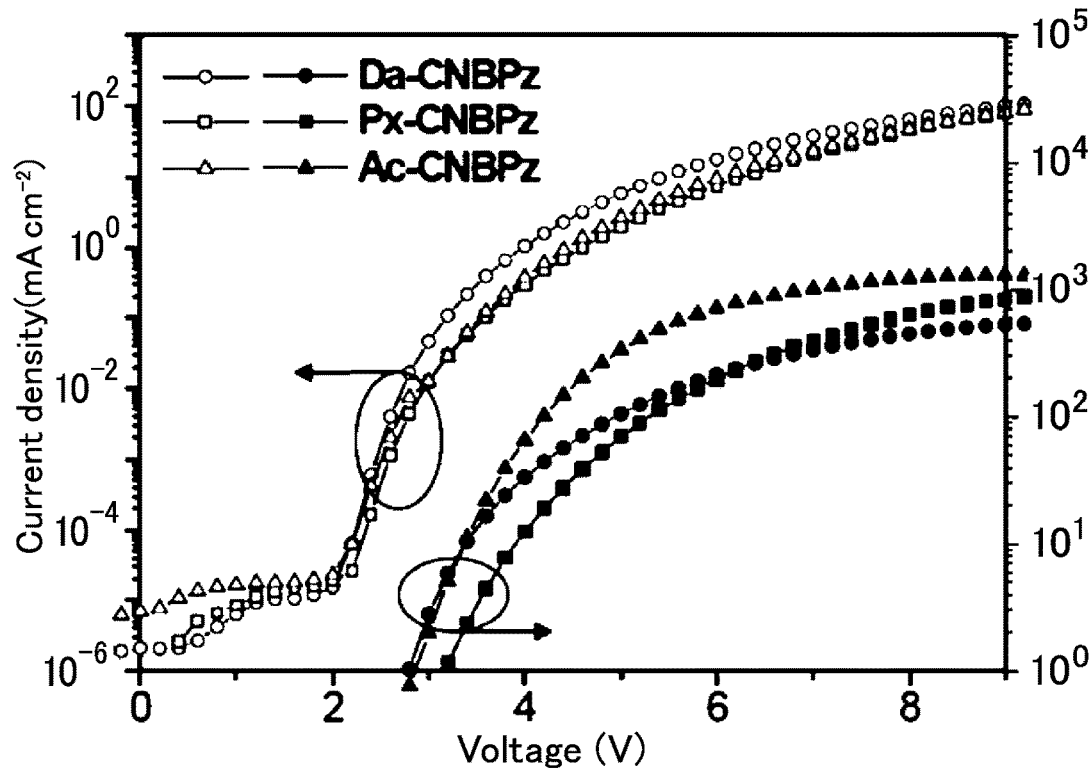
FIG. 26 is a drawing that indicates voltage-current density-emission intensity characteristics of organic electroluminescent elements prepared in Example 15.
Figure 27:
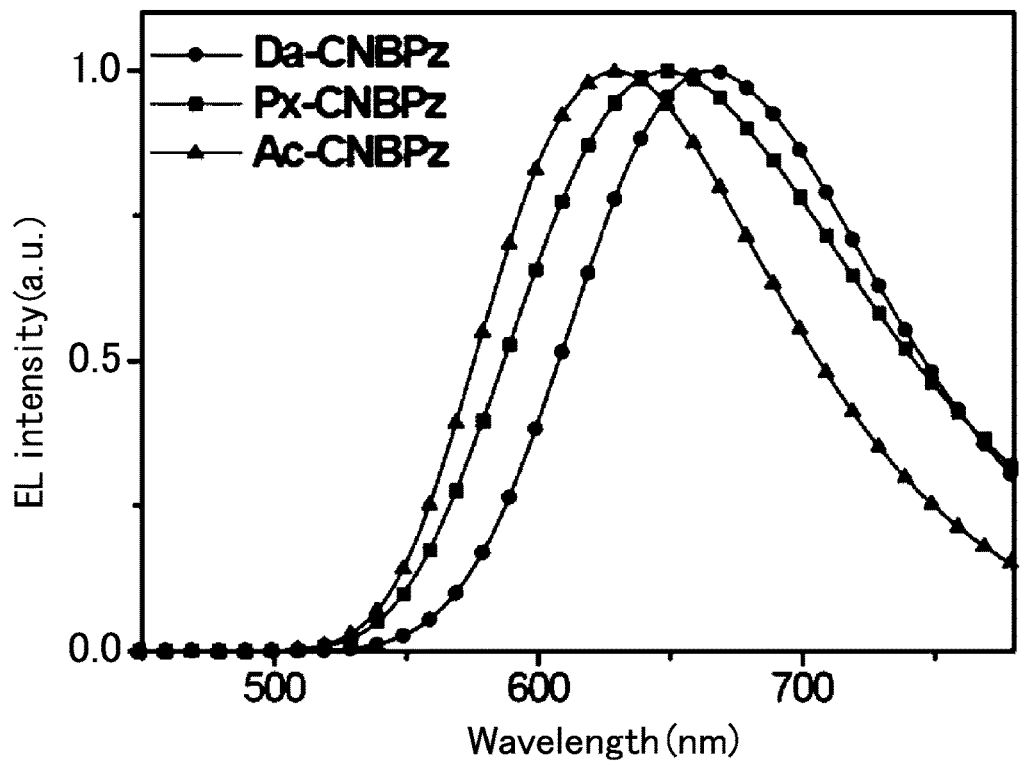
FIG. 27 is a drawing that indicates emission spectra of organic electroluminescent elements prepared in Example 15.

The characteristics of the organic electroluminescent element were measured. The luminescent spectra are shown in FIG. 27. The voltage-current density-luminescent intensity characteristics are shown in FIG. 26. The current density-external quantum efficiency characteristics are shown in FIG. 25. From the results shown in FIG. 27, the full-width at half-maximum, FWHM (μm), which is the wavelength width when the luminescent intensity became the half-value of the luminescent intensity peak, and the full-width at half-maximum, FWHM (eV), which is the energy width when the luminescent intensity became the half-value of the luminescent intensity peak, were obtained. In addition, from the results shown in FIG. 26, the luminescent start voltage (Vmax) and the maximum luminance (Lmax) were obtained. From the results shown in FIG. 25, the external quantum efficiency (EQE), the maximum current efficiency (CEmax), and the maximum luminous efficiency (PEmax) were obtained. In addition, the chromaticity (CIE chromaticity coordinates) were obtained from EL spectra at a current density of 10 mA cm$^{-2}$. The results are shown in Table 5.

Figure 28:
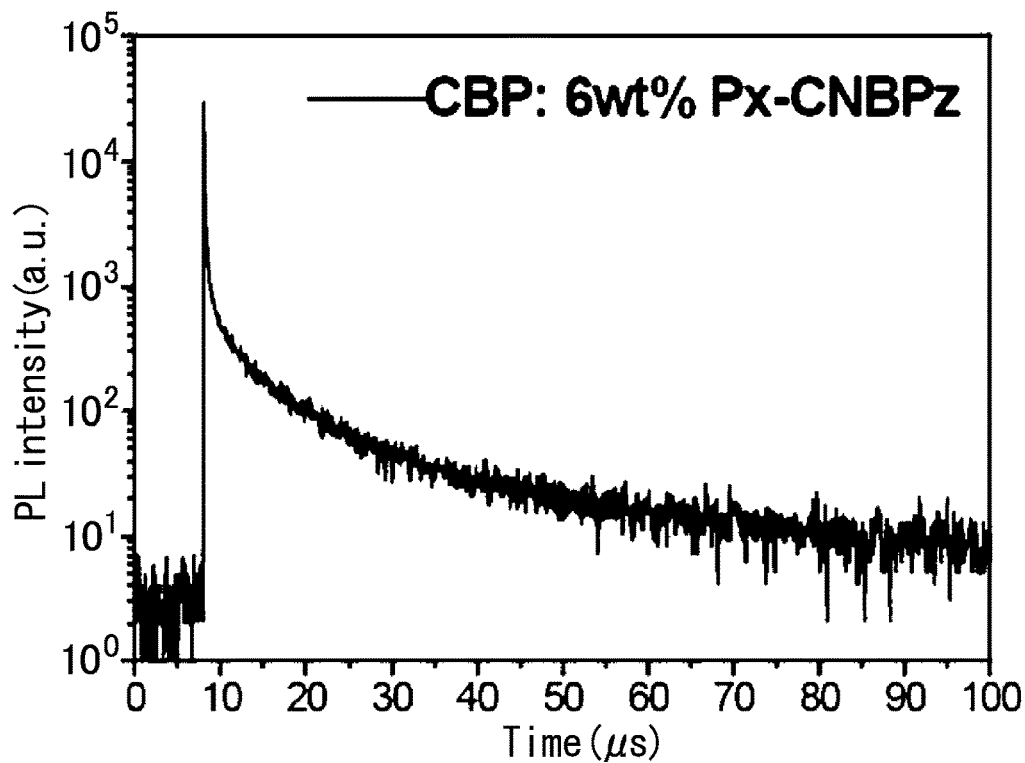
FIG. 28 is a drawing that indicates a transient decay curve of an organic photolunminescent element prepared using Px-CNBPz in a light-emitting layer in Example 15.
Figure 29:
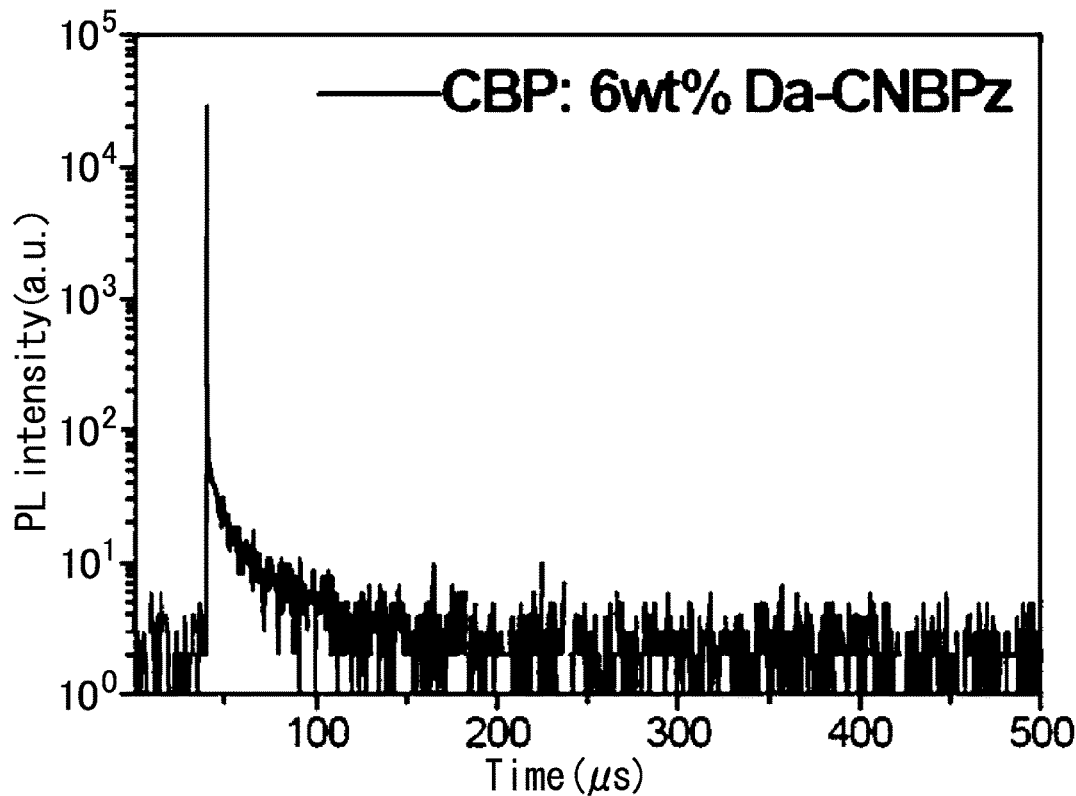
FIG. 29 is a drawing that indicates a transient decay curve of an organic photolunminescent element prepared using Da-CNBPz in a light-emitting layer in Example 15.
Figure 30:
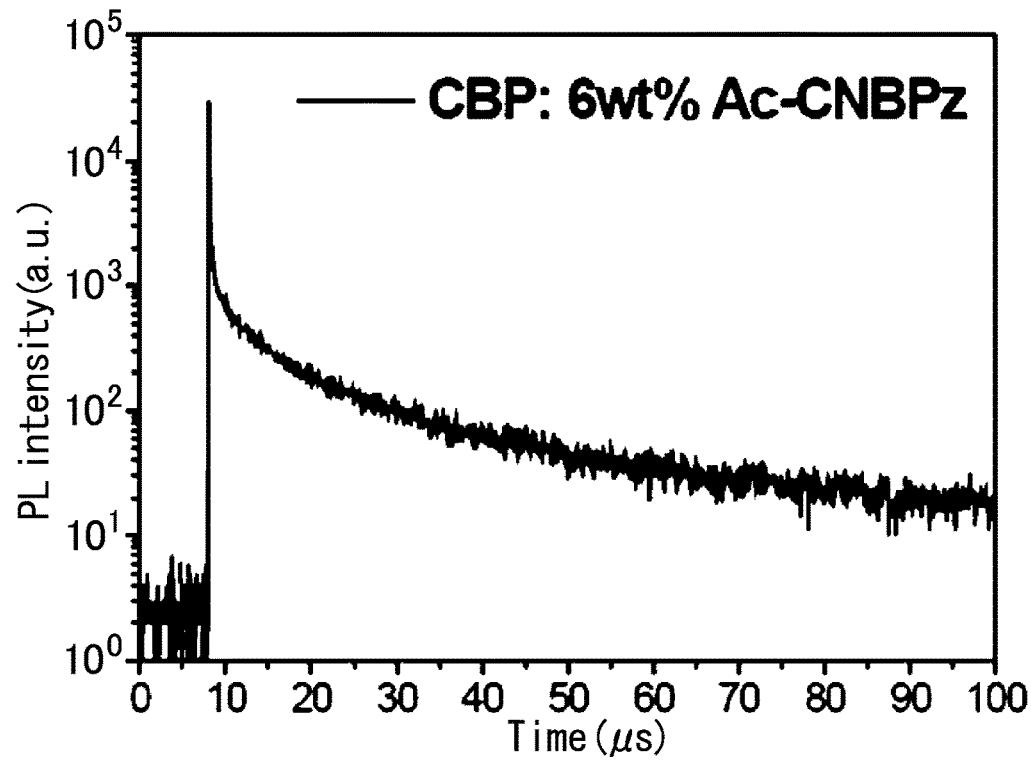
FIG. 30 is a drawing that indicates a transient decay curve of an organic photolunminescent element prepared using Ac-CNBPz in a light-emitting layer in Example 15.

The transient decay curves of the organic photoluminescent elements are shown in FIGS. 28 to 30, and the results of the luminescent lifetime obtained therefrom are shown in Table 6. In table 6, $\varphi_p$ indicates the quantum yield of the instant fluorescent component, $\varphi_d$ indicates the quantum yield of the delayed fluorescent component, $\tau_p$ indicates the luminescent lifetime of the instant fluorescent component, and $\tau_d$ indicates the luminescent lifetime of the delayed fluorescence component. As a result, in all of the organic photoluminescent elements, initial linear components (instant fluorescence components) were observed, and components which deviated from linearity after a few μ seconds (delayed fluorescence components) were observed. Thus, it was confirmed that the compound 5 (Px-CNBPz), the compound 6 (Da-CNBPz), and the compound 7 (Ac-CNBPz) were thermally-activated delayed fluorescence materials which exhibited delayed fluorescence components in addition to the instant fluorescence components.

TABLE 5

| Compound in light-emitting layer | Luminescent peak wavelength $\lambda_{EL}$ [nm] | FWHM [nm] | FWHM [eV] | Von [V] | Lmax (cd m$^{-2}$) |
|---|---|---|---|---|---|
| Da-CNBPz | 666 | 139 | 0.377 | 2.8 | 540 |
| Px-CNBPz | 648 | 158 | 0.441 | 3.2 | 949 |
| Ac-CNBPz | 630 | 132 | 0.402 | 2.8 | 1305 |

| Compound in light-emitting layer | EQE [%] Max/10 cd m$^{-2}$/100 cd m$^{-2}$/1000 cd m$^{-2}$ | CEmax [cd A$^{-1}$] | PEmax [lm W$^{-1}$] | CIE 10 mA cm$^{-2}$ |
|---|---|---|---|---|
| Da-CNBPz | 14.9/10.7/3.4/— | 6.23 | 6.99 | (0.65, 0.35) |
| Px-CNBPz | 5.32/5.2/3.8/— | 4.19 | 3.84 | (0.62, 0.38) |
| Ac-CNBPz | 16.2/16.2/14.5/3.57 | 18.23 | 17.16 | (0.61, 0.39) |

TABLE 6

| Compound | $\Phi_p$ [%] | $\Phi_d$ [%] | $\tau_p$ [ns] | $\tau_d$ [us] |
|---|---|---|---|---|
| Da-CNBPz | 61 | 11 | 10 | 49 |
| Px-CNBPz | 15 | 26 | 29 | 2.0 |
| Ac-CNBPz | 14 | 53 | 28 | 6.9 |

The density functional (DFT) calculation was conducted regarding compounds 1 to 8. The results are shown in FIGS. 13 to 20.

Light-emitting material containing a compound of formula (I) exhibited high EL emission characteristics by the evaluation based on thermally-activated delayed fluorescence (TADF). The maximum current efficiency CEmax and the maximum luminous efficiency PEmax were high. The compounds of formula (I) are promising materials as a TADF luminescent material.

INDUSTRIAL APPLICABILITY

The dicyano N-heterocyclic compound according to the present invention is useful as a light-emitting material, and the light-emitting element containing the light-emitting material according to the present invention may achieve excellent luminous efficiency.

The invention claimed is:
1. A compound of formula (I):

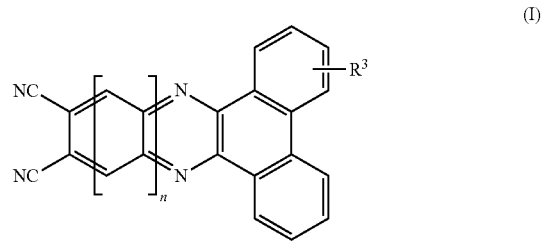

in formula (I), R$^3$ represents a phenyl group having a substituent, and the substituent is a hetero ring in which at least two substituted or unsubstituted aromatic rings are condensed, or a substituted or unsubstituted diarylamino group, and n represents a number of repetitions of a content in brackets and is 0 or 1.

2. The compound according to claim 1, wherein R$^3$ is at least one selected from the group consisting of groups of formula (d1) to formula (d4):

(d1)

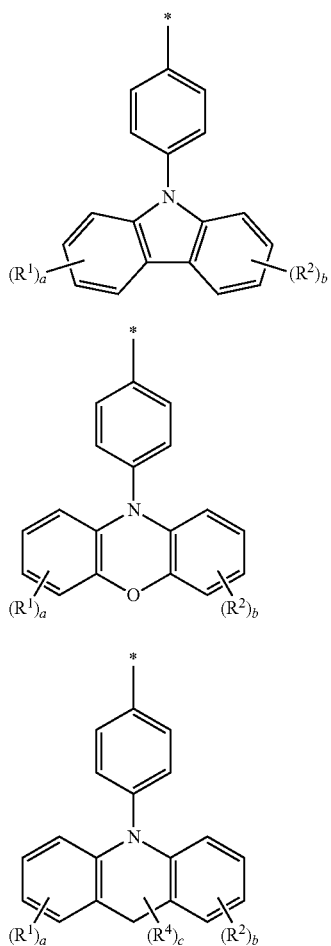

(d2)

(d3)

(d4)

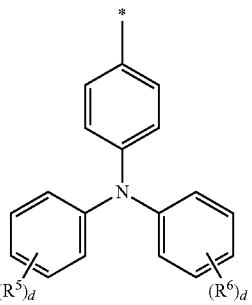

in the formulae (d1) to (d4), $R^1$, $R^2$, $R^4$, $R^5$ and $R^6$ each independently represents a substituent; a and b each independently represents the number of $R^1$ or $R^2$ in brackets and is any one of integers of 0 to 4; c represents the number of $R^4$ in brackets and is any one of integers of 0 to 2; d each independently represents the number of $R^5$ or $R^6$ in brackets and is any one of integers of 0 to 5, when each of $R^1$, $R^2$, $R^4$, $R^5$ or $R^6$ is plurally substituted, the substituents may be identical to or different from each other, two adjacent substituents may bond together to form a ring with carbon atoms bonded with the substituents, and * represents a bonding position.

3. A light-emitting material comprising the compound of claim 1.

4. A light-emitting element comprising the light-emitting material of claim 3.

* * * * *